United States Patent
Li et al.

(10) Patent No.: US 6,677,351 B2
(45) Date of Patent: Jan. 13, 2004

(54) 1-BIARYL-1,8-NAPHTHYRIDIN-4-ONE PHOSPHODIESTERASE-4 INHIBITORS

(75) Inventors: Chun Li, Thousand Oaks, CA (US); Mario Girard, St-Lazare (CA); Pierre Hamel, Vimont-Lavel (CA); Sebastien Laliberte, Ile Perrot (CA); Richard Friesen, Kirkland (CA); Yves Girard, Ille Bizard (CA); Daniel Guay, Notre Dame de L'lle Perrot (CA)

(73) Assignee: Merck Frosst Canada & Co., Quebec (CA)

( * ) Notice: Subject to any disclaimer, the term of this patent is extended or adjusted under 35 U.S.C. 154(b) by 0 days.

(21) Appl. No.: 10/154,591

(22) Filed: May 24, 2002

(65) Prior Publication Data
US 2003/0096829 A1 May 22, 2003

Related U.S. Application Data
(60) Provisional application No. 60/293,247, filed on May 24, 2001.

(51) Int. Cl.[7] ............... A61K 31/444; C07D 471/04
(52) U.S. Cl. ...................................... 514/300; 546/123
(58) Field of Search ......................... 546/123; 514/300

(56) References Cited

U.S. PATENT DOCUMENTS

| | | |
|---|---|---|
| 4,492,702 A | 1/1985 | Sherlock |
| 5,340,827 A | 8/1994 | Beeley et al. |
| 5,491,147 A | 2/1996 | Boyd et al. |
| 5,550,137 A | 8/1996 | Beeley et al. |
| 5,580,888 A | 12/1996 | Warrellow et al. |
| 5,608,070 A | 3/1997 | Alexander et al. |
| 5,622,977 A | 4/1997 | Warrellow et al. |
| 5,679,712 A | 10/1997 | Schwark et al. |
| 5,693,672 A | 12/1997 | Weichert et al. |
| 5,712,298 A | 1/1998 | Amschler |
| 5,736,297 A | 4/1998 | Roeschert et al. |
| 5,739,144 A | 4/1998 | Warrellow et al. |
| 5,747,541 A | 5/1998 | Weichert et al. |
| 5,776,958 A | 7/1998 | Warrellow et al. |
| 5,780,477 A | 7/1998 | Head et al. |
| 5,786,354 A | 7/1998 | Warrellow et al. |
| 5,798,373 A | 8/1998 | Warrellow |
| 5,849,770 A | 12/1998 | Head et al. |
| 5,859,034 A | 1/1999 | Warrellow et al. |
| 5,866,593 A | 2/1999 | Warrellow et al. |
| 5,891,896 A | 4/1999 | Warrellow et al. |

FOREIGN PATENT DOCUMENTS

| | | |
|---|---|---|
| EP | 811610 | 12/1997 |
| EP | 0 978 516 A1 | 2/2000 |
| WO | WO 94/22852 | 10/1994 |
| WO | WO 95/35283 | 12/1995 |
| WO | WO 96/00215 | 1/1996 |
| WO | WO 97 04775 | 2/1997 |
| WO | WO 98/25883 | 6/1998 |
| WO | WO 98/35683 | 8/1998 |
| WO | WO 99 07704 | 2/1999 |

OTHER PUBLICATIONS

C. Burnouf, et al., Ann. Rep. In Med. Chem., vol. 33, pp. 91–109, 1998.
S. B. Christensen, et al., J. Med. Chem., vol. 41, pp. 821–835, 1998.
A. H. Cook, et al., J. Chem. Soc., pp. 413–417, 1943.
M. D. Houslay, et al., Adv. In Pharmacol., vol. 44, pp. 225–342, 1998.
B. Hughes, et al., Br. J. Pharmacol., vol. 118, pp. 1183–1191, 1996.
K. Manabe, et a., J. Am. Chem., vol. 114(17, pp. 6940–6941, 1992.
K. Manabe, et al., J. Org. Chem., vol. 58(24, pp. 6692–6700, 1993.
K. Manabe, et al., J. Am. Chem. Soc., vol. 115(12), pp. 5324–5325, 1993.
M. J. Perry, et al., Cell Biochem. Biophys., vol. 29, pp. 113–132, 1998.
D. Spina, et al., Adv. In. Pharmacol., vol. 44, pp. 33–89, 1998.

*Primary Examiner*—Patricia L. Morris
(74) *Attorney, Agent, or Firm*—Curtis C. Panzer; David L. Rose

(57) ABSTRACT

Compounds represented by Formula (I):

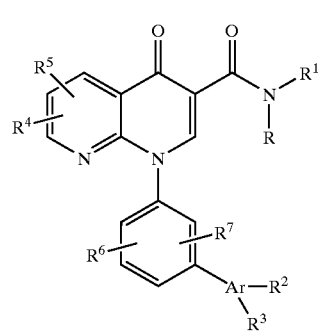

or a pharmaceutically acceptable salt thereof, are phosphodiesterrase 4 inhibitors useful in the treatment of asthma and inflammation.

10 Claims, No Drawings

1-BIARYL-1,8-NAPHTHYRIDIN-4-ONE PHOSPHODIESTERASE-4 INHIBITORS

This application claims the benefit of U.S. Patent Application No. 60/293,247, filed May 24, 2001.

BACKGROUND OF THE INVENTION

1. Field of the Invention

The present invention is directed to compounds that are biaryl substituted 1,8-naphthyridin-4(1H)-ones. In particular, this invention is directed to phenyl or pyridyl substituted 1,8-naphthyridin-4(1H)-ones which are phosphodiesterase-4 inhibitors wherein the phenyl or pyridyl group is at the 1-position and contains an aryl substituent group further optionally substituted.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3', 5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3', 5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), Ann. Rep. In Med. Chem., 33:91–109(1998). B. Hughes et al., Br. J. Pharmacol., 118:1183–1191(1996); M. J. Perry et al., Cell Biochem. Biophys., 29:113–132(1998); S. B. Christensen et al., J. Med. Chem., 41:821–835(1998); and Burnouf describe the wide variation of the severity of the undesirable side effects exhibited by various compounds. As described in M. D. Houslay et al., Adv. In Pharmacol., 44:225–342(1998) and D. Spina et al., Adv. In Pharmacol., 44:33–89(1998), there is great interest and research of therapeutic PDE4 inhibitors.

International Patent Publication WO9422852 describes quinolines as PDE4 inhibitors. International Patent Publication WO9907704 describes 1-aryl-1,8-naphthylidin-4-one derivatives as PDE4 inhibitors.

A. H. Cook, et al., J. Chem. Soc., 413–417(1943) describes gamma-pyridylquinolines. Other quinoline compounds are described in Kei Manabe et al., J. Org. Chem., 58(24):6692–6700(1993); Kei Manabe et al., J. Am. Chem. Soc., 115(12):5324–5325(1993); and Kei Manabe et al., J. Am. Chem. Soc., 114(17):6940–6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to biaryl substituted 1,8-naphthyridin-4(1H)-ones represented by Formula (I):

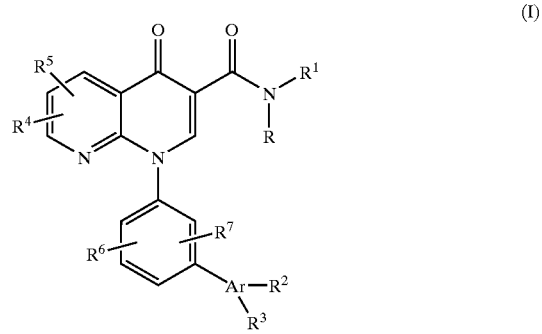

(I)

or pharmaceutically acceptable salts thereof, which are phosphodiesterase-4 inhibitors.

This invention also provides a pharmaceutical composition which includes an effective amount of the novel biaryl substituted 1,8-naphthyridin-4 (1H)-ones and a pharmaceutically acceptable carrier. This invention further provides a method of treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues by the administration of an effective amount of the novel substituted 1,8-naphthyridin-4(1H)-ones or a precursor compound which forms in vivo the novel biaryl substituted 1,8-naphthyridin-4(1H)-ones which are phosphodiesterase-4 inhibitors.

DETAILED DESCRIPTION OF THE INVENTION

A compound of this invention is represented by Formula (I):

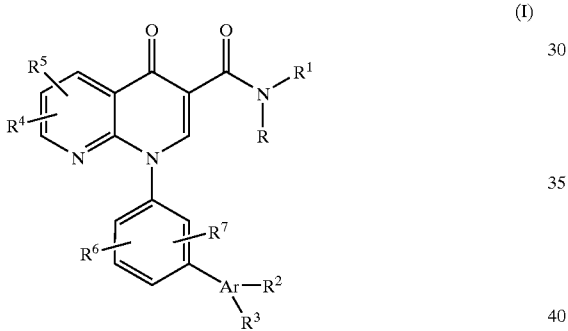

(I)

or a pharmaceutically acceptable salt thereof, wherein

Ar is phenyl, pyridyl, pyrimidyl, indolyl, quinolinyl, thienyl, pyridonyl, oxazolyl, oxadiazolyl, thiadiazolyl, or imidazolyl, or oxides thereof when Ar is a heteroaryl;

R is H or $-C_{1-6}$alkyl;

$R^1$ is H, or a $-C_{1-6}$alkyl, $-C_{3-6}$cycloalkyl, $-C_{1-6}$alkoxy, $-C_{2-6}$alkenyl, $-C_{3-6}$alkynyl, heteroaryl, or heterocycle group, wherein any of the groups is optionally substituted with 1–3 independent $-C_{1-6}$alkyl, $-C_{1-6}$alkoxy, OH, amino, $-(C_{0-6}$alkyl$)-SO_n-(C_{1-6}$alkyl), nitro, CN, $=N-O-C_{1-6}$alkyl, $-O-N=C_{1-6}$alkyl, or halogen substituents;

$R^2$ is H, halogen, $-C_{1-6}$alkyl, $-C_{3-6}$cycloalkyl, $-C_{1-6}$alkyl$(C_{3-6}$cycloalkyl$)(C_{3-6}$cycloalkyl$)$, $-C_{1-6}$alkoxy, phenyl, heteroaryl, heterocycle, amino, $-C(O)-C_{1-6}$alkyl, $-C(O)-O-C_{1-6}$alkyl, $-C_{1-6}$alkyl$(=N-OH)$, $-C(N=NOH)C_{1-6}$alkyl, $-C_{0-6}$alkyl(oxy)$C_{1-6}$alkyl-phenyl, $-SO_nNH(C_{0-6}$alkyl), or $-(C_{0-6}$alkyl$)-SO_n-(C_{1-6}$alkyl), wherein the phenyl, heteroaryl or heterocycle is optionally substituted with halogen, $-C_{1-6}$alkyl, $-C_{1-6}$alkoxy, hydroxy, amino, or $-C(O)-O-C_{1-6}$alkyl, and any alkyl is optionally substituted with 1–6 independent halogen or $-OH$ substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, $-C_{1-6}$alkyl, $-C_{1-6}$alkoxy, or amine, and any alkyl is optionally substituted with 1–6 independent halogen or $-OH$ substituents.

In one aspect, a compound of this invention is represented by Formula (I) or a pharmaceutically acceptable salt thereof, wherein Ar is phenyl;

R is H or $-C_{1-6}$alkyl;

$R^1$ is H, or a $-C_{1-6}$alkyl, $-C_{3-6}$cycloalkyl, $-C_{1-6}$alkoxy, $-C_{2-6}$alkenyl, $-C_{3-6}$alkynyl, heteroaryl, or heterocycle group, wherein any of the groups is optionally substituted with 1–3 independent $-C_{1-6}$alkyl, $-C_{1-6}$alkoxy, OH, amino, $-(C_{0-6}$alkyl$)-SO_n-(C_{1-6}$alkyl), nitro, CN, $=N-O-C_{1-6}$alkyl, $-O-N=C_{1-6}$alkyl, or halogen substituents;

$R^2$ is H, halogen, $-C_{1-6}$alkyl, $-C_{3-6}$cycloalkyl, $-C_{1-6}$alkyl$(C_{3-6}$cycloalkyl$)(C_{3-6}$cycloalkyl$)$, $-C_{1-6}$alkoxy, phenyl, heteroaryl, heterocycle, amino, $-C(O)-C_{1-6}$alkyl, $-C(O)-O-C_{1-6}$alkyl, $-C_{1-6}$alkyl$(=N-OH)$, $-C(N=NOH)C_{1-6}$alkyl, $-C_{0-6}$alkyl(oxy)$C_{1-6}$alkyl-phenyl, $-SO_nNH(C_{0-6}$alkyl), or $-(C_{0-6}$alkyl$)-SO_n-(C_{1-6}$alkyl), wherein the phenyl, heteroaryl or heterocycle is optionally substituted with halogen, $-C_{1-6}$alkyl, $-C_{1-6}$alkoxy, hydroxy, amino, or $-C(O)-O-C_{1-6}$alkyl, and any alkyl is optionally substituted with 1–6 independent halogen or $-OH$ substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, $-C_{1-6}$alkyl, $-C_{1-6}$alkoxy, or amine, and any alkyl is optionally substituted with 1–6 independent halogen or $-OH$ substituents.

In an embodiment of this one aspect, a compound of this invention is represented by Formula (I) or a pharmaceutically acceptable salt thereof, wherein Ar is phenyl;

R is H or $-C_{1-6}$alkyl;

$R^1$ is $-C_{1-6}$alkyl, optionally substituted with 1–3 independent $-C_{1-6}$alkyl, $-C_{1-6}$alkoxy, OH, amino, $-(C_{0-6}$alkyl$)-SO_n-(C_{1-6}$alkyl), nitro, CN, $=N-O-C_{1-6}$alkyl, $-O-N=C_{1-6}$alkyl, or halogen substituents;

$R^2$ is H, halogen, $-C_{1-6}$alkyl, $-C_{3-6}$cycloalkyl, $-C_{1-6}$alkyl$(C_{3-6}$cycloalkyl$)(C_{3-6}$cycloalkyl$)$, $-C_{1-6}$alkoxy, phenyl, heteroaryl, heterocycle, amino, $-C(O)-C_{1-6}$alkyl, $-C(O)-O-C_{1-6}$alkyl, $-C_{1-6}$alkyl$(=N-OH)$, $-C(N=NOH)C_{1-6}$alkyl, $-C_{0-6}$alkyl(oxy)$C_{1-6}$alkyl-phenyl, $-SO_nNH(C_{0-6}$alkyl), or $-(C_{0-6}$alkyl$)-SO_n-(C_{1-6}$alkyl), wherein the phenyl, heteroaryl or heterocycle is optionally substituted with halogen, $-C_{1-6}$alkyl, $-C_{1-6}$alkoxy, hydroxy, amino, or $-C(O)-O-C_{1-6}$alkyl, and any alkyl is optionally substituted with 1–6 independent halogen or $-OH$ substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In another embodiment of this one aspect, a compound of this invention is represented by Formula (I) or a pharmaceutically acceptable salt thereof, wherein Ar is phenyl;

R is H or —$C_{1-6}$alkyl;

$R^1$ is —$C_{3-6}$cycloalkyl, optionally substituted with 1–3 independent —$C_{1-6}$alkyl, —$C_{1-6}$alkoxy, OH, amino, —($C_{0-6}$alkyl)—$SO_n$—($C_{1-6}$alkyl), nitro, CN, =N—O—$C_{1-6}$alkyl, —O—N=$C_{1-6}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In still another embodiment of this one aspect, a compound of this invention is represented by Formula (I) or a pharmaceutically acceptable salt thereof, wherein Ar is phenyl;

R is H or —$C_{1-6}$alkyl;

$R^1$ is pyridyl, optionally substituted with 1–3 independent —$C_{1-6}$alkyl, —$C_{1-6}$alkoxy, OH, amino, —($C_{0-6}$alkyl)—$SO_n$—($C_{1-6}$alkyl), nitro, CN, =N—O—$C_{1-6}$alkyl, —O—N=$C_{1-6}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In a second aspect, a compound of this invention is represented by Formula (I) or a pharmaceutically acceptable salt thereof, wherein Ar is pyridyl, pyrimidyl, or oxides thereof;

R is H or —$C_{1-6}$alkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, heteroaryl, or heterocycle group, wherein any of the groups is optionally substituted with 1–3 independent —$C_{1-6}$alkyl, —$C_{1-6}$alkoxy, OH, amino, —($C_{0-6}$alkyl)—$SO_n$—($C_{1-6}$alkyl), nitro, CN, =N—O—$C_{1-6}$alkyl, —O—N=$C_{1-6}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In an embodiment of the second aspect, a compound of this invention is represented by Formula (I) or a pharmaceutically acceptable salt thereof, wherein Ar is pyridyl, pyrimidyl, or oxides thereof;

R is H;

$R^1$ is H;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In another embodiment of the second aspect, a compound of this invention is represented by Formula (I) or a pharmaceutically acceptable salt thereof, wherein Ar is pyridyl, pyrimidyl, or oxides thereof;

R is H or —$C_{1-6}$alkyl;

$R^1$ is —$C_{1-6}$alkyl, optionally substituted with 1–3 independent —$C_{1-6}$alkyl, —$C_{1-6}$alkoxy, OH, amino, —($C_{0-6}$ alkyl)—$SO_n$—($C_{1-6}$alkyl), nitro, CN, =N—O—$C_{1-6}$ alkyl, —O—N=$C_{1-6}$alkyl, or halogen substituents;

R$^2$ is H, halogen, —C$_{1-6}$alkyl, —C$_{3-6}$cycloalkyl, —C$_{1-6}$alkyl(C$_{3-6}$cycloalkyl)(C$_{3-6}$cycloalkyl), —C$_{1-6}$alkoxy, phenyl, heteroaryl, heterocycle, amino, —C(O)—C$_{1-6}$alkyl, —C(O)—O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, —SO$_n$NH(C$_{0-6}$alkyl), or —(C$_{0-6}$alkyl)—SO$_n$—(C$_{1-6}$alkyl), wherein the phenyl, heteroaryl or heterocycle is optionally substituted with halogen, —C$_{1-6}$alkyl, —C$_{1-6}$alkoxy, hydroxy, amino, or —C(O)—O—C$_{1-6}$alkyl, and any alkyl is optionally substituted with 1–6 independent halogen or —OH substituents;

n is 0, 1, or 2;

R$^3$ is H, OH, amine, halogen or C$_{1-6}$alkyl, wherein the alkyl is optionally substituted with 1–6 independent halogen, OH, or amine substituents; and R$^4$, R$^5$, R$^6$, and R$^7$ each independently is H, halogen, —C$_{1-6}$alkyl, —C$_{1-6}$alkoxy, or amine, and any alkyl is optionally substituted with 1–6 independent halogen or —OH substituents.

In still another embodiment of the second aspect, a compound of this invention is represented by Formula (I) or a pharmaceutically acceptable salt thereof, wherein Ar is pyridyl, pyrimidyl, or oxides thereof;

R is H or —C$_{1-6}$alkyl;

R$^1$ is —C$_{3-6}$cycloalkyl, optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-16}$alkyl, —O—N=C$_{1-6}$alkyl, or halogen substituents;

R$^2$ is H, halogen, —C$_{1-6}$alkyl, —C$_{3-6}$cycloalkyl, —C$_{1-6}$alkyl(C$_{3-6}$cycloalkyl)(C$_{3-6}$cycloalkyl), —C$_{1-6}$alkoxy, phenyl, heteroaryl, heterocycle, amino, —C(O)—C$_{1-6}$alkyl, —C(O)—O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, —SO$_n$NH(C$_{0-6}$alkyl), or —(C$_{0-6}$alkyl)—SO$_n$—(C$_{1-6}$alkyl), wherein the phenyl, heteroaryl or heterocycle is optionally substituted with halogen, —C$_{1-6}$alkyl, —C$_{1-6}$alkoxy, hydroxy, amino, or —C(O)—O—C$_{1-6}$alkyl, and any alkyl is optionally substituted with 1–6 independent halogen or —OH substituents;

n is 0, 1, or 2;

R$^3$ is H, OH, amine, halogen or C$_{1-6}$alkyl, wherein the alkyl is optionally substituted with 1–6 independent halogen, OH, or amine substituents; and R$^4$, R$^5$, R$^6$, and R$^7$ each independently is H, halogen, —C$_{1-6}$alkyl, —C$_{1-6}$alkoxy, or amine, and any alkyl is optionally substituted with 1–6 independent halogen or —OH substituents.

In yet another embodiment of the second aspect, a compound of this invention is represented by Formula (I) or a pharmaceutically acceptable salt thereof, wherein Ar is pyridyl, pyrimidyl, or oxides thereof;

R is H or —C$_{1-6}$alkyl;

R$^1$ is pyridyl, optionally substituted with 1–3 independent —C$_{1-6}$alkyl, —C$_{1-6}$alkoxy, OH, amino, —(C$_{0-6}$alkyl)—SO$_n$—(C$_{1-16}$alkyl), nitro, CN, =N—O—C$_{1-6}$alkyl, —O—N=C$_{1-6}$alkyl, or halogen substituents;

R$^2$ is H, halogen, —C$_{1-6}$alkyl, —C$_{3-6}$cycloalkyl, —C$_{1-6}$alkyl(C$_{3-6}$cycloalkyl)(C$_{3-6}$cycloalkyl), —C$_{1-6}$alkoxy, phenyl, heteroaryl, heterocycle, amino, —C(O)—C$_{1-6}$alkyl, —C(O)—O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, —SO$_n$NH(C$_{0-6}$alkyl), or —(C$_{0-6}$alkyl)—SO$_n$—(C$_{1-6}$alkyl), wherein the phenyl, heteroaryl or heterocycle is optionally substituted with halogen, —C$_{1-6}$alkyl, —C$_{1-6}$alkoxy, hydroxy, amino, or —C(O)—O—C$_{1-6}$alkyl, and any alkyl is optionally substituted with 1–6 independent halogen or —OH substituents;

n is 0, 1, or 2;

R$^3$ is H, OH, amine, halogen or C$_{1-6}$alkyl, wherein the alkyl is optionally substituted with 1–6 independent halogen, OH, or amine substituents; and R$^4$, R$^5$, R$^6$, and R$^7$ each independently is H, halogen, —C$_{1-6}$alkyl, —C$_{1-6}$alkoxy, or amine, and any alkyl is optionally substituted with 1–6 independent halogen or —OH substituents.

In a third aspect, a compound of this invention is represented by Formula (I) or a pharmaceutically acceptable salt thereof, wherein Ar is indolyl, quinolinyl, or oxides thereof;

R is H or —C$_{1-6}$alkyl;

R$^1$ is H, or a —C$_{1-6}$alkyl, —C$_{3-6}$cycloalkyl, —C$_{1-6}$alkoxy, —C$_{2-6}$alkenyl, —C$_{3-6}$alkynyl, heteroaryl, or heterocycle group, wherein any of the groups is optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-6}$alkyl, —O—N=C$_{1-6}$alkyl, or halogen substituents;

R$^2$ is H, halogen, —C$_{1-6}$alkyl, —C$_{3-6}$cycloalkyl, —C$_{1-6}$alkyl(C$_{3-6}$cycloalkyl)(C$_{3-6}$cycloalkyl), —C$_{1-6}$alkoxy, phenyl, heteroaryl, heterocycle, amino, —C(O)—C$_{1-6}$alkyl, —C(O)—O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, —SO$_n$NH(C$_{0-6}$alkyl), or —(C$_{0-6}$alkyl)—SO$_n$—(C$_{1-6}$alkyl), wherein the phenyl, heteroaryl or heterocycle is optionally substituted with halogen, —C$_{1-6}$alkyl, —C$_{1-6}$alkoxy, hydroxy, amino, or —C(O)—O—C$_{1-6}$alkyl, and any alkyl is optionally substituted with 1–6 independent halogen or —OH substituents;

n is 0, 1, or 2;

R$^3$ is H, OH, amine, halogen or C$_{1-6}$alkyl, wherein the alkyl is optionally substituted with 1–6 independent halogen, OH, or amine substituents; and R$^4$, R$^5$, R$^6$, and R$^7$ each independently is H, halogen, —C$_{1-6}$alkyl, —C$_{1-6}$alkoxy, or amine, and any alkyl is optionally substituted with 1–6 independent halogen or —OH substituents.

In an embodiment of the third aspect, a compound of this invention is represented by Formula (I) or a pharmaceutically acceptable salt thereof, wherein Ar is indolyl;

R is H or —C$_{1-6}$alkyl;

R$^1$ is —C$_{1-6}$alkyl, optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-6}$alkyl, —O—N=C$_{1-16}$alkyl, or halogen substituents;

R$^2$ is H, halogen, —C$_{1-6}$alkyl, —C$_{3-6}$cycloalkyl, —C$_{1-6}$alkyl(C$_{3-6}$cycloalkyl)(C$_{3-6}$cycloalkyl), —C$_{1-6}$alkoxy, phenyl, heteroaryl, heterocycle, amino, —C(O)—C$_{1-6}$alkyl, —C(O)O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, —SO$_n$NH(C$_{0-6}$alkyl), or —(C$_{0-6}$alkyl)—SO$_n$—(C$_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In another embodiment of the third aspect, a compound of this invention is represented by Formula (I) or a pharmaceutically acceptable salt thereof, wherein Ar is quinolinyl or oxide thereof;

R is H or —$C_{1-6}$alkyl;

$R^1$ is —$C_{1-6}$alkyl, optionally substituted with 1–3 independent —$C_{1-6}$alkyl, —$C_{1-6}$alkoxy, OH, amino, —($C_{0-6}$ alkyl)—$SO_n$—($C_{1-6}$alkyl), nitro, CN, =N—O—$C_{1-6}$ alkyl, —O—N=$C_{1-16}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In a fourth aspect, a compound of this invention is represented by Formula (I) or a pharmaceutically acceptable salt thereof, wherein Ar is thienyl;

R is H or —$C_{1-6}$alkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, heteroaryl, or heterocycle group, wherein any of the groups is optionally substituted with 1–3 independent —$C_{1-6}$alkyl, —$C_{1-6}$alkoxy, OH, amino, —($C_{0-6}$alkyl)—$SO_n$—($C_{1-6}$alkyl), nitro, CN, =N—O—$C_{1-6}$alkyl, —O—N=$C_{1-6}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —C -6alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In an embodiment of the fourth aspect, a compound of this invention is represented by Formula (I) or a pharmaceutically acceptable salt thereof, wherein Ar is thienyl;

R is H or —$C_{1-6}$alkyl;

$R^1$ is —$C_{3-6}$cycloalkyl, optionally substituted with 1–3 independent —$C_{1-6}$alkyl, —$C_{1-6}$alkoxy, OH, amino, —($C_{0-6}$alkyl)—$SO_n$—($C_{1-6}$alkyl), nitro, CN, =N—O—$C_{1-6}$alkyl, —O—N=$C_{1-6}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In a fifth aspect, a compound of this invention is represented by Formula (I) or a pharmaceutically acceptable salt thereof, wherein Ar is pyridonyl;

R is H or —$C_{1-6}$alkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, heteroaryl, or heterocycle group, wherein any of the groups is optionally substituted with 1–3 independent —$C_{1-6}$alkyl, —$C_{1-6}$alkoxy, OH, amino, —($C_{0-6}$alkyl)—$SO_n$—($C_{1-6}$alkyl), nitro, CN, =N—O—$C_{1-6}$alkyl, —O—N=$C_{1-6}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

In an embodiment of the fifth aspect, a compound of this invention is represented by Formula (I) or a pharmaceutically acceptable salt thereof, wherein Ar is pyridonyl;

R is H or —$C_{1-6}$alkyl;

$R^1$ is —$C_{3-6}$cycloalkyl, optionally substituted with 1–3 independent —$C_{1-6}$alkyl, —$C_{1-6}$alkoxy, OH, amino, —($C_{0-6}$alkyl)—$SO_n$—($C_{1-16}$alkyl), nitro, CN, =N—O—$C_{1-6}$alkyl, —O—N=$C_{1-16}$alkyl, or halogen substituents;

$R^2$ is H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and any alkyl is optionally substituted with 1–6 independent halogen or —OH substituents;

n is 0, 1, or 2;

$R^3$ is H, OH, amine, halogen or $C_{1-6}$alkyl, wherein the alkyl is optionally substituted with 1–6 independent halogen, OH, or amine substituents; and $R^4$, $R^5$, $R^6$, and $R^7$ each independently is H, halogen, —$C_{1-6}$alkyl, —$C_{1-6}$alkoxy, or amine, and any alkyl is optionally substituted with 1–6 independent halogen or —OH substituents.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

Ther term "$C_0$–$C_6$alkyl" includes alkyls containing 6, 5, 4, 3, 2, 1, or no carbon atoms. An alkyl with no carbon atoms is a hydrogen atom substituent or a direct bond—depending on whether the alkyl is a terminus or a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

Examples of aryl($C_{1-6}$)alkyl include, for example, phenyl ($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)O$C_1$–$C_4$alkyl, and —OC(O)NH$C_1$–$C_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$) alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.001 mg/kg to about 140 mg/kg of body weight per day are useful in the treatment of conditions such as asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues which are responsive to PDE4 inhibition, or alternatively about 0.05 mg to about 7 g per patient per day. For example, inflammation may be effectively treated by the administration of from about 0.01 mg to 50 mg of the compound per kilogram of body weight per day, or alternatively about 0.5 mg to about 2.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 0.01 mg to about 1000 mg of the active ingredient, typically 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues—maladies that are amenable to amelioration through inhibition of the PDE4 isoenzyme and the resulting elevated cCAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) H1 (histamine) receptor antagonists and ix) beta 2 adrenoceptor agonist.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| $Et_3N$ = | triethylamine |
| GST | glutathione transferase |
| HMDS | hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt $6H_2O$ |
| Ms = | methanesulfonyl = mesyl = $SO_2Me$ |
| MsO = | methanesulfonate = mesylate |
| NSAID = | non-steroidal anti-inflammatory drug |
| o-Tol = | ortho-tolyl |
| OXONE ® = | $2KHSO_5 \cdot KHSO_4 \cdot K_2SO_4$ |
| PCC = | pyridinium chlorochromate |
| PDC = | pyridinium dichromate |
| PDE | phosphodiesterase |
| Ph = | phenyl |
| Phe = | benzenediyl |
| PMB = | para-methoxybenzyl |
| Pye = | pyridinediyl |
| r.t. = | room temperature |
| Rac. = | racemic |
| SAM = | aminosulfonyl or sulfonamide or $SO_2NH_2$ |
| SEM = | 2-(trimethylsilyl)ethoxymethoxy |
| SPA = | scintillation proximity assay |
| TBAF = | tetra-n-butylammonium fluoride |
| Th = | 2- or 3-thienyl |
| TFA = | trifluoroacetic acid |
| TFAA = | trifluoroacetic acid anhydride |
| THF = | tetrahydrofuran |
| Thi = | thiophenediyl |

-continued

| | |
|---|---|
| TLC = | thin layer chromatography |
| TMS-CN = | trimethylsilyl cyanide |
| TMSI = | trimethylsilyl iodide |
| Tz = | 1H (or 2H)-tetrazol-5-yl |
| CAN | ceric ammonium nitrate |
| $C_3H_5$ = | allyl |

| Alkyl Group Abbreviations | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

Assays Demonstrating Biological Activity

LPS and FMLP-Induced TNF-α and $LTB_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and $LTB_4$. Upon stimulation with LPS, activated monocytes express and secrete TNF-α up to 8 hours and plasma levels remain stable for 24 hours. Published studies have shown that inhibition of TNF-α by increasing intracellular cAMP via $PDE_4$ inhibition and/or enhanced adenylyl cyclase activity occurs at the transcriptional level. $LTB_4$ synthesis is also sensitive to levels of intracellular cAMP and can be completely inhibited by $PDE_4$-selective inhibitors. As there is little $LTB_4$ produced during a 24 hour LPS stimulation of whole blood, an additional LPS stimulation followed by fMLP challenge of human whole blood is necessary for $LTB_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 μL aliquots of blood were pre-incubated with either 2 μL of vehicle (DMSO) or 2 μL of test compound at varying concentrations for 15 minutes at 37° C. This was followed by the addition of either 10 μL vehicle (PBS) as blanks or 10 μL LPS (1 μg/mL final concentration, #L-2630 (Sigma Chemical Co., St. Louis, Mo.) from E. coli, serotype 0111:B4; diluted in 0.1% w/v BSA (in PBS)). After 24 hours of incubation at 37° C., another 10 μL of PBS (blank) or 10 μL of LPS (1 μg/mL final concentration) was added to blood and incubated for 30 minutes at 37° C. The blood was then challenged with either 10 μL of PBS (blank) or 10 μL of fMLP (1 μM final concentration, #F-3506 (Sigma); diluted in 1% w/v BSA (in PBS)) for 15 minutes at 37° C. The blood samples were centrifuged at 1500× g for 10 minutes at 4° C. to obtain plasma. A 50 μL aliquot of plasma was mixed with 200 μL methanol for protein precipitation and centrifuged as above. The supernatant was assayed for $LTB_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. The $IC_{50}$ values of Examples 1 to 76 generally ranged from 0.005 μM to 15.4 μM.

Anti-Allergic Activity In Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered antihistamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. was added the test compound (dissolved in 2 μL DMSO), 188 mL of substrate buffer containing [2,8-$^3$H] adenosine 3′,5′-cyclic phosphate (cAMP, 100 nM to 50 μM), 10 mM $MgCl_2$, 1 mM EDTA, 50 mM Tris, pH 7.5. The reaction was initiated by the addition of 10 mL of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit using the standard 4-parameter/multiple binding sites equation from a ten point titration.

The $IC_{50}$ values of Examples 1 to 76 were determined with 100 nM cAMP using the purified GST fusion protein of the human recombinant phosphodiesterase IVa (met-248) produced from a baculovirus/Sf-9 expression system. The $IC_{50}$ values of Examples 1–76 generally ranged from 0.1 nM to 14.8 nM, although six examples had an $IC_{50}$ value between 34.3 and 134.0 nM.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm Hg) with a bath temperature of up to 60° C. The course of reactions was followed by thin layer chromatography (TLC) and reaction times are given for illustration only. Melting points are uncorrected and "d" indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)),mL (milliliters), g (gram(s)), mg (milligrams(s)), mol (moles),mmol (millimoles), eq (equivalent(s)).

Methods of Synthesis

Compounds of the present invention can be prepared according to the following methods. The substituents are the same as in Formula I except where defined otherwise.

Scheme 1

In a first method outlined in Scheme 1 below, an appropriately substituted derivative of ethyl 2-chloronicotinoyl acetate of formula II is reacted with 1.5 equivalents of triethyl orthoformate and 5 equivalents of acetic anhydride at 130° C., and after removal of the volatile components, the crude 2-chloronicotinoyl acrylate of formula III is immediately reacted with 1.2 equivalents of an appropriately substituted haloaryl amine of formula IV, such as, for example 3-bromoaniline, in a halogenated hydrocarbon solvent such as methylene chloride at a temperature of 0° C. to room temperature. After an appropriate reaction time ranging from 2 to 24 hours the resulting 3-arylamino acrylate of formula V is obtained by evaporation of the solvent and may be further purified by chromatography on silica gel or crystallization from an appropriate solvent.

The compound of formula V may alternatively be used without further purification in the following step. Cyclization of the compound of formula V to the 1-haloaryl-1,4-dihydro[1,8]naphthyridin-4-one carboxylate of formula VI is effected by treatment with a small excess of a strong base such as an alkali metal hydride, for example sodium hydride, in an appropriate solvent such as tetrahydrofuran at a starting temperature of 0° C. with warming to room temperature if required to complete the process. The product of formula VI is isolated in crude form by dilution with a large volume of water followed by filtration or by extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

The product of formula VI thus obtained can be hydrolyzed to the corresponding carboxylic acid derivative under basic conditions, using an aqueous solution of an alkali base such as an alkali carbonate or preferably sodium or potassium hydroxide, with an organic cosolvent such as tetrahydrofuran or a primary, secondary or tertiary alkanol, such as methanol or ethanol, or a combination thereof at temperatures ranging from room temperature to reflux temperature for the appropriate time. The resultant carboxylic acid is isolated in crude form following acidification using an aqueous solution of an inorganic acid such as hydrochloric, sulfuric or a similar acid, and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

The carboxylic acid is then transformed into the appropriate primary, secondary or tertiary amide analog of formula VII by any general procedure well known to the organic chemist, preferably via initial transformation into a mixed anhydride by treatment with a small excess, such as 1.25 equivalents, of an appropriate alkyl chloroformate such as ethyl or isobutyl chloroformate, in the presence of a larger excess, such as 2.5 equivalents, of a tertiary organic amine such as triethylamine or N,N-diisopropylethylamine in an organic solvent such as tetrahydrofuran at low temperature, preferably 0° C., for a period of 30 minutes to 3 hours. An excess, usually 5 or more equivalents, of an appropriate primary or secondary amine or of an aqueous solution of ammonium hydroxide is then added and the resulting reaction is allowed to proceed at a temperature ranging from 0° C. to room temperature for an appropriate length of time, usually 1–24 hours.

The desired amide of formula VII is then isolated in crude form by precipitation with water and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration. In cases where the amide moiety is 2,6-dichloropyridin-4-yl, a different procedure is used in which the anion of 4-amino-3,5-dichloropyridine is generated at low temperature, preferably at 0° C., using a strong alkali hydride such as sodium hydride in a solvent such as tetrahydrofuran, and reacted with the acid chloride of a carboxylic acid (from hydrolysis of an ester of formula VI) generated by an appropriate known procedure, usually by the action of oxalyl chloride activated by a catalytic amount of N,N-dimethylformamide in a solvent such as tetrahydrofuran.

The amides of general formula VII are processed into the products of formula I by reaction with an appropriately substituted aryl or heteroaryl boronic acid or boronate ester of formula VIII under the catalysis of a transition metal species such as trans-dibromobis(triphenylphosphine) palladium (II) or [1,1'-bis(diphenylphosphino)ferrocene] dichloropalladium(II) in an appropriate solvent or solvent mixture, preferably a 1:1 mixture of toluene and ethanol in the presence of an excess of an aqueous solution of an alkali base such as sodium carbonate, at an appropriate temperature, preferably 50 to 100° C., for an appropriate length of time ranging from 0.5 to 48 hours.

The resulting reaction product is then isolated in crude form by precipitation with water and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

Compounds of formula I may also be obtained by reaction of a compound of formula VII with an appropriately substituted aryl or heteroaryl tributyl stannane of formula IX under the catalysis of a transition metal species such as trans-dibromobis(triphenylphosphine)palladium (II) or [1,1'-bis(diphenylphosphino)ferrocene]dichloropalladium (II) in the presence of a copper (I) species such as cuprous iodide an appropriate solvent such as N,N-dimethylformamide at a temperature range of 50–100° C. for a period of 2 to 24 hours. Isolation of the reaction product is effected as described above.

Alternatively, an ester of formula VI can be processed into an ester of formula X by reaction with an appropriately substituted boronic acid or boronate ester, or with an appropriately substituted stannane derivative under the conditions described above, and the ester can be hydrolyzed and transformed into an amide of formula I.

The boronic acids of formula VIII or corresponding boronate esters are usually obtained from commercial sources. Where required, they can be prepared readily from the corresponding halides via metallation with n-butyllithium followed by reaction with a trialkyl borate, or by using classical transition metal-catalyzed coupling procedures using diboron pinacol ester. The stannanes of formula IX are generated from the corresponding halides via initial metallation using n-butyllithium followed by addition of tributyltin chloride.

Scheme 1

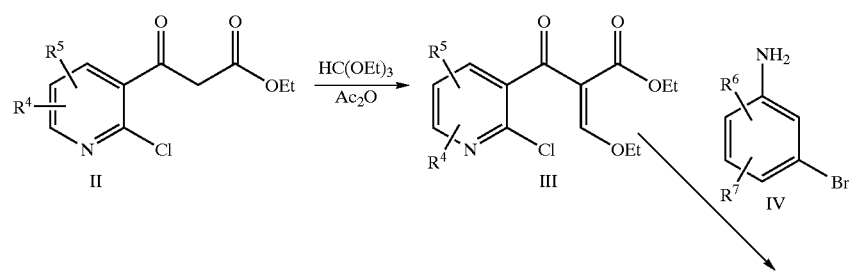

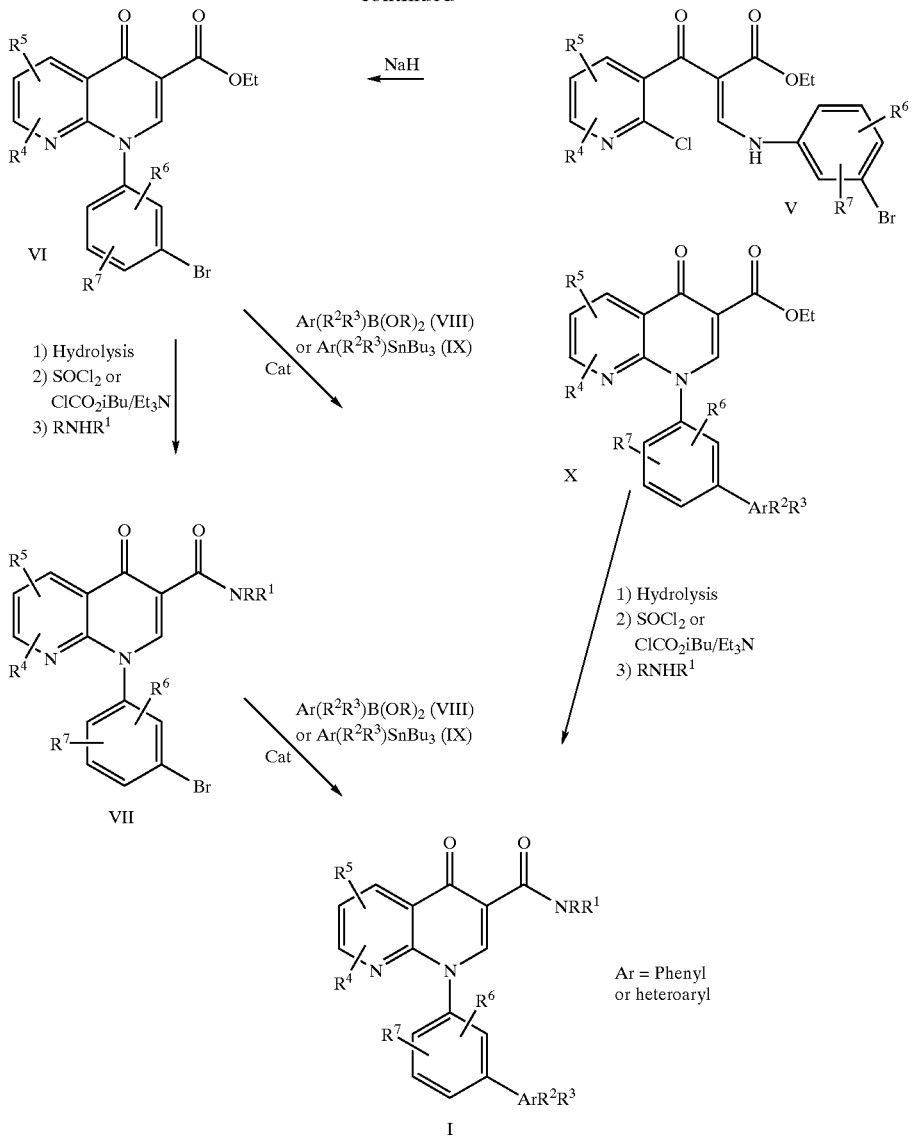

Ar = Phenyl or heteroaryl

Scheme 2

In an alternative method for the preparation of compounds of formula I, outlined in Scheme 2 below, an amide of formula VII can be transformed into a corresponding boronate ester of formula XI by treatment with an excess of diboron pinacol ester in the presence of an inorganic salt such as potassium acetate under the catalysis of a transition metal species such as trans-dibromobis(triphenylphosphine) palladium (II) or [1,1'-bis(diphenylphosphino)ferrocene] dichloropalladium(II) in a solvent such as N,N-dimethylformamide at temperatures ranging from 50 to 100° C. for a length of time ranging from 1 to 48 hours. The boronate of formula XI may be isolated by precipitation with water and filtration or extraction into an appropriate organic solvent such as diethyl ether, ethyl acetate, or a halogenated hydrocarbon solvent such as chloroform or methylene chloride. The resulting product can be further purified by chromatography on silica gel, crystallization or prolonged stirring in an appropriate solvent followed by filtration.

Alternatively, the boronate of formula XI can be used as generated in situ in the reaction medium without isolation, and reacted with a small excess of an appropriately substituted aryl or heteroaryl halide of formula XII under the catalysis of a transition metal species such as [1,1'-bis(diphenylphosphino)ferrocene]dichloropalladium(II) in an appropriate solvent or solvent mixture, preferably a 1:1 mixture of toluene and ethanol in the presence of an excess of an aqueous solution of an alkali base such as sodium carbonate, at an appropriate temperature, preferably 50 to 100° C. for an appropriate length of time ranging from 0.5 to 48 hours.

The reaction product of formula I is then isolated in crude form by precipitation with water and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

Scheme 2

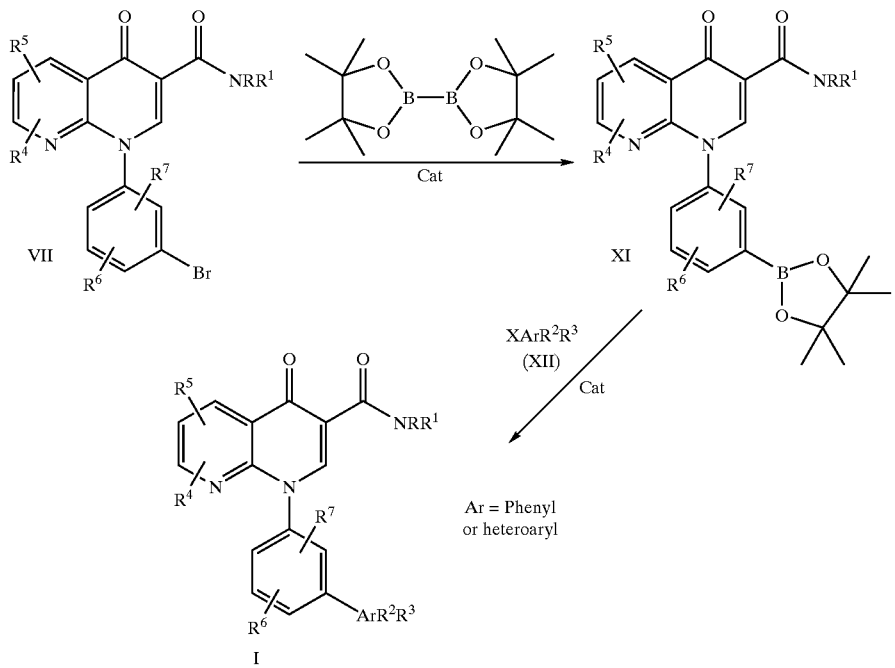

Scheme 3

In a third method used for the synthesis of compounds of formula I of this invention (scheme 3), an intermediate nicotinoyl acrylate of formula III is reacted with an appropriately constructed diaryl or heteroarylaryl amine of formula XII under the conditions described previously to afford a compound of formula XIV which is cyclized by the action of a strong base such as sodium hydride as described above to afford an ester of formula X which is processed into a compound of formula I via hydrolysis and amide formation as described above.

Scheme 3

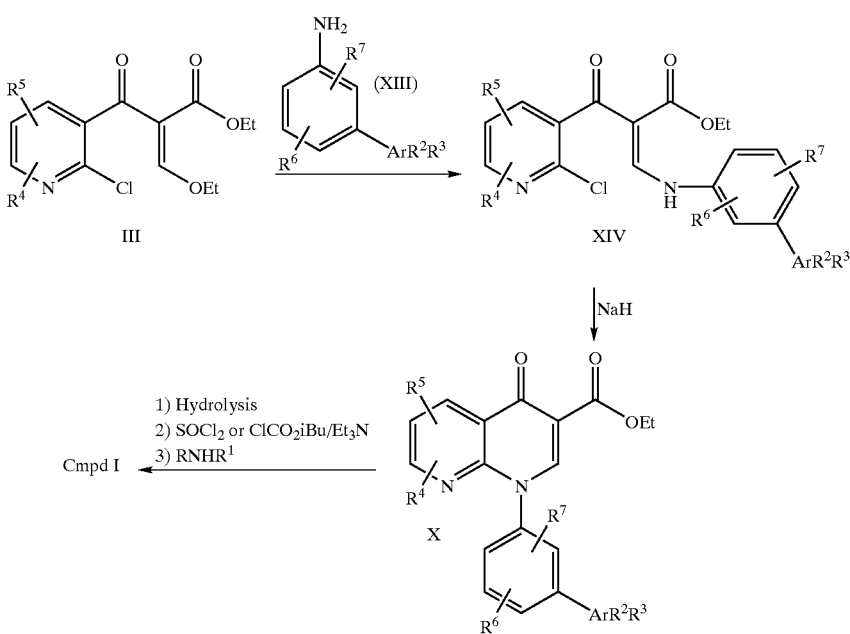

Scheme 4

The diaryl or heteroarylarylamine intermediates of formula XIII were assembled as indicated in Scheme 4. An appropriately substituted aniline boronic acid of formula XV is coupled with an appropriately substituted aryl or heteroaryl halide of general formula XII under the catalysis of a transition metal species as described above to afford the formula XIII compounds used in Scheme 3.

Scheme 4

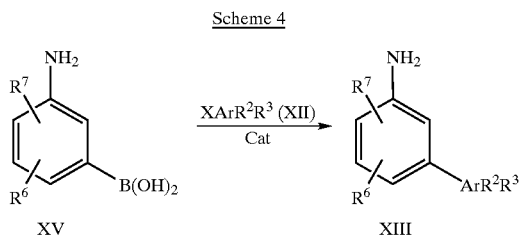

Scheme 5

Bromopyridine intermediates substituted at the 2-position by carbon based nucleophiles of formula XVII, where $R^8$ is selected from $R^2$ moieties having a carbon—carbon link to the pyridine, are conveniently prepared as shown in Scheme 5. The bromopyridine intermediates are prepared from dihalides of formula XVI by treatment with an appropriate solution of a Grignard reagent under the catalysis of a transition metal species such as [1,1'-bis(diphenylphosphino)ferrocene]dichloronickel (II) in a solvent such as tetrahydrofuran at a temperature range of −10° C. to room temperature and the resulting reaction mixture worked up by well known procedures to afford the desired product.

Scheme 5

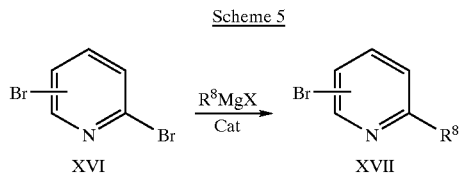

Scheme 6

Halopyridine intermediates of type XVIII where the 2-substituent is an alkoxy group $OR^9$ are derived from dihalides of formula XVI by displacement with an appropriate alkali alkoxide as outlined in scheme 6. The reaction is effected in a solvent such as N,N-dimethylformamide at a temperature range of 0° C. to room temperature and, upon completion of the reaction, the products are isolated and purified following classical procedures.

Scheme 6

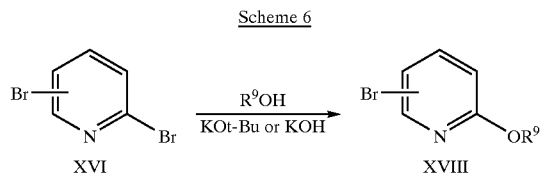

Scheme 7

Where intermediates of formula XIX or XX in which the 2-substituent is sulfide, sulfoxide or sulfone were required, they were attained as described in Scheme 7. An appropriate dihalopyridine of type XVI is reacted with an appropriate thioalkoxide, usually generated from the corresponding thiol or disulfide through the action of a strong base such as an alkali hydride or n-butyllithium, in a solvent such as N,N-dimethylformamide or diethyl ether at a temperature range of −78° C. to room temperature. Upon completion of the reaction the products of formula XIX are isolated and purified following classical procedures. The products thus obtained can be oxidized to the corresponding sulfoxides or sulfones of formula XX through the action of an oxidizing agent such as oxone or an organic peracid. In Scheme 7, $R^{10}$ is H or $C_{1-6}$alkyl.

Scheme 7

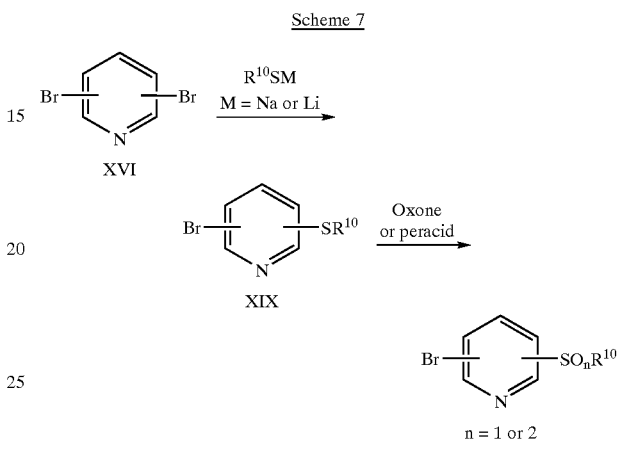

Scheme 8

The preparation of haloacyl pyridine intermediates of formula XXII, presented in Scheme 8, requires treatment of a halopyridine ester of type XXI with a solution of an appropriate Grignard reagent in a solvent such as diethyl ether at a temperature range of 0° C. to room temperature. If the reaction is carried out for a longer period or under reflux a halopyridine carbinol of formula XXIII is obtained. In Schemes 8 and 9, $R^7$ is $C_{1-6}$alkyl and $R^6$ is methyl or ethyl.

Scheme 8

Scheme 9

Scheme 9 outlines an alternative sequence for the synthesis of certain halopyridine carbinols of type XXIII. When 2,5-dibromopyrine is treated with n-butyllithium in toluene at −78° C. followed by addition of an appropriate ketone or aldehyde and subsequent quenching at −78° C., a carbinol of type XXIII results where the carbinol group occupies the 2-position of the pyridine ring. If the metallation step is performed in diethyl ether, the same process leads to an intermediate of formula XXIII in which the carbinol group occupies the 5-position of the pyridine ring.

Scheme 9

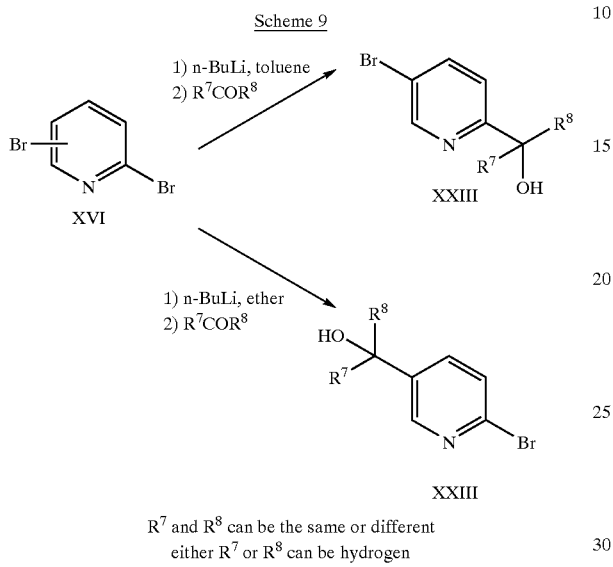

$R^7$ and $R^8$ can be the same or different
either $R^7$ or $R^8$ can be hydrogen Scheme 10

Scheme 10 demonstrates the methods of synthesis for compounds of formula I in which $R^2$ is a substituted phenyl or heteroaryl group. An intermediate compound of Type I where $R^2$ is a halogen is reacted with an appropriately substituted boronic acid or boronate ester of formula VII or tributyl stannane of formula IX using one of the methods described above to afford the desired compound.

Scheme 10

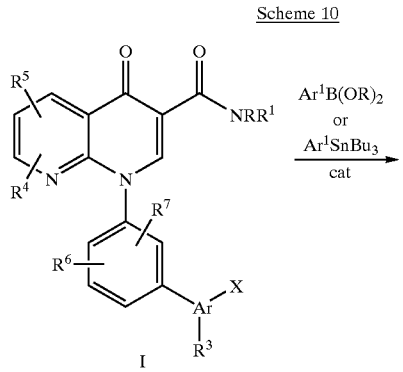

-continued

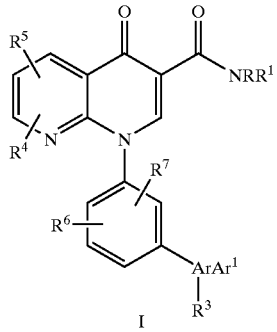

Scheme 11

Various further transformations on pre-assembled compounds of formula I are illustrated in Scheme 11. In cases where the Ar group is a pyridine or quinoline group it can be oxidized to the corresponding nitrogen oxide by the action of an appropriate oxidizing agent such as m-chloroperioxybenzoic acid or magnesium monoperoxyphthalate under commonly used conditions. In cases where one or more of the substituents on the Ar group is a ketone it is conveniently transformed into an oxime analog through the action of hydroxylamine in pyridine as solvent. A sulfide substituent is easily oxidized to the corresponding sulfoxide or sulfone derivative by using an appropriate quantity of an oxidant such as oxone or an organic peracid.

The transformation of a 2-benzyloxypyridine into the corresponding 2-pyridone was accomplished by treatment with trifluoroacetic acid in a solvent such as methylene chloride at room temperature or under slight warming. The removal of a tert-butyloxycarbonyl protecting group from a piperazine ring is effected by reaction with trifluoroacetic acid in a solvent such as 1,2-dichloroethane at reflux temperature. In examples where a substituent on Ar is a hydroxymethyl group it can be derivatized to the analogous halomethyl moiety using a tetrahalomethane in the presence of a trisubstituted phosphine such as triphenylphosphine or diphos in a solvent such as methylene chloride. The halide can be displaced by an appropriate sulfinic acid sodium salt to afford the alkyl or arylsulfonylmethyl analog.

Scheme 11

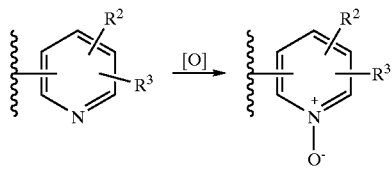

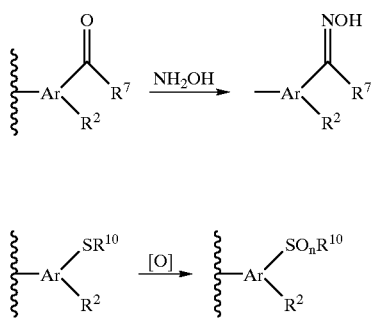

n = 1 or 2

-continued

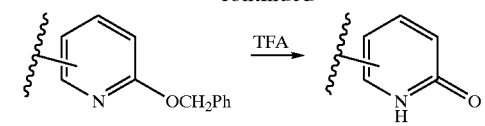

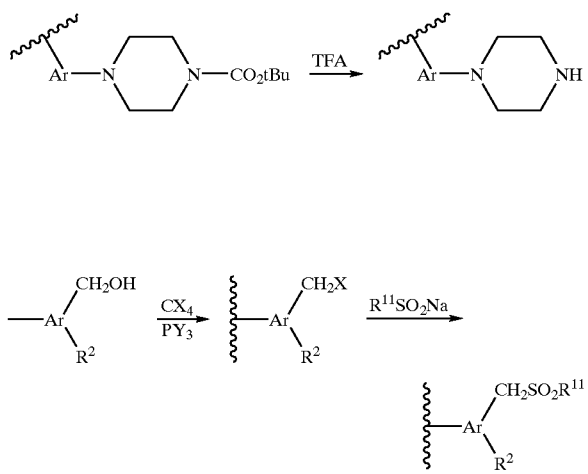

Scheme 12

The transformation of a 1-hydroxy-1-methylalkyl derivative such as exemplified by compounds of type XXIV of scheme 12 into 1,2-dihydroxyalkyl analogs of type XXVI is effected via initial acid-catalyzed dehydration, for example by heating in aqueous sulfuric acid, to afford an intermediate 1-alkylvinyl species of type XXV which is transformed into the desired diol XXVI by a dihydroxylation process, using for example an oxidant such as 4-methylmorpholine N-oxide (NMO) in the presence of a catalytic quantity of potassium osmate dihydrate.

Scheme 12

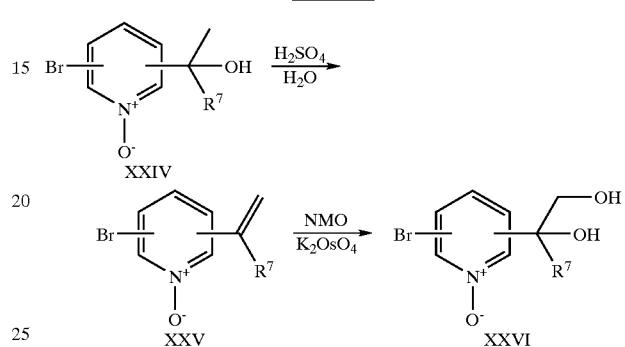

EXAMPLES

EXAMPLES of the present invention are summarized in the following table referring to Formula (I):

TABLE 1

I

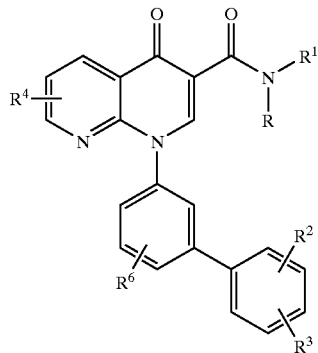

| EX. | R  | $R^1$ | $R^2$      | $R^3$ | $R^4$ | $R^6$ |
|-----|----|-------|------------|-------|-------|-------|
| 1   | H  | i-pr  | 3-C(O)Me   | H     | H     | H     |
| 2   | H  | 3,5-dichloropyridin-4-yl | 3-C(O)Me | H | H | H |
| 3   | H  | i-pr  | 4-n-propyl | H     | H     | H     |
| 4   | H  | i-pr  | 4-C(O)Me   | H     | H     | H     |
| 5   | H  | i-pr  | 2-Me       | H     | H     | H     |
| 6   | Me | i-pr  | 4-C(O)Me   | H     | H     | H     |
| 9   | H  | t-bu  | 4-C(O)Me   | H     | H     | H     |

TABLE 1-continued
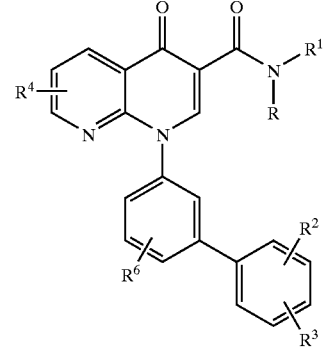
| EX. | R | R¹ | R² | R³ | R⁴ | R⁶ |
|---|---|---|---|---|---|---|
| 11 | H | i-pr | 4- 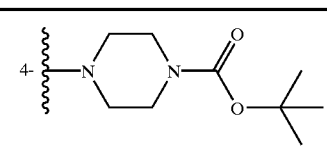 | H | H | H |
| 16 | H | c-pr | 4-CH₂OH | H | H | H |
| 18 | H | c-pr | 4-SEt | H | H | H |
| 20 | H | c-pr | 4-SO₂NH₂ | H | H | H |
| 21 | H | i-pr | 3-OEt | H | H | H |
| 22 | H | i-pr | 4-SMe | H | H | H |
| 23 | H | i-pr | 3-C(O)Me | 4-OH | H | H |
| 49 | H | i-pr | 4-SO₂Me | H | H | H |
| 52 | H | c-pr | 4-SO₂Et | H | H | H |
| 53 | H | c-pr | 4-S(O)Et | H | H | H |
| 54 | H | i-pr | 4-C(=NOH)Me | H | H | H |
| 55 | H | i-pr | 4- 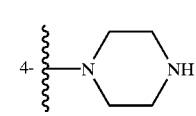 | H | H | H |
| 56 | H | c-pr | 4-CH₂SO₂Me | H | H | H |
TABLE 2
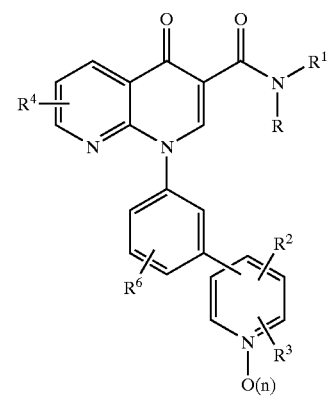
| EX. | R | R¹ | π-Position | R² | R³ | R⁴ | R⁶ | n |
|---|---|---|---|---|---|---|---|---|
| 7 | H | i-pr | 3 | H | H | H | H | 0 |

TABLE 2-continued

| EX. | R | R¹ | π-Position | R² | R³ | R⁴ | R⁶ | n |
|---|---|---|---|---|---|---|---|---|
| 10 | H | 3,5-dichloropyridin-4-yl | 3 | H | H | H | H | 0 |
| 14 | H | c-pr | 3 | H | H | H | H | 0 |
| 15 | H | i-pr | 3 | 5-SMe | H | H | H | 0 |
| 17 | H | c-pr | 4 | H | H | H | H | 0 |
| 24 | H | i-pr | 3 | 5-COOEt | H | H | H | 0 |
| 25 | H | i-pr | 3 | 5-CMe₂OH | H | H | H | 0 |
| 26 | H | i-pr | 3 | 6-CH₂CHMe₂ | H | H | H | 0 |
| 27 | H | i-pr | 3 | 5-C(O)Me | H | H | H | 0 |
| 28 | H | i-pr | 3 | 6-Me | H | H | H | 0 |
| 30 | H | H | 3 | 6-CMe₂OH | H | H | H | 1 |
| 32 | H | c-pr | 3 | 5-SO₂Me | H | H | H | 0 |
| 33 | H | c-pr | 2 | 4-CMe₂OH | H | H | H | 1 |
| 34 | H | c-pr | 2 | 5-CMe₂OH | H | H | H | 0 |
| 35 | H | c-pr | 4 | 3-CMe₂OH | H | H | H | 0 |
| 36 | H | c-pr | 4 | 3-CMe₂OH | H | H | H | 1 |
| 37 | H | c-pr | 3 | 6-SO₂I-pr | H | H | H | 0 |
| 38 | H | c-pr | 3 | 6-OMe | H | H | H | 0 |
| 39 | H | c-pr | 3 | 6-Me | H | H | H | 0 |
| 40 | H | c-pr | 3 | 6-OCH₂CF₃ | H | H | H | 0 |
| 41 | H | c-pr | 3 | 5-Br | H | H | H | 0 |
| 42 | H | c-pr | 3 | 6-OCH₂Ph | H | H | H | 0 |
| 43 | H | c-pr | 3 | 6-C(c-pr)₂OH | H | H | H | 0 |
| 44 | H | c-pr | 2 | 5-CMe₂OH | H | H | H | 1 |
| 45 | H | c-pr | 3 | 6-CMe₂OH | H | H | H | 0 |
| 46 | H | i-butyl | 3 | 6-CMe₂OH | H | H | H | 0 |
| 47 | H | c-pr | 3 | 6-CMe₂OH | H | H | 5-Br | 0 |
| 48 | H | c-pr | 2 | 6-CMe₂OH | H | H | H | 0 |
| 50 | H | c-pr | 3 | 6-SO₂Me | H | H | H | 0 |
| 51 | H | i-pr | 3 | 5-SO₂Me | H | H | H | 0 |
| 59 | H | i-pr | 3 | H | H | H | H | 1 |
| 60 | H | 3,5-dichloropyridin-4-yl | 3 | H | H | H | H | 1 |
| 61 | H | i-pr | 3 | 5-COOEt | H | H | H | 1 |
| 62 | H | i-pr | 3 | 5-CMe₂OH | H | H | H | 1 |
| 63 | H | i-pr | 3 | 6-CH₂CHMe₂ | H | H | H | 1 |
| 64 | H | i-pr | 3 | 6-Me | H | H | H | 1 |
| 65 | H | c-pr | 3 | H | H | H | H | 1 |
| 66 | H | c-pr | 3 | 6-CMe₂OH | H | H | H | 1 |
| 67 | H | c-pr | 4 | H | H | H | H | 1 |
| 68 | H | c-pr | 3 | 5-Br | H | H | H | 1 |

TABLE 2-continued
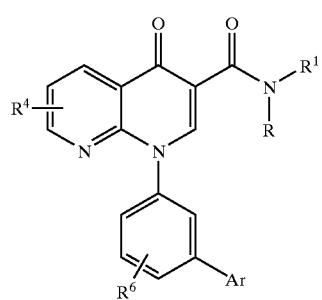
| EX. | R | R¹ | π-Position | R² | R³ | R⁴ | R⁶ | n |
|---|---|---|---|---|---|---|---|---|
| 73 | H | i-butyl | 3 | 6-CMe₂OH | H | H | H | 1 |
| 74 | H | c-pr | 3 | 6-Me | H | H | H | 1 |
| 75 | H | c-pr | 3 | 6-SO₂Me | H | H | H | 1 |
| 76 | H | c-pr | 3 | 6-CMe₂OH | H | H | 5-Br | 1 |
| 77 | H | c-pr | 3 | 6-CMe(CH2OH)OH | H | H | H | 1 |
TABLE 3
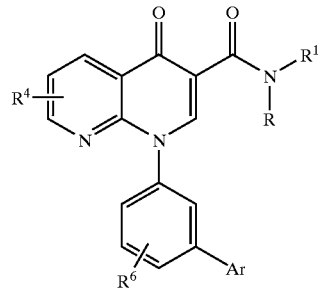
| Example | R | R¹ | Ar | R⁴ | R⁶ |
|---|---|---|---|---|---|
| 8 | H | i-pr | indol-5-yl | H | H |
| 12 | H | i-pr | quinolin-3-yl | H | H |
| 13 | H | i-pr | pyrimidin-5-yl | H | H |
| 19 | H | c-pr | 3-thienyl | H | H |
| 29 | H | c-pr | 1-oxidopyrimidin-5-yl | H | H |
TABLE 3-continued
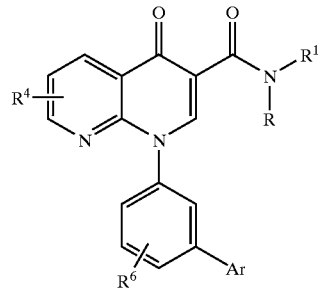
| Example | R | R¹ | Ar | R⁴ | R⁶ |
|---|---|---|---|---|---|
| 57 | H | c-pr | 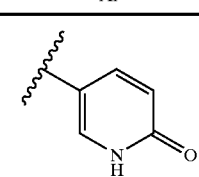 | H | H |
| 72 | H | i-pr | 1-oxidoquinolin-3-yl | H | H |
TABLE 4
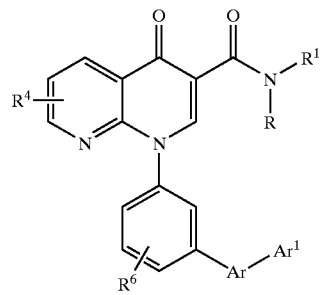

| Example | R | R¹ | Ar | Ar¹ | R⁴ | R⁶ |
|---|---|---|---|---|---|---|
| 31 | H | i-pr | Ph | 4-(pyridin-3-yl) | H | H |
| 58 | H | c-pr | Pyridin-3-yl | 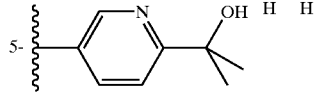 | H | H |
| 69 | H | c-pr | Pyridin-3-yl | 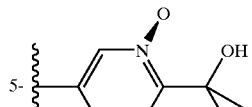 | H | H |
| 70 | H | c-pr | 1-oxidopyridin-3-yl | 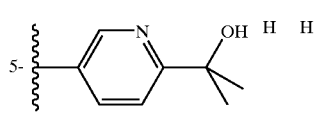 | H | H |
| 71 | H | c-pr | 1-oxidopyridin-3-yl | 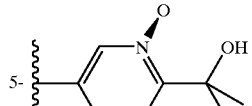 | H | H |
TABLE 5
| R¹ | R⁴ | R⁶ | Ar |
|---|---|---|---|
| c-pr | H | H | |
| c-pr | H | H | |
| i-pr | 7-Me | H | |
| i-pr | H | 5-Me | |

Example 1

N-Isopropyl-1-[3-(3-acetylphenyl)phenyl]-1,4-dihydro[1,8]naphthyridin-4-one-3-carboxamide

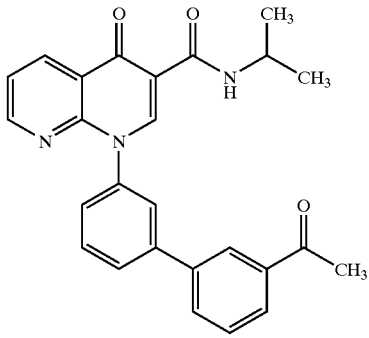

Step 1: Ethyl 3-(3-bromoanilino)-2-(2-chloronicotinoyl) acrylate.

A mixture of ethyl 2-chloronicotinoyl acetate (41.1 g, 180.5 mmol), triethyl orthoformate (40.12 g, 271 mmol) and acetic anhydride (92.05 g, 902.5 mmol) was heated at 130° C. for 2.5 hours. The volatile components were distilled off and the residue was co-evaporated twice with xylene. The oily residue was dissolved in methylene chloride (250 mL) and 3-bromoaniline (37.25 g, 216.6 mmol) was added slowly. The resulting solution was stirred at room temperature for 18 hours, and the solvent evaporated away. The resulting crude compound was used as such in the next step.

Step 2: Ethyl 1-(3-bromophenyl)-1,4-dihydro[1,8]naphthyridin-4-one-3-carboxylate.

The crude compound from Step 1 was dissolved in tetrahydrofuran (500 mL), the solution was cooled to 0° C., and sodium hydride (as a 60% dispersion in oil, 9.4 g, 235 mmol) was added in portions. After stirring at 0° for 1 hour, the mixture was allowed to warm up to room temperature. After 2 hours, water (400 mL) was added to the suspension and and the insoluble solid was filtered and washed copiously with water. When dry, the solid was stirred in ether (150 mL) at room temperature for 24 hours and filtered to afford the title compound as a cream-colored solid.

$^1$H NMR (Acetone-$d_6$) δ 1.32 (t, 3H), 4.29 (q, 2H), 7.54–7.63 (m, 2H), 7.69 (dd, 1H), 7.78 (dd, 1H), 7.93 (s, 1H), 8.66–8.71 (m, 3H).

Step 3: 1-(3-Bromophenyl)-1,4-dihydro[1,8]naphthyridin-4-one-3-carboxylic Acid

A suspension of ethyl 1-(3-bromophenyl)-1,4-dihydro[1,8]naphthyridin-4-one-3-carboxylate from Step 2 (52.5 g, 140.7 mmol) in a mixture of tetrahydrofuran (400 mL), methanol (400 mL) and 1N aqueous sodium hydroxide (280 mL) was heated at ca 50° C. with stirring for 20 minutes. After cooling, the mixture was diluted with water (300 mL) and 1N aqueous HCl (325 mL) was added. After stirring for 45 minutes, the precipitate was filtered, washed well with water and dried to afford the title acid as a cream-colored solid.

$^1$H NMR (Acetone-$d_6$) δ 7.65 (t, 1H), 7.76 (m, 2H), 7.84 (d, 1H), 7.99 (s, 1H), 8.87 (m, 2H), 9.01 (s, 1H).

Step 4: N-Isopropyl-1-(3-bromophenyl)-1,4-dihydro[1,8]naphthyridin-4-one-3-carboxamide.

To a suspension of 1-(3-bromophenyl)-1,4-dihydro[1,8]naphthyridin-4-one-3-carboxylic acid from Step 3 (26.3 g, 76 mmol) and triethylamine (23.2 g, 230 mmol) in tetrahydrofuran (1000 mL) at 0° C. was added isobutyl chloroformate (18.85 g, 138 mmol). After stirring at 0° C. for 2 hours, isopropylamine (23 g, 390 mmol) was added and the mixture was allowed to warm up to room temperature and stirred overnight. The mixture was then partitioned between ethyl acetate and water, the organic phase was dried and evaporated to a solid which was stirred in ether at room temperature for 3 hours and filtered to afford the N-Isopropyl-1-(3-bromophenyl)-1,4-dihydro[1,8]naphthyridin-4-one-3-carboxamide as a white solid.

$^1$H NMR (Acetone-$d_6$) δ 1.25 (d, 6H), 4.17 (m, 1H), 7.59–7.63 (m, 2H), 7.70 (d, 1H), 7.80 (d, 1H), 7.94 (s, 1H), 8.73 (m, 1H), 8.78 (d, 1H), 8.85 (s, 1H), 9.61 (br, NH).

Step 5: N-Isopropyl-1-[3-(3-acetylphenyl)phenyl]-1,4-dihydro[1,8]naphthyridin-4-one-3-carboxamide A mixture of N-Isopropyl-1-(3-bromophenyl)-1,4-dihydro[1,8]naphthyridin-4-one-3-carboxamide from Step 4, 3-acetylphenylboronic acid (1.2 eq.), trans-dibromobis(triphenylphosphine)palladium (II) (0.05 eq.), toluene (6 mL/mmol), ethanol (2 mL/mmol) and 2M aqueous sodium carbonate (8 eq.) was refluxed for 1 hour under a nitrogen atmosphere. The mixture was diluted with ethyl acetate and the organic phase was washed with water and brine, dried and evaporated. The crude product was chromatographed on silica gel eluting with a gradient of 20–40% ether in methylene chloride to afford the N-Isopropyl-1-[3-(3-acetylphenyl)phenyl]-1,4-dihydro[1,8]naphthyridin-4-one-3-carboxamide product as a solid.

$^1$H NMR (CDCl$_3$) δ 1.29 (d, 6H), 2.65 (s, 3H), 4.28 (m, 1H), 7.47 (m, 2H), 7.55 (t, 1H), 7.65 (m, 2H), 7.80 (m, 2H), 7.95 (dd, 1H), 8.19 (brs, 1H), 8.70 (dd, 1H), 8.81 (dd, 1H), 9.05 (s, 1H), 9.65 (br, NH).

Example 2

N-(2,6-Dichloropyridin-4-yl)-1-[3-(3-acetylphenyl)phenyl]-1,4-dihydro[1,8]naphthyridin-4-one-3-carboxamide

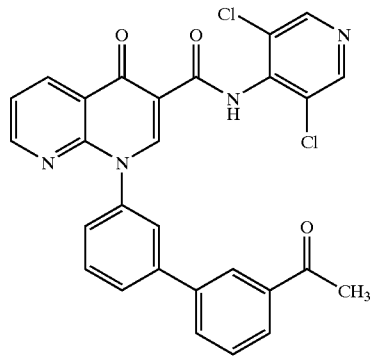

Step 1: Anion of 4-Amino-3,5-Dichloropyridine.

A suspension of sodium hydride as 60% dispersion in oil (360 mg, 9 mmol) in tetrahydrofuran (15 mL) was cooled to 0° C. A solution of 4-amino-3,5-dichloropyridine (978 mg, 6 mmol) in tetrahydrofuran (15 mL) was added slowly. The resulting mixture was kept at 0° for 2.5 hours.

Step 2: Acid Chloride of 1-(3-bromophenyl)-1,4-dihydro[1,8]naphthyridin-4-one-3-carboxylic Acid.

A suspension of 1-(3-bromophenyl)-1,4-dihydro[1,8]naphthyridin-4-one-3-carboxylic acid from Step 3 of Example 1 (690 mg, 2 mmol) in tetrahydrofuran (12 mL) was cooled to 0° C., and oxalyl chloride (381 mg, 3 mmol) was added, followed by 2 drops of N,N-dimethylformamide. The resulting mixture was then stirred at room temperature for 1 hour then refluxed for 45 minutes and cooled to room temperature.

Step 3: N-(2,6-Dichloropyridin-4-yl)-1-(3-bromophenyl)-1,4-dihydro[1,8]naphthyridin-4-one-3-carboxamide.

The mixture from Step 2 above, as a brown suspension, was added via syringe to the cold suspension of Step 1. The resulting mixture was stirred at room temperature for 18 hours, quenched with aqueous saturated ammonium chloride solution and partitioned between ethyl acetate and water. The crude product from evaporation of the organic phase was triturated with ether (50 mL) and filtered, affording the N-(2,6-Dichloropyridin-4-yl)-1-(3-bromophenyl)-1,4-dihydro[1,8]naphthyridin-4-one-3-carboxamide as a beige solid.

$^1$H NMR (Acetone-$d_6$) δ 7.61–7.70 (m, 2H), 7.76 (d, 1H), 7.81 (d, 1H), 8.00 (s, 1H), 8.62 (s, 2H), 8.80 (br s, 1H), 8.86 (d, 1H), 8.99 (s, 1H), 12.1 (br, NH).

Step 4: N-(2,6-Dichloropyridin-4-yl)-1-[3-(3-acetylphenyl)phenyl]-1,4-dihydro[1,8]naphthyridin-4-one-3-carboxamide.

Following the procedure of Step 5 of Example 1, but substituting N-(2,6-dichloropyridin-4-yl)-1-(3-bromophenyl)-1,4-dihydro[1,8]naphthyridin-4-one-3-carboxamide from step 3 for N-isopropyl 1-(3-bromophenyl)-1,4-dihydro[1,8]naphthyridin-4-one-3-carboxamide, the N-(2,6-Dichloropyridin-4-yl)-1-[3-(3-acetylphenyl)phenyl]-1,4-dihydro[1,8]naphthyridin-4-one-3-carboxamide compound was obtained as a solid.

$^1$H NMR (CDCl$_3$) δ 2.65 (s, 3H), 7.47 (d, 1H), 7.50–7.60 (m, 2H), 7.70 (m, 2H), 7.82 (d, 2H), 7.98 (d, 1H), 8.20 (s, 1H), 8.55 (s, 2H) 8.75 (brs, 1H), 8.92 (dd, 1H), 9.14 (s, 1H), 12.08 (br, NH).

Example 3

N-Isopropyl-1-[3-(4-n-propylphenyl)phenyl]-1,4-dihydro[1,8]naphthyridin-4-one-3-carboxamide

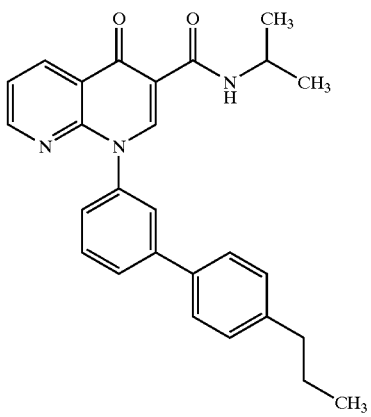

Following the procedure of Step 5 of Example 1, but substituting 4-n-propylphenylboronic acid for 3-acetylphenylboronic acid the title compound was obtained as a white solid.

$^1$H NMR (Acetone-$d_6$) δ 0.93 (t, 3H), 1.24 (d, 6H), 1.65 (m, 2H), 2.62 (t, 2H), 4.18 (m, 1H), 7.31 (d, 2H), 7.58–7.61 (m, 2H), 7.68–7.72 (m, 3H), 7.87 (d, 1H), 7.95 (s, 1H), 8.72 (m, 1H), 8.78 (dd, 1H), 8.92 (s, 1H), 9.66 (br, NH).

Example 4

N-Isopropyl-1-[3-(4-acetylphenyl)phenyl]-1,4-dihydro[1,8]naphthyridin-4-one-3-carboxamide

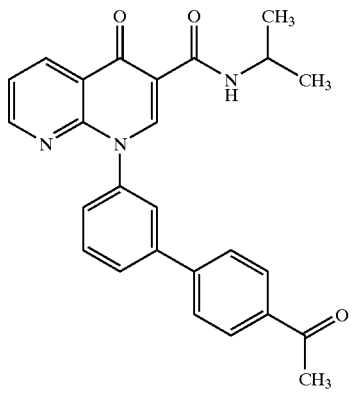

Following the procedure of Step 5 of Example 1, but substituting 4-acetylphenylboronic acid for 3-acetylphenylboronic acid the title compound was obtained as a solid.

$^1$H NMR (Acetone-$d_6$) δ 1.25 (d, 6H), 2.61 (s, 3H), 4.17 (m, 1H), 7.59 (m, 1H), 7.70 (d, 1H), 7.76 (t, 1H), 7.92 (d, 2H), 7.97 (d, 1H), 8.07–8.10 (m, 3H), 8.72 (brs, 1H), 8.78 (dd, 1H), 8.92 (s, 1H), 9.65 (br, NH).

Example 5

N-Isopropyl-1-[3-(2-methylphenyl)phenyl]-1,4-dihydro[1,8]naphthyridin-4-one-3-carboxamide

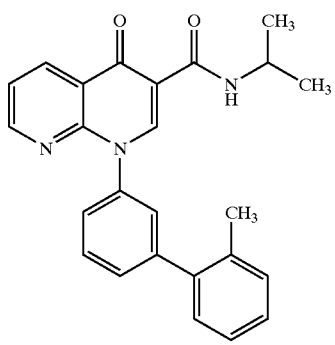

Following the procedure of Step 5 of Example 1, but substituting 2-methylphenylboronic acid for 3-acetylphenylboronic acid the title compound was obtained as a solid.

$^1$H NMR (Acetone-$d_6$) δ 1.24 (d, 6H), 2.35 (s, 3H), 4.17 (m, 1H), 7.27–7.34 (m, 4H), 7.56–7.60 (m, 2H), 7.65 (m, 2H), 7.70 (t, 1H), 8.74 (m, 1H), 8.78 (dd, 1H), 8.92 (s, 1H), 9.64 (br, NH).

Example 6

N-Isopropyl-N-methyl-1-[3-(4-acetylphenyl)phenyl]-1,4-dihydro[1,8]naphthyridin-4-one-3-carboxamide

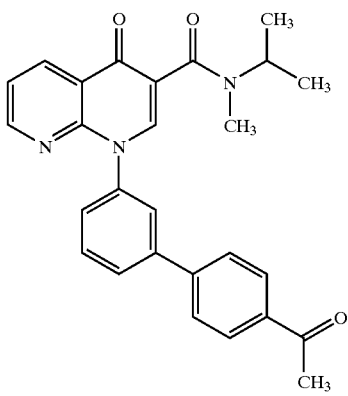

Step 1: N-Isopropyl-N-methyl-1-(3-bromophenyl)-1,4-dihydro[1,8]naphthyridin-4-one-3-carboxamide Following the procedure of Example 1, Step 4, but substituting N-isopropyl-N-methylamine for isopropylamine the N-Isopropyl-N-methyl-1-(3-bromophenyl)-1,4-dihydro[1,8]naphthyridin-4-one-3-carboxamide was obtained in as a yellow solid.

$^1$H NMR (Acetone-$d_6$) (Appears as two rotamers of the amide) δ 1.18 (m, 6H), 2.85 (s, 3H), 4.05 (m, 0.5H), 4.84 (m, 0.5H), 7.49–7.64 (m, 3H), 7.72 (d, 1H), 7.86 (s, 1H), 8.14 (s, 1H), 8.65 (d, 2H).

Step 2: N-Isopropyl-N-methyl-1-[3-(4-acetylphenyl)phenyl]-1,4-dihydro[1,8]naphthyridin-4-one-3-carboxamide Following the procedure of Step 5 of Example 1, but substituting N-isopropyl-N-methyl-1-(3-bromophenyl)-1,4-dihydro[1,8]naphthyridin-4-one-3-carboxamide from step 1 for N-isopropyl 1-(3-bromophenyl)-1,4-dihydro[1,8]naphthyridin-4-one-3-carboxamide and 4-acetylphenylboronic acid for 3-acetylphenylboronic acid the N-Isopropyl-N-methyl-1-[3-(4-acetylphenyl)phenyl]-1,4-dihydro[1,8]naphthyridin-4-one-3-carboxamide compound was obtained as a white solid.

$^1$H NMR (CDCl$_3$) (Appears as two rotamers of the amide) δ 1.23 (m, 6H), 2.62 (s, 3H), 4.00 (m, 0.5H), 4.92 (m, 0.5H), 7.38–7.55 (m, 2H), 7.63–7.77 (m, 5H), 8.03 (d, 2H), 8.14 (s, 0.5H), 8.21 (s, 0.5H), 8.65 (m, 1H), 8.75–8.80 (m, 1H).

Example 7

N-Isopropyl-1-[3-(pyridin-3-yl)phenyl]-1,4-dihydro[1,8]naphthyridin-4-one-3-carboxamide

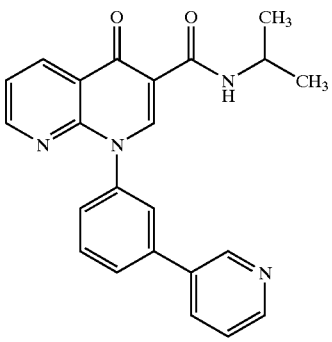

Following the procedure of Step 5 of Example 1, but substituting pyridine-3-boronic acid 1,3-propanediol cyclic ester for 3-acetylphenylboronic acid and [1,1'-bis(diphenylphosphino)ferrocene]dichloropalladium(II) for trans-dibromobis(triphenylphosphine)palladium (II) the title compound was obtained as a beige solid.

$^1$H NM (Acetone-$d_6$) δ 1.24 (d, 6H), 4.17 (m, 1H), 7.48 (m, 1H), 7.60 (m, 1H), 7.71 (dd, 1H), 7.78 (t, 1H), 7.95 (dd, 1H), 8.05 (brs, 1H), 8.15 (m, 1H), 8.60 (m, 1H), 8.72 (m, 1H), 8.78 (dd, 1H), 8.92 (s, 1H), 8.99 (brs, 1H), 9.65 (br, NH).

EXAMPLE 8

N-Isopropyl-1-[3-(indol-5-yl)phenyl]-1,4-dihydro[1,8]naphthyridin-4-one-3-carboxamide

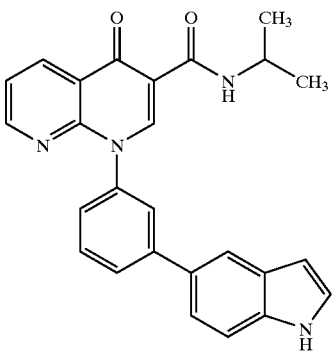

Following the procedure of Step 5 of Example 1, but substituting 5-indolylboronic acid for 3-acetylphenylboronic acid the title compound was obtained as an off-white solid.

$^1$H NMR ((DMSO-$d_6$) δ 1.20 (d, 6H), 4.10 (m, 1H), 6.47 (s, 1H), 7.38 (brs, 1H), 7.46–7.52 (m, 3H), 7.59–7.66 (m, 2H), 7.87–7.93 (m, 3H), 8.72–8.81 (m, 3H), 9.67 (br, NH), 11.2 (br, NH).

Example 9

N-tert-Butyl-1-[3-(4-acetylphenyl)phenyl]-1,4-dihydro[1,8]naphthyridin-4-one-3-carboxamide

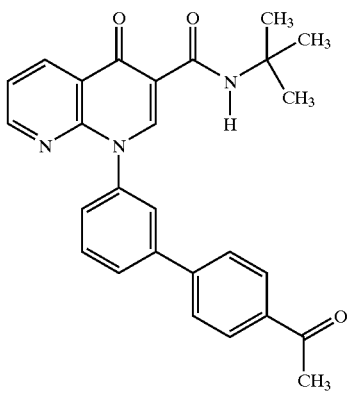

Step 1: N-tert-Butyl-1-(3-bromophenyl)-1,4-dihydro[1,8]naphthyridin-4-one-3-carboxamide Following the procedure of Example 1, Step 4, but substituting tert-butylamine for isopropylamine the N-tert-Butyl-1-(3-bromophenyl)-1,4-dihydro[1,8]naphthyridin-4-one-3-carboxamide was obtained as a yellow solid.

$^1$H NMR (Acetone-$d_6$) δ 1.44 (s, 9H), 7.58–7.62 (m, 2H), 7.70 (dd, 1H), 7.78 (dd, 1H), 7.93 (br s, 1H), 8.72 (m, 1H), 8.77 (dd, 1H), 8.81 (s, 1H), 9.73 (br, NH).

Step 2: N-tert-Butyl-1-[3-(4-acetylphenyl)phenyl]-1,4-dihydro[1,8]naphthyridin-4-one-3-carboxamide Following the procedure of Step 5 of Example 1, but substituting N-tert butyl-1-(3-bromophenyl)-1,4-dihydro[1,8]naphthyridin-4-one-3-carboxamide from step 1 for N-isopropyl 1-(3-bromophenyl)-1,4-dihydro[1,8]naphthyridin-4-one-3-carboxamide and 4-acetylphenylboronic acid for 3-acetylphenylboronic acid the N-tert-Butyl-1-[3-(4-acetylphenyl)phenyl]-1,4-dihydro[1,8]naphthyridin-4-one-3-carboxamide compound was obtained in 93% yield as a white solid.

$^1$H NMR (Acetone-$d_6$) δ 1.45 (s, 9H), 2.61 (s, 3H), 7.59 (m, 1H), 7.69–7.72 (m, 1H), 7.77 (t, 1H), 7.92–7.99 (m, 3H), 8.07–8.11 (m, 3H), 8.72 (m, 1H), 8.78 (dd, 1H), 8.91 (s, 1H), 9.79 (br, NH).

Example 10

N-(2,6-Dichloropyridin-4-yl)-1-[3-(pyridin-3-yl)phenyl]-1,4-dihydro[1,8]naphthyridin-4-one-3-carboxamide

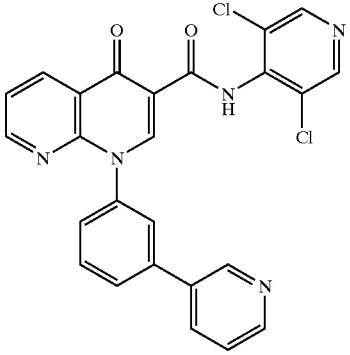

Following the procedure of Step 4 of Example 2 but substituting [1,1'-bis (diphenylphosphino)ferrocene]dichloropalladium(II) for trans-dibromobis(triphenylphosphine)palladium (II) and pyridine-3-boronic acid 1,3-propanediol cyclic ester for 3-acetylphenylboronic acid the title compound was obtained as a glassy solid.

H NMR (Acetone-$d_6$) δ 7.48 (m, 1H), 7.68 (m, 1H), 7.77–7.82 (m, 2H), 7.98 (m, 1H), 8.12–8.17 (m, 2H), 8.61 (m, 1H), 8.62 (s, 2H), 8.80 (m, 1H), 8.88 (dd, 1H), 8.99 (brs, 1H), 9.06 (s, 1H), 12.2 (br, NH).

Example 11

N-Isopropyl-1-{3-[4-(4-tertbutyloxycarbonylpiperazin-1-yl)phenyl]-phenyl}-1,4-dihydro[1,8]naphthyridin-4-one-3-carboxamide

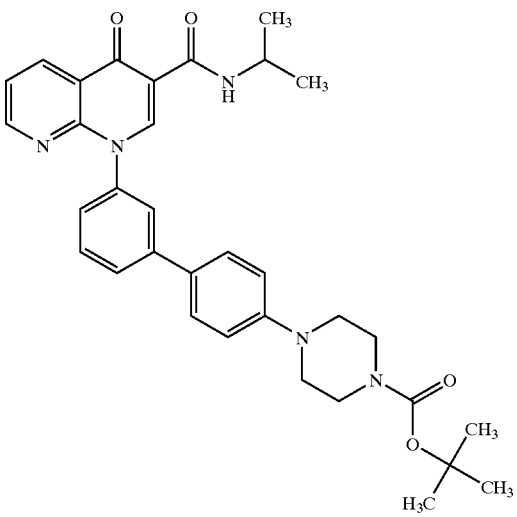

Step 1: 4-tert-Butyloxycarbonyl-1-(3-bromophenyl)piperazine

To a suspension of 1-(4-bromophenyl)piperazine hydrochloride (103.15 g, 371.59 mmol) in acetonitrile (1.5 L) at 0° C. under a nitrogen atmosphere was added a catalytic amount of 4-dimethylaminopyridine (4.54 g, 37.159 mmol) followed by triethylamine (155 mL, 1114.77 mmol) and di-tert-butyl dicarbonate (121.65 g, 557.385 mmol, dissolved in a minimum amount of acetonitrile) and the resulting reaction mixture was warmed to room temperature and stirred for 5.5 hours. The reaction mixture was filtered, ethyl acetate was added and the organic phase was washed with 10% aqueous citric acid, water (2×) and brine, then dried and evaporated to afford the crude 4-tert-Butyloxycarbonyl-1-(3-bromophenyl)piperazine product which was used as such in the next step.

Step 2: 3-(4-tert-Butyloxycarbonylpiperazin-1-yl)phenylboronic Acid

To the 4-tert-Butyloxycarbonyl-1-(3-bromophenyl)piperazine from Step 1 (118.30 g, 346.9 mmol) in tetrahydrofuran/toluene (1/1, 1.5 L) at −78° C. under nitrogen was added n-butyllithium (2.5M, 160 mL, 398.9 mmol) dropwise and the resulting reaction mixture was stirred at −78° C. for 20 minutes. Triisopropyl borate (96.1 mL, 416.3 mmol) was added dropwise and the reaction was warmed to 0° C. and stirred for 2 hours. Aqueous saturated ammonium chloride (400 mL), water (100 mL) and 1 equivalent of $H_3PO_4$ (20 mL) were added and the mixture was stirred for 15 minutes and then concentrated to a volume of approximately 200 mL (at which stage the mixture became bluish and a precipitate formed). The mixture was slowly diluted with heptane (800 mL) and the resulting suspension was stirred overnight. The suspension was filtered, the solid was washed with heptane and dried to afford the title boronic acid.

Step 3: N-Isopropyl-1-{3-[4-(4-tertbutyloxycarbonylpiperazin-1-yl)phenyl]-phenyl}-1,4-dihydro[1,8]naphthyridin-4-one-3-carboxamide Following the procedure of Step 5 of Example 1 but substituting [1,1'-bis (diphenylphosphino)ferrocene] dichloropalladium(II) for trans-dibromobis(triphenylphosphine)palladium (II) and the boronic acid from Step 2 above for 3-acetylphenylboronic acid the 4-tert-Butyloxycarbonyl-1-(3-bromophenyl)piperazine compound was obtained as a solid.

$^1$H NMR (CDCl$_3$) δ 1.30 (d, 6H), 1.49 (s, 9H), 3.18 (m, 4H), 3.58 (m, 4H), 4.29 (m, 1H), 6.98 (d, 2H), 7.32 (d, 1H), 7.45 (in, 1H), 7.53 (d, 2H), 7.55–7.62 (m, 2H), 7.72 (d, 1H), 8.70 (m, 1H), 8.82 (d, 1H), 9.07 (s, 1H), 9.68 (br, NH).

Example 12

N-Isopropyl-1-[3-(quinolin-3-yl)phenyl]-1,4-dihydro[1,8]naphthyridin-4-one-carboxamide

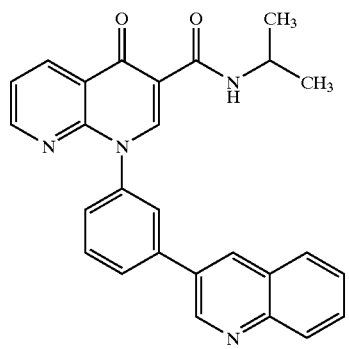

Following the procedure of Step 5 of Example 1, but substituting 3-quinolineboronic acid for 3-acetylphenylboronic acid the title compound was obtained as a solid.

$^1$H NMR (CDCl$_3$) δ 1.29 (d, 6H), 4.29 (m, 1H), 7.49 (m, 2H), 7.61 (t, 1H), 7.70–7.78 (m, 3H), 7.86–7.92 (m, 2H), 8.14 (d, 1H), 8.36 (s, 1H), 8.71 (m, 1H), 8.84 (dd, 1H), 9.10 (s, 1H), 9.19 (s, 11H), 9.67 (br, NH).

Example 13

N-Isopropyl-1-[3-(pyrimidin-5-yl)phenyl]-1,4-dihydro[1,8]naphthyridin-4-one-carboxamide

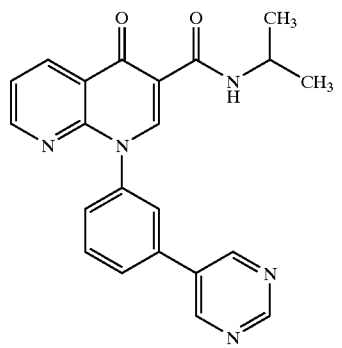

Following the procedure of Step 5 of Example 1, but substituting 5-pyrimidineboronic acid for 3-acetylboronic acid the title compound was obtained as a solid.

$^1$H NMR (CDCl$_3$) δ 1.28 (d, 6H), 4.27 (m, 1H), 7.48 (dd, 1H), 7.52 (m, 1H), 7.65 (s, 1H), 7.74 (m, 2H), 8.68 (m, 1H), 8.72 (d, 1H), 8.98 (s, 2H) 9.03 (s, 1H), 9.22 (s, 1H), 9.62 (br, NH).

Example 14

N-Cyclopropyl-1-[3-(pyridin-3-yl)phenyl]-1,4-dihydro[1,8]naphthyridin-4-one-3-carboxamide

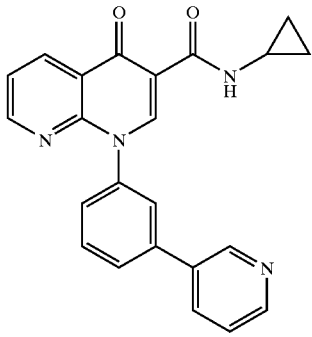

Step 1: N-Cyclopropyl-1-(3-bromophenyl)-1,4-dihydro[1,8naphthyridin-4-one-3-carboxamide Following the procedure of Example 1, Step 4, but substituting cyclopropylamine for isopropylamine the N-Cyclopropyl-1-(3-bromophenyl)-1,4-dihydro[1,8]naphthyridin-4-one-3-carboxamide was obtained as a fluffy white solid.

$^1$H NMR (Acetone-d$_6$) δ 0.59 (m, 2H), 0.80 (m, 2 h), 2.96 (m, 1H), 7.59–7.68 (m, 2H), 7.72 (dd, 1H), 7.82 (dd, 1H), 7.97 (s, 1H), 8.72–8.81 (m, 2H), 8.89 (s, 1H), 9.70 (br, NH).

Step 2: N-Cyclopropyl-1-[3-(pyridin-3-yl)phenyl]-1,4-dihydro[8]naphthyridin-4-one-3-carboxamide Following the procedure of Example 7 but substituting N-cyclopropyl-1-(3-bromophenyl)-1,4-dihydro[1,8]naphthyridin-4-one-3-carboxamide from step 1 for N-isopropyl-1-(3-bromophenyl)-1,4-dihydro[1,8]naphthyridin-4-one-3-carboxamide, the N-Cyclopropyl-1-[3-(pyridin-3-yl)phenyl]-1,4-dihydro[1,8]naphthyridin-4-one-3-carboxamide compound was obtained as a cream-coloured solid.

$^1$H NMR (DMSO-d$_6$) δ 0.57 (m, 2H), 0.78 (m, 2H), 2.91 (m, 1H), 7.52 (m, 1H), 7.63–7.69 (m, 2H), 7.74 (t, 1H), 7.97 (d, 1H), 8.07 (brs, 1H), 8.17 (d, 1H), 8.61 (m, 1H), 8.73 (dd, 1H), 8.79 (m, 1H), 8.85 (s, 1H), 8.99 (brs, 1H), 9.74 (br, NH).

Example 15

N-Isopropyl-1-[3-(5-methylthiopyridin-3-yl)phenyl]-1,4-dihydro[1,8]naphthyridin-4-one-3-carboxamide

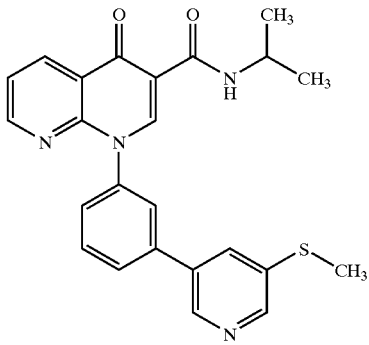

Following the procedure of Step 5 of Example 1 but substituting 5-methylthiopyridine-3-boronic acid for 3-acetylphenylboronic acid and [1,1'-bis(diphenylphosphino)ferrocene]dichloropalladium(II) for trans-dibromobis(triphenylphosphine)palladium (II) the title compound was obtained as a solid.

$^1$H NMR (CDCl$_3$) δ 1.33 (d, 6H) 2.60 (s, 3H), 4.33 (m, 1H), 7.48–7.54 (m, 2H), 7.66 (m, 1H), 7.73 (t, 1H), 7.78–7.81 (m, 2H), 8.55 (s, 1H), 8.66 (s, 1H), 8.74 (m, 1H), 8.87 (d, 1H), 9.09 (s, 1H), 9.69 (br, NH).

Example 16

N-Cyclopropyl-1-[3-(4-hydroxymethylphenyl)phenyl]-1,4-dihydro[1,8]naphthyridin-4-one-3-carboxamide

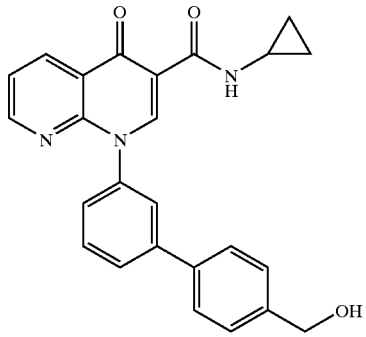

Following the procedure of Step 2 of Example 14 but substituting 4-hydroxymethylphenyl boronic acid for pyridine-3-boronic acid 1,3-propanediol cyclic ester the title compound was obtained as a solid.

$^1$H NMR (CDCl$_3$) δ 0.71 (m, 2H), 0.89 (m, 2H), 1.88 (t, 1H), 3.03 (m, 1H), 4.78 (d, 2H), 7.43 (d, 1H), 7.46–7.52 (m, 3H), 7.61–7.69 (m, 4H), 7.80 (d, 1H), 8.73 (m, 1H), 8.83 (dd, 1H), 9.10 (s, 1H), 9.82 (br, NH).

Example 17

N-Cyclopropyl-1-[3-(pyridin-4-yl)phenyl]-1,4-dihydro[1,8]naphthyridin-4-one-3-carboxamide

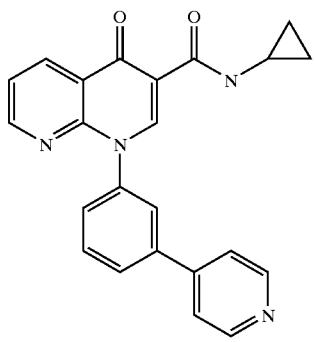

Following the procedure of Step 5 of Example 1 but substituting N-cyclopropyl-1-(3-bromophenyl)-1,4-dihydro[1,8]naphthyridin-4-one-3-carboxamide for N-isopropyl-1-(3-bromophenyl)-1,4-dihydro[1,8]naphthyridin-4-one-3-carboxamide and 4-pyridineboronic acid for 3-acetylphenylboronic acid the title compound was obtained as a white solid.

$^1$H NMR ((DMSO-d$_6$) δ 0.57 (m, 2H), 0.77 (m, 2H), 2.90 (m, 1H), 7.64 (m, 1H), 7.72–7.89 (m, 4H), 8.03 (d, 1H), 8.13 (s, 1H), 8.66–8.78 (m, 4H), 8.84 (s, 1H), 9.72 (br, NH).

Example 18

N-Cyclopropyl-1-[3-(4-ethylthiophenyl)phenyl]-1,4-dihydro[1,8]naphthyridin-4-one-3-carboxamide

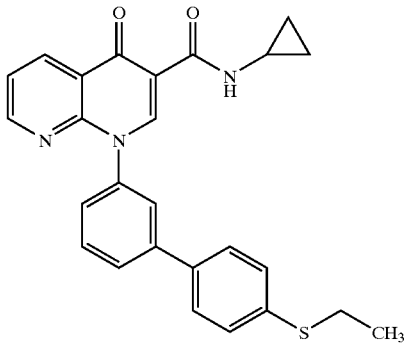

Following the procedure of Step 2 of Example 14 but substituting 4-ethylthiobenzeneboronic acid for pyridine-3-boronic acid 1,3-propanediol cyclic ester the title compound was obtained as a solid.

$^1$H NMR (CDCl$_3$) δ 0.72 (m, 2H), 0.90 (m, 2H), 1.48 (t, 3H), 3.03 (m, 3H), 7.42 (d, 3H), 7.50 (m, 1H), 7.57 (d, 2H), 7.64 (s, 1H), 7.68 (t, 1H), 7.78 (d, 1H), 8.75 (m, 1H), 8.85 (d, 1H), 9.10 (s, 1H), 9.83 (br, NH).

Example 19

N-Cyclopropyl-1-[3-(3-thienyl)phenyl]-1,4-dihydro[1,8]naphthyridin-4-one-3-carboxamide

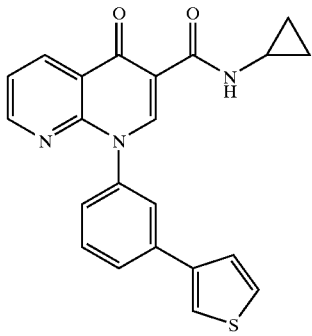

Following the procedure of Step 2 of Example 14 but substituting 3-thiopheneboronic acid for pyridine-3-boronic acid 1,3-propanediol cyclic ester the title compound was obtained as a white solid.

$^1$H NMR (Acetone-d$_6$) δ 0.60 (m, 2H), 0.79 (m, 2H), 2.96 (m, 1H), 7.57–7.72 (m, 5H), 7.92–7.98 (m, 2H), 8.05 (s, 1H), 8.74 (s, 1H), 8.78 (d, 1H), 8.93 (s, 1H), 9.74 (br, NH).

Example 20

N-Cyclopropyl-1-[3-(4-sulfamoylphenyl)phenyl]-1,4-dihydro[1,8]naphthyridin-4-one-3-carboxamide

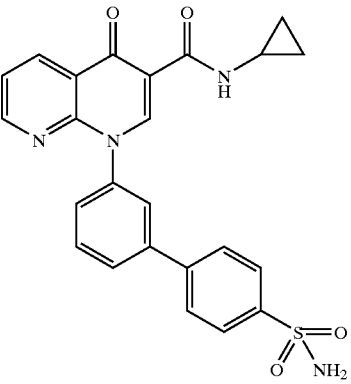

Step 1: 4-Sulfamoylbenzeneboronic Acid Pinacol Ester

A mixture of 4-bromobenzenesulfonamide, diboron pinacol ester (1.1 eq), potassium acetate (3.5 eq) and 1,1'-bis(diphenylphosphino)ferrocene]dichloropalladium(II) (0.05 eq) im N,N-dimethylformamide (4 ml/mmol) was heated at 85° C. for 18 hours. After quenching with saturated aqueous ammonium chloride solution the mixture was partitioned between ethyl acetate and water and the product from the organic phase was chromatographed on silica gel eluting with a 1:1 mixture of ethyl acetate and hexane to afford the 4-Sulfamoylbenzeneboronic acid pinacol ester as a solid.

Step 2: N-Cyclopropyl-1-[3-(4-sulfamoylphenyl)phenyl]-1,4-dihydro[1,8]naphthyridin-4-one-3-carboxamide A mixture of N-cyclopropyl-1-(3-bromophenyl)-1,4-dihydro[1,8]naphthyridin-4-one-3-carboxamide, boronate from Step 1 (1.2 eq), palladium acetate (0.1 eq), triphenylphosphine (0.35 eq) and 2M aqueous sodium carbonate (3.5 eq) in n-propanol (10 ml/mmol) was stirred at 85° C. for 1 hour. After cooling, the mixture was quenched with saturated aqueous ammonium chloride solution and partitioned between ethyl acetate and water, and the product from the organic phase was chromatographed on silica gel eluting with a 1:5:4 mixture of ethanol, ethyl acetate and methylene chloride to afford the N-Cyclopropyl-1-[3-(4-sulfamoylphenyl)phenyl]-1,4-dihydro[1,8]naphthyridin-4-one-3-carboxamide compound as a solid.

$^1$H NMR (Acetone-d$_6$) δ 0.62 (m, 2H), 0.82 (m, 2H), 2.98 (m, 1H), 6.66 (br, NH$_2$), 7.64 (m, 1H), 7.74 (m, 1H), 7.80 (t, 1H), 7.97–8.05 (m, 5H), 8.10 (m, 1H), 8.76 (m, 1H), 8.81 (dd, 1H), 8.97 (s, 1H), 9.77 (br, NH).

Example 21

N-Isopropyl-1-[3-(3-ethoxyphenyl)phenyl]-1,4-dihydro[1,8]naphthyridin-4-one-3-carboxamide

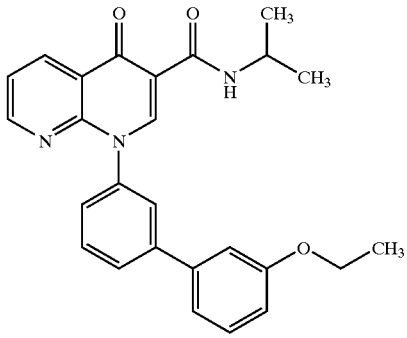

Step 1: Ethyl 1-[3-(3-ethoxyphenyl)phenyl]-1,4-dihydro[1,8]naphthyridin-4-one-3-carboxylate Following the procedure of Step 5 of Example 1, but substituting ethyl 1-(3-bromophenyl)-1,4-dihydro[1,8]naphthyridin-4-one-3-carboxylate from Step 2 of Example 1 for N-isopropyl-1-(3-bromophenyl)-1,4-dihydro[1,8]naphthyridin-4-one-3-carboxamide, and 3-ethoxybenzeneboronic acid for 3-acetylbenzeneboronic acid, the Ethyl 1-[3-(3-ethoxyphenyl)phenyl]-1,4-dihydro[1,8]naphthyridin-4-one-3-carboxylate compound was obtained as a solid.

Step 2: 1-[3-(3-Ethoxyphenyl)phenyl]-1,4-dihydro[1,8]naphthyridin-4-one-3-carboxylic Acid Following the procedure of Step 3 of Example 1 but substituting ethyl 1-[3-(3-ethoxyphenyl)phenyl]-1,4-dihydro[1,8]naphthyridin-4-one-3-carboxylate from step 1 for ethyl 1-(3-bromophenyl)-1,4-dihydro[1,8]naphthyridin-4-one-3-carboxylate the 1-[3-(3-Ethoxyphenyl)phenyl]-1,4-dihydro[1,8]naphthyridin-4-one-3-carboxylic acid compound was obtained and used without purification in the next step.

Step 3: N-Isopropyl-1-[3-(3-ethoxyphenyl)phenyl]-1,4-dihydro[1,8]naphthyridin-4-one-3-carboxamide A mixture of 1-[3-(3-ethoxyphenyl)phenyl]-1,4-dihydro[1,8]naphthyridin-4-one-3-carboxylic acid from Step 2 and thionyl chloride (4 eq) in tetrahydrofuran (10 ml/mmol) was refluxed for 45 minutes, then evaporated. The residue was dissolved in the same volume of tetrahydrofuran, isopropylamine (5 eq) was added and the mixture was stirred at room temperature for 18 hours. After quenching with saturated aqueous ammonium chloride solution, the resulting mixture was partitioned between ethyl acetate and water, and the product from the organic phase was chromatographed on silica gel eluting with 10% ether in methylene chloride to afford the N-Isopropyl-1-[3-(3-ethoxyphenyl)phenyl]-1,4-dihydro[1,8]naphthyridin-4-one-3-carboxamide compound as a solid.

$^1$H NMR (CDCl$_3$) δ 1.29 (d, 6H), 1.42 (t, 3H), 4.08 (q, 2H), 4.28 (m, 1H), 6.91 (d, 1H), 7.12 (s, 1H), 7.18 (d, 1H), 7.34 (t, 1H), 7.40 (d, 1H), 7.46 (m, 1H), 7.60–7.65 (m, 2H), 7.75 (d, 1H), 8.71 (brs, 1H), 8.82 (dd, 1H), 9.08 (s, 1H), 9,70 (br, NH).

Example 22

N-Isopropyl-1-[3-(4-methylthiophenyl)phenyl]-1,4-dihydro[1,8]naphthyridin-4-one-3-carboxamide

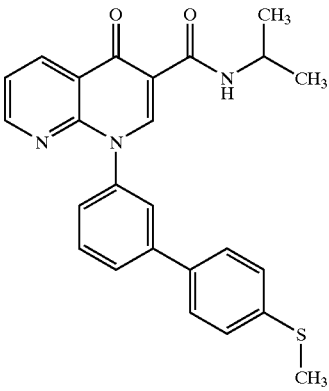

Step 1: Ethyl 1-[3-(4-methylthiophenyl)phenyl]-1,4-dihydro[1,8]naphthyridin-4-one-3-carboxylate Following the procedure of Step 5 of Example 1, but substituting ethyl 1-(3-bromophenyl)-1,4-dihydro[1,8]naphthyridin-4-one-3-carboxylate from step 2 of example 1 for N-isopropyl-1-(3-bromophenyl)-1,4-dihydro[1,8]naphthyridin-4-one-3-carboxamide, and 4-methylthiobenzeneboronic acid for 3-acetylbenzeneboronic acid, the Ethyl 1-[3-(4-methylthiophenyl)phenyl]-1,4-dihydro[1,8]naphthyridin-4-one-3-carboxylate compound was obtained as a solid.

Step 2: 1-[3-(4-methylthiophenyl)phenyl]-1,4-dihydro[1,8]naphthyridin-4-one-3-carboxylic Acid Following the procedure of Step 3 of Example 1 but substituting ethyl 1-[3-(4-methylthiophenyl)phenyl]-1,4-dihydro[1,8]naphthyridin-4-one-3-carboxylate from Step 1 for ethyl 1-(3-bromophenyl)-1,4-dihydro[1,8]naphthyridin-4-one-3-carboxylate the 1-[3-(4-methylthiophenyl)phenyl]-1,4-dihydro[1,8]naphthyridin-4-one-3-carboxylic acid compound was obtained as a solid.

Step 3: N-Isopropyl-1-[3-(4-methylthiophenyl)phenyl]-1,4-dihydro[1,8]naphthyridin-4-one-3-carboxamide Following the procedure of Step 3 of Example 21 but substituting 1-[3-(4-methylthiophenyl)phenyl]-1,4-dihydro[1,8]naphthyridin-4-one-3-carboxylic acid for 1-[3-(3-ethoxyphenyl)phenyl]-1,4-dihydro[1,8]naphthyridin-4-one-3-carboxylic acid the N-Isopropyl-1-[3-(4-methylthiophenyl)phenyl]-1,4-dihydro[1,8]naphthyridin-4-one-3-carboxamide compound was obtained as a white solid.

$^1$H NMR (Acetone-d$_6$) δ 1.24 (d, 6H), 2.52 (s, 3H), 4.18 (m, 1H), 7.37 (d, 2H), 7.58–7.62 (m, 2H), 7.69–7.73 (m, 3H), 7.87 (d, 1H), 7.96 (s, 1H), 8.72 (m, 1 H), 8.78 (dd, 1H), 8.91 (s, 1H), 9.65 (br, NH).

Example 23

N-Isopropyl-1-[3-(3-acetyl-4-hydroxyphenyl)phenyl]-1,4-dihydro[1,8]naphthyridin-4-one-3-carboxamide

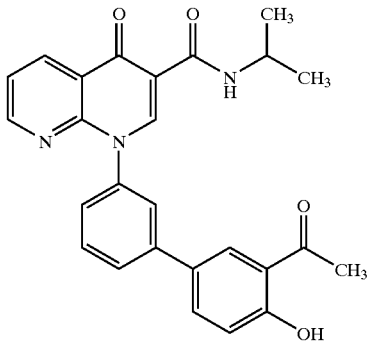

A mixture of 5'-bromo-2'-hydroxyacetophenone, diboron pinacol ester (1.25 eq), potassium acetate (3 eq) and [1,1'-bis(diphenylphosphino)ferrocene]dichloropalladium(II) (0.05 eq) in N,N-dimethylformamide (10 ml/mmol) was stirred at 80° C. for 3 hours and cooled down. A solution of N-Isopropyl-1-(3-bromophenyl)-1,4-dihydro[1,8]naphthyridin-4-one-3-carboxamide from Example 1, Step 4 (0.75 eq) in N,N-dimethylformamide (7 ml/mmol), [1,1'-bis(diphenylphosphino)ferrocene]dichloropalladium(II) (0.05 eq) and 2M aqueous sodium carbonate (8.5 eq) were added and the resulting mixture was stirred at 80° C. for 2.5 hours. The cooled mixture was partitioned between ethyl acetate and water and the product from the organic phase was chromatographed on silica gel eluting with 60% ethyl acetate in hexane to afford the title compound as a light yellow solid.

$^1$H NMR (Acetone-$d_6$) δ 1.24 (d, 6H), 2.75 (s, 3H), 4.19 (m, 1H), 7.06 (d, 1H), 7.59–7.63 (m, 2H), 7.72 (t, 1H), 7.92 (d, 1H), 7.97 (d, 1H), 8.02 (s, 1H), 8.33 (s, 1H), 8.73 (m, 1H), 8.78 (dd, 1H), 8.90 (s, 1H), 9.65 (br, NH).

Example 24

N-Isopropyl-1-[3-(5-carboethoxypyridin-3-yl)phenyl]-1,4-dihydro[1,8]naphthyridin-4-one-3-carboxamide

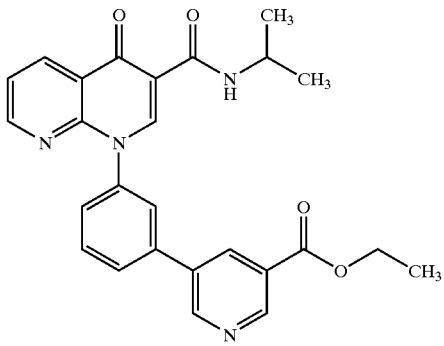

Following the procedure of Example 23 but substituting N-isopropyl-1-(3-bromophenyl)-1,4-dihydro[1,8]naphthyridin-4-one-3-carboxamide for 5'-bromo-2'-hydroxyacetophenone and ethyl 5-bromonicotinate for N-isopropyl-1-(3-bromophenyl)-1,4-dihydro[1,8]naphthyridin-4-one-3-carboxamide the title compound was obtained as a beige solid.

$^1$H NMR (CDCl$_3$) δ 1.29 (d, 6H), 1.40 (t, 3H), 4.28 (m, 1H), 4.42 (q, 2H), 7.45–7.51 (m, 2H), 7.68 (s, 1H), 7.71 (t, 1H), 7.80 (d, 1H), 8.49 (s, 1H), 8.59 (m, 1H), 8.82 (d, 1H), 9.03 (s, 1H), 9.07 (s, 1H), 9.23 (s, 1H), 9.64 (br, NH).

Example 25

N-Isopropyl-1-{3-[5-(1-hydroxy-1-methylethyl)pyridin-3-yl]phenyl}-1,4-dihydro[1,8]naphthyridin-4-one-3-carboxamide

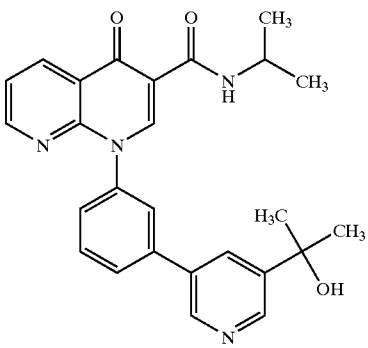

Step 1: 3-Bromo-5-(1-hydroxy-1-methylethyl)pyridine

To a solution of ethyl 5-bromonicotinate (1.02 g, 4.4 mmol) in diethyl ether (15 ml) at −30° C. was added a 3M solution of methyl magnesium bromide (4 ml, 12 mmol) in ether. The resulting slurry was then refluxed for 2 hours then cooled and quenched with an excess of 0.5M aqueous monobasic sodium phosphate and partitioned between ether and water. The product from the organic phase was chromatographed on silica gel eluting with a 2:1:2 mixture of ether, pentane and ammonia-saturated methylene chloride to afford the 3-Bromo-5-(1-hydroxy-1-methylethyl)pyridine compound as a yellow oil.

Step 2: N-Isopropyl-1-{3-[5-(1-hydroxy-1-methylethyl)pyridin-3-yl]phenyl}-1,4-dihydro[1,8]naphthyridin-4-one-3-carboxamide.

Following the procedure of Example 24, but substituting the 3-bromo-5-(1-hydroxy-1-methylethyl)pyridine from Step 1 for ethyl 5-bromonicotinate, the title compound was obtained as a yellow foam.

$^1$H NMR (CDCl$_3$) δ 1.28 (d, 6H), 1.62 (s, 6H), 2.52 (brs, 1H), 4.25 (m, 1H), 7.41–7.48 (m, 2H), 7.60–7.68 (m, 2H), 7.75 (d, 1H), 8.05 (s, 1H), 8.67–8.71 (m, 3H), 8.80 (dd, 1H), 9.03 (s, 1H), 9.66 (br, NH).

Example 26

N-Isopropyl-1-{3-[6-(2-methylpropyl)pyridin-3-yl]phenyl}-1,4-dihydro[1,8]naphthyridin-4-one-3-carboxamide

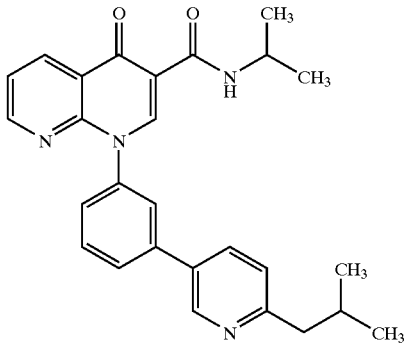

Step 1: 5-Bromo-2-(2-methylpropyl)pyridine

To a solution of 2,5-dibromopyridine (4.5 g, 19 mmol) in tetrahydrofuran (50 ml) was added [1,1'-bis(diphenylphosphino)ferrocene]dichloronickel (II) (103 mg, 0.19 mmol) and the resulting mixture was cooled to −10° C. A 2M solution of isobutylmagnesium bromide in ether (12.4 ml, 24.7 mmol) was added slowly and the mixture was stirred at −10 to 10° C for 3.5 hours. After quenching with saturated aqueous ammonium chloride solution, the mixture was partitioned between ether and water and the product from the organic phase was chromatographed on silica gel eluting with 10% ether in pentane to afford the 5-Bromo-2-(2-methylpropyl)pyridine compound as a volatile oil.

Step 2: N-Isopropyl-1-{3-[6-(2-methylpropyl)pyridin-3-yl]phenyl}-1,4-dihydro[1,8]naphthyridin-4-one-3-carboxamide Following the procedure of Example 24 but substituting 5-bromo-2-(2-methylpropyl)pyridine from Step 1 for ethyl 5-bromonicotinate the N-Isopropyl-1-{3-[6-(2-methylpropyl)pyridin-3-yl]phenyl}-1,4-dihydro[1,8]naphthyridin-4-one-3-carboxamide compound was obtained as a white solid.

$^1$H NMR (CDCl$_3$) δ 0.92 (d, 6H), 1.28 (d, 6H), 2.10 (m, 1H), 2.69 (d, 2H), 4.28 (m, 1H), 7.19 (d, 1H), 7.40–7.47 (m, 2H), 7.60 (s, 1H), 7.64 (t, 1H), 7.73 (d, 1H), 7.79 (dd, 1H), 8.68 (m, 1H), 8.77–8.83 (m, 2H), 9.05 (s, 1H), 9.66 (br, NH).

Example 27

N-Isopropyl-1-[3-(5-acetylpyridin-3-yl)phenyl]-1,4-dihydro[1,8]naphthyridin-4-one-3-carboxamide

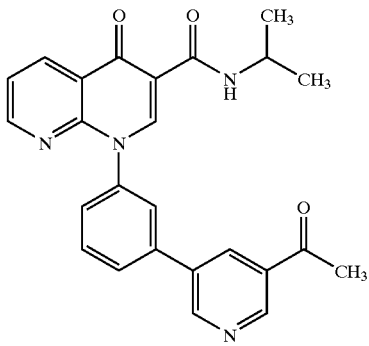

Step 1: 3-Acetyl-5-bromopyridine

To a solution of ethyl 5-bromonicotinate (3.9 g, 16.9 mmol) in ether (50 ml) at 0° C. was added a 3M solution of methylmagnesium bromide (16.9 ml, 50.8 mmol). The resulting thick slurry was warmed slowly to room temperature and after 1.5 hours it was poured slowly into an excess of 1M aqueous monobasic sodium phosphate. The mixture was partitioned between ether and water and the product from the organic phase was chromatographed on silica gel, eluting with a 1:1:2 mixture of ether, pentane and ammonia-saturated methylene chloride to afford the 3-acetyl-5-bromopyridine compound. This preparation also afforded 3-bromo-5-(1-hydroxy-1-methylethyl)pyridine described in Example 25.

Step 2: N-Isopropyl-1-[3-(5-acetlpyridin-3-yl)phenyl]-1,4-dihydro[1,8]naphthyridin-4-one-3-carboxamide Following the procedure of Example 23 but substituting 3-acetyl-5-bromopyridine from Step 1 for ethyl 5-bromonicotinate the N-isopropyl-1-[3-(5-acetylpyridin-3-yl)phenyl]-1,4-dihydro[1,8]naphthyridin-4-one-3-carboxamide compound was obtained as a white solid.

$^1$H NMR (CDCl$_3$) δ 1.29 (d, 6H), 2.69 (s, 3H), 4.28 (m, 1H), 7.48 (dd, 1H), 7.51 (d, 1H), 7.69 (s, 1H), 7.72 (t, 1H), 7.80 (d, 1H), 8.42 (s, 1H), 8.69 (m, 1H), 8.82 (d, 1H), 9.05 (s, 2H) 9.17 (s, 1H), 9.63 (br, NH).

Example 28

N-Isopropyl-1-[3-(6-methylpyridin-3-yl)phenyl]-1,4-dihydro[1,8]naphthyridin-4-one-3-carboxamide

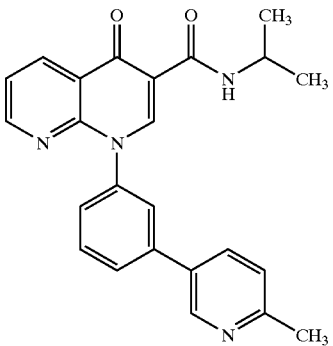

Step 1: 5-Bromo-2-methylpyridine

Following the procedure of Step 1 of Example 26 but substituting methylmagnesium chloride for isobutylmagnesium bromide the 5-bromo-2-methylpyridine compound was obtained as a solid.

Step 2: N-Isopropyl-1-[3-(6-methylpyridin-3-yl)phenyl]-1,4-dihydro[1,8]naphthyridin-4-one-3-carboxamide Following the procedure of Example 24 but substituting 5-bromo-2-methylpyridine from Step 1 for ethyl 5-bromonicotinate the N-Isopropyl-1-[3-(6-methylpyridin-3-yl)phenyl]-1,4-dihydro[1,8]naphthyridin-4-one-3-carboxamide compound was obtained as a solid.

$^1$H NMR (CDCl$_3$) δ 1.32 (d, 6H), 2.63 (m, 3H), 4.30 (m, 1H), 7.25 (d, 1H), 7.45–7.51 (m, 2H), 7.63 (s, 1H), 7.69 (t, 1H), 7.77 (d, 1H), 7.82 (dd, 1H), 8.72 (m, 1H), 8.78 (s, 1H), 8.85 (d, 1H), 9.08 (s, 1H), 9.68 (br, NH).

Example 29

N-Cyclopropyl-1-[3-(1-oxidopyrimidin-5-yl)phenyl]-1,4-dihydro[1,8]naphthyridin-4-one-3-carboxamide

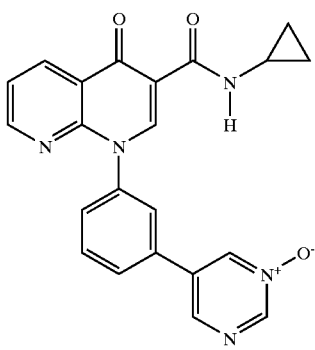

Step 1: 5-Bromo-1-oxidopyrimidine

To 5-bromopyrimidine (2.05 g, 12.9 mmol) in methylene chloride (25 ml) was added m-chloroperoxybenzoic acid (ca 70% pure, 3.17 g, 12.9 mmol) and the resulting mixture was stirred at room temperature for 5 days. Calcium hydroxide (1 g) was added and after 10 minutes the mixture was filtered through celite. The product from evaporation of the filtrate was chromatographed on silica gel eluting with ethyl acetate to afford the 5-bromo-1-oxidopyrimidine compound as a white solid.

Step 2: N-Cyclopropyl-1-[3-(1-oxidopyrimidinyl-5-yl)phenyl]-1,4-dihydro[1,8]naphthyridin-4-one-3-carboxamide Following the procedure of Example 24 but substituting 5-bromo-1-oxidopyrimidine from Step 1 for ethyl 5-bromonicotinate and N-cyclopropyl-1-(3-bromophenyl)-1,4-dihydro[1,8]naphthyridin-4-one-3-carboxamide for N-isopropyl-1-(3-bromophenyl)-1,4-dihydro[1,8]naphthyridin-4-one-3-carboxamide, the N-Cyclopropyl-1-[3-(1-oxidopyrimidinyl-5-yl)phenyl]-1,4-dihydro[1,8]naphthyridin-4-one-3-carboxamide compound was obtained as a white solid.

$^1$H NMR (CDCl$_3$) δ 0.66 (m, 2H), 0.84 (m, 2H), 2.97 (m, 1H), 7.48 (m, 1H), 7.58 (d, 1H), 7.65 (s, 1H), 7.71 (d, 1H), 7.77 (t, 1H), 8.46 (s, 1H), 8.60 (s, 1H), 8.68 (brs, 1H), 8.81 (dd, 1H), 8.98 (s, 1H), 9.02 (s, 1H), 9.72 (br, NH).

Example 30

1-{3-[6-(1-hydroxy-1-methylethyl)-1-oxidopyridin-3-yl]penyl}-1,4-dihydro[1,8]naphthyridin-4-one-3-carboxamide

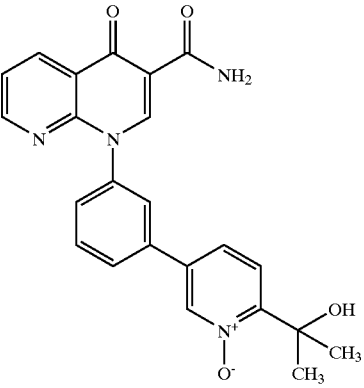

Step 1: 5-Bromo-2-(1-hydroxy-1-methylethyl) pyridine

To a suspension of 2,5-dibromopyridine in toluene (12 ml/mmol) cooled to −78° C. was added n-butyllithium 2.5M in hexanes (1.05 eq) and the resulting mixture was stirred in the cold for 2.5 hours. Acetone (2 eq) was added and stirring was continued for 1.5 h. After quenching with saturated aqueous ammonium chloride solution, the mixture was warmed to room temperature and partitioned between ethyl acetate and water. The product from the organic phase was chromatographed on silica gel eluting with 20% ethyl acetate in hexane to afford the 5-Bromo-2-(1-hydroxy-1-methylethyl) pyridine compound as a syrup.

Step 2: 5-Bromo-2-(1-hydroxy-1-methylethyl) pyridine N-oxide

To a solution of 5-bromo-2-(1-hydroxy-1-methylethyl) pyridine from Step 1 in methylene chloride (5 ml/mmol) at room temperature was added m-chloroperoxybenzoic acid 70% (1.1 eq) and the resulting mixture was stirred at room temperature for 18 hours. An excess of calcium hydroxide was added and after 5 minutes the mixture was filtered through a bed of celite. The crude product from evaporation of the filtrate was chromatographed on silica gel eluting with 80% ethyl acetate in hexane and the 5-bromo-2-(1-hydroxy-1-methylethyl) pyridine N-oxide compound was obtained as a white solid.

Step 3: 1-(3-bromophenyl)-1,4-dihydro[1,8]naphthyridin-4-one-3-carboxamide

Following the procedure of Step 4 of Example 1 but substituting 28% aqueous ammonium hydroxide for isopropylamine the 1-(3-bromophenyl)-1,4-dihydro[1,8]naphthyridin-4-one-3-carboxamide compound was obtained as a solid.

Step 4: 1-{3-[6-(1-hydroxy-1-methylethyl)-1-oxidopyridin-3-yl]phenyl}-1,4-dihydro[1,8]naphthyridin-4-one-3-carboxamide Following the procedure of Example 24 but substituting 5-bromo-2-(1-hydroxy-1-methylethyl) pyridine N-oxide from Step 2 above for ethyl 5-bromonicotinate and 1-(3-bromophenyl)-1,4-dihydro[1,8]naphthyridin-4-one-3- carboxamide for N-isopropyl-1-(3-bromophenyl)-1,4-dihydro[1,8]naphthyridin-4-one-3-carboxamide, the 1-{3-[6-(1-hydroxy-1-methylethyl)-1-oxidopyridin-3-yl]phenyl}-1,4-dihydro[1,8]naphthyridin-4-one-3-carboxamide compound was obtained as a solid.

$^1$H NMR (CDCl$_3$) δ 1.76 (s, 6H), 5.83 (br, 1H, NH). 7.50 (d, 1H), 7.55 (m, 1H), 7.57–7.62 (m, 2H), 7.65 (m, 2H), 7.72–7.78 (m, 2H), 8.55 (s, 1H, OH), 8.75 (m, 1H), 8.90 (dd, 1H), 9.08 (s, 1H), 9.52 (br, 1H, NH).

Example 31

N-Isopropyl-1-{3-[4-(pyridin-3-yl)phenyl]phenyl}-1,4-dihydro[1,8]naphthyridin-4-one-3-carboxamide

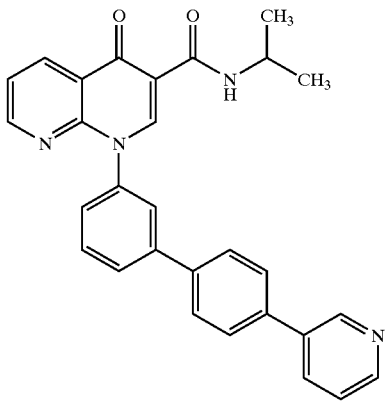

Step 1: N-Isopropyl-1-[3-(4,4,5,5-tetramethyl-1,3,2-dioxaborolan-2-yl)phenyl]-1,4-dihydro[1,8]naphthyridin-4-one-3-carboxamide A mixture of N-isopropyl-1-(3-bromophenyl)-1,4-dihydro[1,8]naphthyridin-4-one-3-carboxamide from Step 4 of Example 1, diboron pinacol ester (1.1 eq), potassium acetate (3.5 eq) and [1,1'-bis (diphenylphosphino)ferrocene]dichloropalladium(II) (0.05 eq) in N,N-dimethylformamide (5 ml/mmol) was stirred at 85° C. for 18 hours. A further amount of diboron pinacol ester (0.4 eq) and palladium catalyst (0.05 eq) were added and heating and stirring were continued for a further 24 hours. After cooling, the mixture was partitioned between ethyl acetate and water, and the crude product from the organic phase was chromatographed on silica gel eluting with a 1:1 mixture of ethyl acetate and hexane. The product was then stirred in hexane at room temperature for several hours and filtered to afford the N-Isopropyl-1-[3-(4,4,5,5,-tetramethyl-1,3,2-dioxaborolan-2-yl)phenyl]-1,4-dihydro[1,8]naphthyridin-4-one-3-carboxamide compound as a white solid.

Step 2: 3-(4-Bromophenyl)pyridine

A mixture of pyridine-3-boronic acid 1,3-propanediol cyclic ester, 4-bromoiodobenzene (1.1 eq), [1,1'-bis (diphenylphosphino)ferrocene]dichloropalladium(II) (0.05 eq) and 2M aqueous sodium carbonate (5 eq) in N,N-dimethylformamide (2 ml/mmol) was stirred at 85° C. for 4 hours. After quenching with saturated aqueous ammonium chloride solution, the mixture was partitioned between ethyl acetate and water, and the crude product from the organic phase was chromatographed on silica gel eluting with a 1:9 mixture of ethyl acetate and hexane to afford the 3-(4-Bromophenyl)pyridine compound as a solid.

Step 3: N-Isopropyl-1-{3-[4-(pyridin-3-yl)phenyl]phenyl}-1,4-dihydro[1,8]naphthyridin-4-one-3-carboxamide A mixture of the boronate from Step 1, 3-(4-bromophenyl)pyridine from Step 2 (1.5 eq), [1,1'-bis (diphenylphosphino)ferrocene]dichloropalladium(II) (0.05 eq) and 2M aqueous sodium carbonate (5 eq) in N,N-dimethylformamide (7 ml/mmol) was stirred at 85° C. for 1 hour. After cooling, the mixture was partitioned between ethyl acetate and water. The crude product from the organic phase was chromatographed on silica gel eluting with a 7:3 mixture of ethyl acetate and methylene chloride to afford the N-Isopropyl-1-{3-[4-(pyridin-3-yl)phenyl]phenyl}-1,4-dihydro[1,8]naphthyridin-4-one-3-carboxamide compound as a solid.

$^1$H NMR (CDCl$_3$) δ 1.30 (d, 6H), 4.25 (m, 1H), 7.35 (m, 1H), 7.39–7.48 (m, 2H), 7.60–7.75 (m, 6H), 7.80 (d, 1H), 7.90 (d, 1H), 8.58 (d, 1H), 8.70 (m, 1H), 8.82 (d, 1H), 8.88 (s, 1H), 9.08 (s, 1H), 9.68 (br, NH).

Example 32

N-Cyclopropyl-1-[3-(5-methylsulfonylpyridin-3-yl)]Phenyl]-1,4-dihydro[1,8]naphthyridin-4-one-3-carboxamide

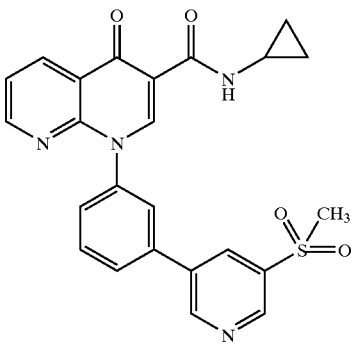

Step 1: N-Cyclopropyl-1-[3-(4,4,5,5,-tetramethyl-1,3,2-dioxaborolan-2-yl)phenyl]-1,4-dihydro[1,8]naphthyridin-4-one-3-carboxamide Following the procedure of Step 1 of Example 31 but substituting N-cyclopropyl-1-(3-bromophenyl)-1,4-dihydro[1,8]naphthyridin-4-one-3-carboxamide from step 1 of example 14 for N-isopropyl-1-(3-bromophenyl)-1,4-dihydro[1,8]naphthyridin-4-one-3-carboxamide the N-Cyclopropyl-1-[3-(4,4,5,5,-tetramethyl-1,3,2-dioxaborolan-2-yl)phenyl]-1,4-dihydro[1,8]naphthyridin-4-one-3-carboxamide compound was obtained as a white solid.

Step 2: 3-Bromo-5-methylsulfonylpyridine

To 3,5-dibromopyridine (2.96 g, 12.5 mmol) in diethyl ether (70 ml) at −78° C. was added n-butyllithium 1.6M in hexanes (8.6 ml, 13.7 mmol) and the resulting mixture was stirred in the cold for 3 hours. Dimethyl disulfide (1.12 ml, 12.5 mmol) was added and the mixture was warmed to room temperature, then partitioned between ether and water. To the crude product from evaporation of the organic phase was added tetrahydrofuran (80 ml), methanol (20 ml), oxone (17 g) and enough saturated aqueous sodium bicarbonate to afford a slightly basic medium. After stirring for 4 hours at room temperature, an excess of 1M aqueous sodium metabisulfite was added, the organic solvents were evaporated, and the residue was partitioned between ethyl acetate and water. The crude product from the organic phase was stirred in a small volume of ethyl acetate and filtered to afford the 3-Bromo-5-methylsulfonylpyridine compound as a solid.

Step 3: N-Cyclopropyl-1-[3-(5-methylsulfonylpyridin-3-yl)]phenyl]-1,4-dihydro[1,8]naphthyridin-4-one-3-carboxamide Following the procedure of Step 3 of Example 31 but substituting 3-bromo-5-methylsulfonylpyridine from Step 2 above for 3-(4-bromophenyl)pyridine, and N-cyclopropyl-1-[3-(4,4,5,5,-tetramethyl-1,3,2-dioxaborolan-2-yl)phenyl]-1,4-dihydro[1,8]naphthyridin-4-one-3-carboxamide from Step 1 for N-isopropyl-1-[3-(4,4,5,5,-tetramethyl-1,3,2-dioxaborolan-2-yl)phenyl]-1,4-dihydro[1,8]naphthyridin-4-one-3-carboxamide, the N-Cyclopropyl-1-[3-(5-methylsulfonylpyridin-3-yl)]phenyl]-1,4-dihydro[1,8]naphthyridin-4-one-3-carboxamide compound was obtained as a solid.

$^1$H NMR (CDCl$_3$) δ 0.71 (m, 2H), 0.90 (m, 2H), 3.03 (m, 1H), 3.21 (s, 3H), 7.53 (m, 1H), 7.60 (d, 1H), 7.74 (s, 1H), 7.80 (t, 1H), 7.86 (d, 1H), 8.45 (m, 1H), 8.74 (m, 1H), 8.86 (d, 1H), 9.09 (s, 1H), 9.20 (d, 2H), 9.78 (br, NH).

Example 33

N-Cyclopropyl-1-{3-[4-(1-hydroxy-1-methylethyl)-1-oxidopyridin-2-yl]phenyl}-1,4-dihydro[1,8]naphthyridin-4-one-3-carboxamide

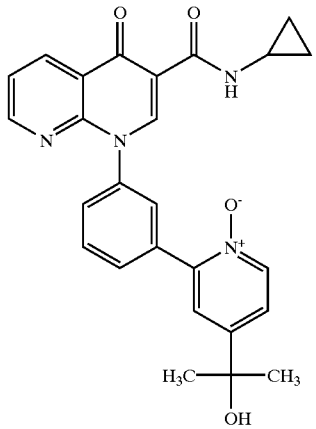

Step 1: Methyl 2-bromoisonicotinate

To a solution of 2-bromoisonicotinic acid (*Chem. Pharm. Bull.,* 38:2446(1990)) (2.0 g) in tetrahydrofuran (100 ml) was added excess ethereal diazomethane and the resulting mixture was stirred at room temperature for 1 hour. The mixture was evaporated and the product chromatographed on silica gel eluting with a 1:3 mixture of ethyl acetate and hexane to afford the Methyl 2-bromoisonicotinate ester as a colorless liquid.

Step 2: 2-Bromo-4-(1-hydroxy-1-methylethyl)pyridine

Following the procedure of Step 1 of Example 25, but substituting methyl 2-bromoisonicotinate from Step 1 for ethyl 5-bromonicotinate, the 2-Bromo-4-(1-hydroxy-1-methylethyl)pyridine compound was obtained as a white solid.

Step 3: 2-Bromo-4-(1-hydroxy-1-methylethyl)pyridine-N-oxide

Following the procedure of Step 2 of Example 30 but substituting 2-bromo-4-(1-hydroxy-1-methylethyl)pyridine from Step 2 for 5-bromo-2-(1-hydroxy-1-methylethyl) pyridine the 2-Bromo-4-(1-hydroxy-1-methylethyl)pyridine-N-oxide compound was obtained as a white solid.

Step 4: N-Cyclopropyl-1-{3-[4-(1-hydroxy-1-methylethyl)-1-oxidopyridin-2-yl]phenyl}-1,4-dihydro[1,8]naphthyridin-4-one-3-carboxamide Following the procedure of Step 3 of Example 32, but substituting 2-bromo-4-(1-hydroxy-1-methylethyl)pyridine-N-oxide from Step 3 for 3-bromo-5-methylsulfonylpyridine, the N-Cyclopropyl-1-{3-[4-(1-hydroxy-1-methylethyl)-1-oxidopyridin-2-yl]phenyl}-1,4-dihydro[1,8]naphthyridin-4-one-3-carboxamide compound was obtained as a beige solid.

$^1$H NMR (DMSO-d$_6$) δ 0.57 (m, 2H), 0.79 (m, 2H), 1.45 (s, 6H), 2.90 (m, 1H), 5.35 (s, 1H, OH), 7.48 (m, 1H), 7.64 (m, 1H), 7.72 (m, 3H), 8.11 (m, 2H), 8.30 (d, 1H), 8.72 (dd, 1H), 8.78 (m, 1H), 8.82 (s, 1H), 9.72 (br, NH).

Example 34

N-Cyclopropyl-1-{3-[5-(1-hydroxy-1-methylethyl)pyridin-2-yl]phenyl}1,4-dihydro[1,8]naphthyridin-4-one-3-carboxamide

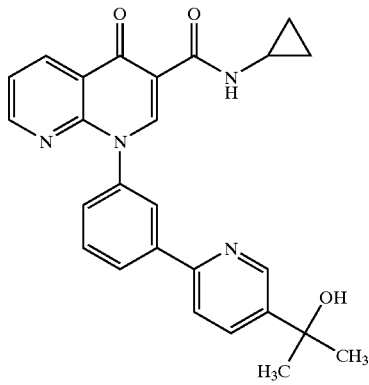

Step 1: 2-Bromo-5-(1-hydroxy-1-methylethyl)pyridine

A solution of 2,5-dibromopyridine in diethyl ether (5 ml/mmol) was cooled to −78° C., and n-butyllithium 2.5M in hexanes (1.05 eq) was added slowly. After 2 h in the cold, acetone (1.3 eq) was added and stirring was continued for 1 hour. The resulting mixture was quenched with saturated aqueous ammonium chloride solution, warmed to room temperature, and partitioned between ether and water. The crude product from the organic phase was triturated with 1:1 ether-hexane and filtered to afford the 2-Bromo-5-(1-hydroxy-1-methylethyl)pyridine compound as a solid.

Step 2: N-Cyclopropyl-1-{3-[5-(1-hydroxy-1-methylethyl)pridin-2-yl]phenyl}-1,4-dihydro[1,8]naphthyridin-4-one-3-carboxamide Following the procedure of Step 3 of Example 32, but substituting 2-bromo-5-(1-hydroxy-1-methylethyl)pyridine from Step 1 for 3-bromo-5-methylsulfonylpyridine, the N-Cyclopropyl-1-{3-[5-(1-hydroxy-1-methylethyl)pyridin-2-yl]phenyl}-1,4-dihydro[1,8]naphthyridin-4-one-3-carboxamide compound was obtained as a solid.

$^1$H NMR (CDCl$_3$) δ 0.71 (m, 2H), 0.90 (m, 2H), 1.68 (s, 6H), 1.85 (s, 1H, OH), 3.04 (m, 1H), 7.45–7.52 (m, 2H), 7.71 (t, 1H), 7.79 (d, 1H), 7.95 (dd, 1H), 8.16 (s, 1H), 8.20 (d, 1H), 8.72 (m, 1H), 8.80–8.87 (m, 2H), 9.12 (s, 1H), 9.82 (br, NH).

Example 35

N-Cyclopropyl-1-{3-[3-(1-hydroxy-1-methylethyl) pyridin-4-yl]phenyl}-1,4-dihydro[1,8]naphthyridin-4-one-3-carboxamide

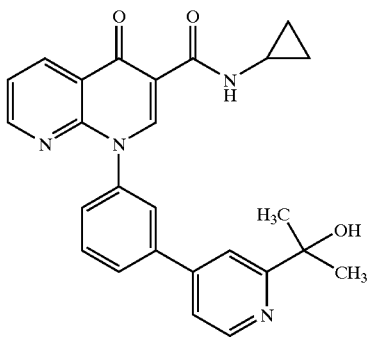

Step 1: 4-Bromo-2-(1-hydroxy-1-methylethyl)pyridine

Following the sequence described in Steps 1–2 of Example 33, but substituting 4-bromopicolinic acid (Aust. J. Chem. 24:390(1971)) for 2-bromoisonicotinic acid in Step 1, the 4-Bromo-2-(1-hydroxy-1-methylethyl)pyridine compound was obtained as a white solid.

Step 2: N-Cyclopropyl-1-{3-[3-(1-hydroxy-1-methylethyl) pyridin-4-yl]phenyl}-1,4-dihydro[1,8]naphthyridin-4-one-3-carboxamide Following the procedure of Step 3 of Example 32, but substituting 4-bromo-2-(1-hydroxy-1-methylethyl)pyridine from Step 1 for 3-bromo-5-methylsulfonylpyridine, the N-Cyclopropyl-1-{3-[3-(1-hydroxy-1-methylethyl)pyridin-4-yl]phenyl}-1,4-dihydro[1,8]naphthyridin-4-one-3-carboxamide compound was obtained as a beige solid.

$^1$H NMR (DMSO-$d_6$) δ 0.57 (m, 2H), 0.78 (m, 2H), 1.48 (s, 6H), 2.91 (m, 1H), 5.27 (s, 1H, OH), 7.62–7.66 (m, 2H), 7.72–7.79 (m, 2H), 8.01 (m, 1H), 8.10 (s, 1H), 8.58 (d, 1H), 8.73–8.79 (m, 2H), 8.84 (s, 1H), 9.73 (br, NH).

Example 36

Synthesis of N-Cyclopropyl-1-{3-[3-(1-hydroxy-1-methylethyl)-1-oxidopyridin-4-yl]phenyl}-1,4-dihydro[1,8]naphthyridin-4-one-3-carboxamide

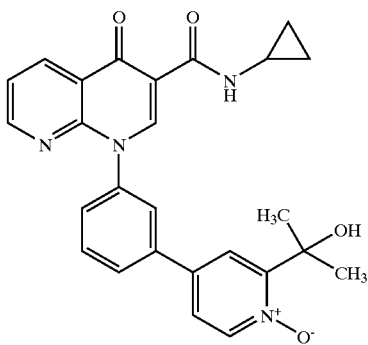

Step 1: 4-Bromo-2-(1-hydroxy-1-methylethyl)pyridine N-oxide

Following the procedure of Step 2 of Example 30, but substituting 4-bromo-2-(1-hydroxy-1-methylethyl)pyridine from Step 1 of Example 35 for 5-bromo-2-(1-hydroxy-1-methylethyl) pyridine, the 4-Bromo-2-(1-hydroxy-1-methylethyl)pyridine N-oxide compound was obtained as a white solid.

Step 2: N-Cyclopropyl-1-{3-[3-(1-hydroxy-1-methylethyl)-1-oxidopyridin-4-yl]phenyl}-1,4-dihydro[1,8]naphthyridin-4-one-3-carboxamide Following the procedure of Step 3 of Example 32, but substituting 4-bromo-2-(1-hydroxy-1-methylethyl)pyridine-N-oxide from Step 1 for 3-bromo-5-methylsulfonylpyridine, the N-Cyclopropyl-1-{3-[3-(1-hydroxy-1-methylethyl)-1-oxidopyridin-4-yl]phenyl}-1,4-dihydro[1,8]naphthyridin-4-one-3-carboxamide compound was obtained as a beige solid.

$^1$H NMR (DMSO-$d_6$) δ 0.57 (m, 2H), 0.78 (m, 2H), 1.62 (s, 6H), 2.90 (m, 1H), 6.99 (s, 1H, OH), 7.65–7.84 (m, 4H), 7.94 (s, 1H), 8.03 (dd, 1H), 8.15 (s, 1H), 8.38 (d, 1H), 8.73–8.78 (m, 2H), 8.83 (s, 1H), 9.73 (br, NH).

Example 37

N-Cyclopropyl-1-[3-(6-isopropylsulfonylpyridin-3-yl)]phenyl]-1,4-dihydro[1,8]naphthyridin-4-one-3-carboxamide

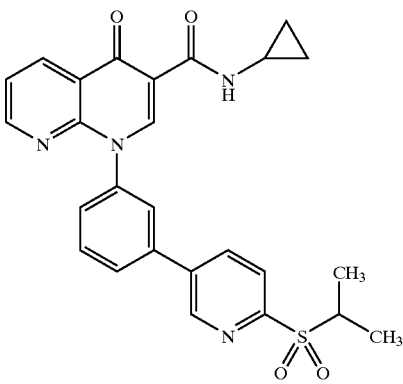

Step 1: 5-Bromo-2-isopropylthiopyridine

To a mixture of 2,5-dibromopyridine (2.07 g, 8.73 mmol) and 2-propanethiol (0.97 ml, 10.4 mmol) in N,N-dimethylformamide (20 ml) at 0° C. was added portionwise sodium hydride 60% dispersed in oil (450 mg, 11.3 mmol). The resulting mixture was stirred at room temperature for 1 hour, then partitioned between ether and water. The crude product from the organic phase was chromatographed on silica gel eluting with 10% ethyl acetate in hexane to afford the 5-Bromo-2-isopropylthiopyridine compound as a solid.

Step 2: 5-Bromo-2-isopropylsulfonylpyridine

To a solution of 5-bromo-2-isopropylthiopyridine from Step 1 (2.03 g, 8.75 mmol) in tetrahydrofuran (50 ml) and methanol (25 ml) at 0° C. was added oxone (15.8 g, 25.8 mmol) and then saturated aqueous sodium bicarbonate (25 ml). The resulting mixture was stirred at room temperature for 6 hours. The mixture was quenched with aqueous sodium bicarbonate and partitioned between ethyl acetate and water. The crude product from the organic phase was chromatographed on silica gel eluting with 20% ethyl acetate in hexane to afford the 5-Bromo-2-isopropylsulfonylpyridine compound as a white solid.

Step 3: N-Cyclopropyl-1-[3-(6-isopropylsulfonylpyridin-3-yl)]phenyl]-1,4-dihydro[1,8]naphthyridin-4-one-3-carboxamide Following the procedure of Step 3 of Example 32, but substituting 5-bromo-2-isopropylsulfonylpyridine from Step 2 for 3-bromo-5-methylsulfonylpyridine, the N-Cyclopropyl-1-[3-(6-isopropylsulfonylpyridin-3-yl)] phenyl]-1,4-dihydro[1,8]naphthyridin-4-one-3-carboxamide compound was obtained as a solid.

¹H NMR (CDCl₃) δ 0.70 (m, 2H), 0.89 (m, 2H), 1.39 (d, 6H), 3.00 (m, 1H), 3.82 (m, 1H), 7.51 (m, 1H), 7.60 (d, 1H), 7.72 (s, 1H), 7.80 (t, 1H), 7.83 (d, 1H), 8.15–8.24 (m, 2H), 8.72 (m, 1H), 8.86 (dd, 1H), 9.03 (s, 1H), 9.10 (s, 1H), 9.77 (br, NH).

Example 38

N-Cyclopropyl-1-[3-(6-methoxypyridin-3-yl)phenyl]-1,4-dihydro[1,8]naphthyridin-4-one-3-carboxamide

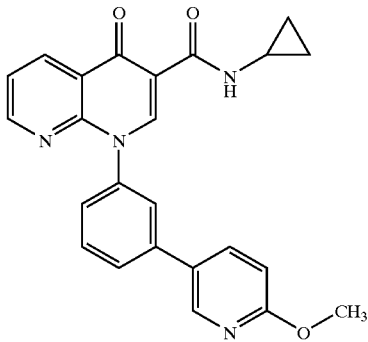

Step 1: 5-Bromo-2-methoxypyridine

To a solution of 2,5-dibromopyridine (6.95 g, 29 mmol) in N,N-dimethylformamide (5 ml) was added methanol (3.56 ml) and 1M potassium tert-butoxide (32.3 ml) and the resulting mixture was stirred at room temperature for 18 hours. The resulting slurry was quenched with saturated aqueous ammonium chloride solution and partitioned between ethyl acetate and water. The crude product from the organic phase was chromatographed on silica gel eluting with a 1:9 mixture of ether and hexane to afford the 5-Bromo-2-methoxypyridine compound as an oil.

Step 2: N-Cyclopropyl-1-[3-(6-methoxypyridin-3-yl)phenyl]-1,4-dihydro[1,8]naphthyridin-4-one-3-carboxamide Following the procedure of Step 3 of Example 32, but substituting 5-bromo-2-methoxypyridine from Step 1 for 3-bromo-5-methylsulfonylpyridine, the N-cyclopropyl-1-[3-(6-methoxypyridin-3-yl)phenyl]-1,4-dihydro[1,8]naphthyridin-4-one-3-carboxamide compound was obtained as a solid.

¹H NMR (CDCl₃) δ 0.71 (m, 2H), 0.89 (m, 2H), 3.00 (m, 1H), 4.00 (s, 3H), 6.85 (d, 1H), 7.44 (d, 1H), 7.50 (m, 1H), 7.62 (s, 1H), 7.68 (t, 1H), 7.73 (d, 1H), 7.83 (dd, 1H), 8.44 (s, 1H), 8.73 (m, 1H), 8.85 (dd, 1H), 9.10 (s, 1H), 9.82 (br, NH).

Example 39

N-Cyclopropyl-1-[3-(6-methylpyridin-3-yl)phenyl]-1,4-dihydro[1,8]naphthyridin-4-one-3-carboxamide

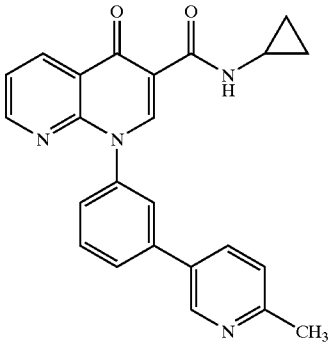

Following the procedure of Step 3 of Example 32, but substituting 5-bromo-2-methylpyridine from Step 1 of Example 28 for 3-bromo-5-methylsulfonylpyridine, the title compound was obtained as a solid.

¹H NMR (CDCl₃) δ 0.72 (m, 2H), 0.90 (m, 2H), 2.65 (s, 3H), 3.03 (m, 1H), 7.28 (d, 1H), 7.45–7.53 (m, 2H), 7.66 (s, 1H), 7.72 (t, 1H), 7.80 (d, 1H), 7.84 (dd, 1H), 8.73 (m, 1H), 8.80 (s, 1H), 8.86 (dd, 1H), 9.11 (s, 1H), 9.82 (br, NH).

Example 40

N-Cyclopropyl-1-{3-[6-(2,2,2-trifluoroethoxy)pyridin-3-yl]phenyl}-1,4-dihydro[1,8]naphthyridin-4-one-3-carboxamide

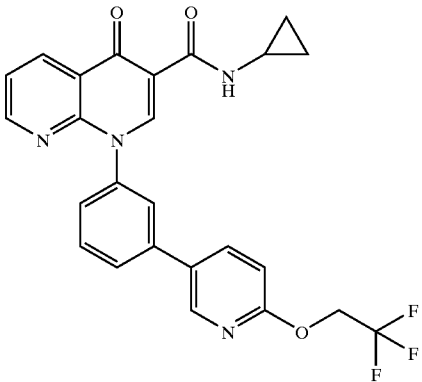

Step 1: 5-Bromo-2-(2,2,2-trifluoroethoxy)pyridine
Following the procedure of Step 1 of Example 38, but substituting 2,2,2-trifluoroethanol for methanol, with heating at 70° C. for 18 hours, the 5-Bromo-2-(2,2,2-trifluoroethoxy)pyridine compound was obtained as an oil.

Step 2: N-Cyclopropyl-1-{3-[6-(2,2,2-trifluoroethoxy)pyridin-3-yl]phenyl}-1,4-dihydro[1,8]naphthyridin-4-one-3-carboxamide Following the procedure of Step 3 of Example 32, but substituting 5-bromo-2-(2,2,2-trifluoroethoxy)pyridine from Step 1 for 3-bromo-5-methylsulfonylpyridine, the N-Cyclopropyl-1-{3-[6-(2,2,2-trifluoroethoxy)pyridin-3-yl]phenyl}-1,4-dihydro[1,8]naphthyridin-4-one-3-carboxamide compound was obtained as a solid.

¹H NMR (CDCl₃) δ 0.72 (m, 2H), 0.90 (m, 2H), 3.03 (m, 1H), 4.85 (q, 2H), 7.00 (d, 1H), 7.43–7.53 (m, 2H), 7.62 (s, 1H), 7.69–7.78 (m, 2H), 7.92 (dd, 1H), 8.42 (s, 1H), 8.73 (m, 1H), 8.85 (dd, 1H), 9.10 (s, 1H), 9.80 (br, NH).

Example 41

N-Cyclopropyl-1-[3-(5-bromopyridin-3-yl)phenyl]-1,4-dihydro[1,8]naphthyridin-4-one-3-carboxamide

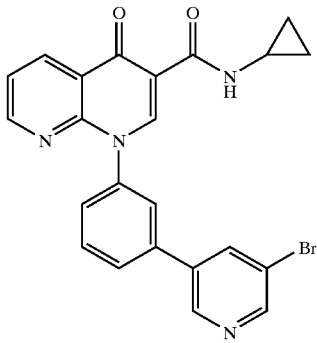

Following the procedure of Step 3 of Example 32, but substituting 3,5-dibromopyridine for 3-bromo-5-methylsulfonylpyridine, the title compound was obtained as a white solid.

$^1$H NMR (DMSO-d$_6$) δ 0.58 (m, 2H), 0.79 (m, 2H), 2.90 (m, 1H), 7.65 (m, 1H), 7.71–7.77 (m, 2H), 8.03 (d, 1H), 8.14 (s, 1H), 8.49 (s, 1H), 8.74 (brs, 1H), 8.79 (brs, 1H), 8.86 (s, 1H), 9.01 (s, 1H), 9.73 (br, NH).

Example 42

N-Cyclopropyl-1-[3-(6-benzyloxypyridin-3-yl)phenyl]-1,4-dihydro[1,8]naphthyridin-4-one-3-carboxamide

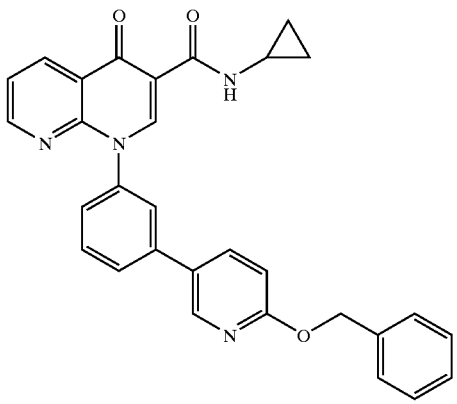

Step 1: 2-Benzyloxy-5-bromopyridine

A mixture of 2,5-dibromopyridine, benzyl alcohol (1.3 eq), potassium hydroxide pellets (2.4 eq) and dibenzo-18-crown-6 (0.05 eq) in toluene (4 ml/mmol) was refluxed with azeotropic removal of water for 3 hours. After evaporation of the toluene, the resulting mixture was partitioned between chloroform and water. The crude product from the organic phase was recrystallized from ether-hexane to afford the 2-Benzyloxy-5-bromopyridine compound as a solid.

Step 2: N-Cyclopropyl-1-[3-(6-benzyloxypyridin-3-yl)phenyl]-1,4-dihydro[1,8]naphthyridin-4-one-3-carboxamide Following the procedure of Step 3 of Example 32, but substituting 2-benzyloxy-5-bromopyridine from Step 1 for 3-bromo-5-methylsulfonylpyridine, the N-Cyclopropyl-1-[3-(6-benzyloxypyridin-3-yl)phenyl]-1,4-dihydro[1,8]naphthyridin-4-one-3-carboxamide compound was obtained as a white solid.

$^1$H NMR (DMSO-d$_6$) δ 0.57 (m, 2H), 0.79 (m, 2H), 2.91 (m, 1H), 5.42 (s, 2H) 7.00 (d, 1H), 7.32–7.48 (m, 5H), 7.61–7.72 (m, 3H), 7.90 (d, 1H), 7.99 (s, 1H), 8.14 (d, 1H), 8.59 (s, 1H), 8.73–8.84 (m, 3H), 9.73 (br, NH).

Example 43

N-Cyclopropyl-1-{3-[6-dicyclopropyl(hydroxy)methyl-1-oxidopyridin-3-yl]phenyl}-1,4-dihydro[1,8]naphthyridin-4-one-3-carboxamide

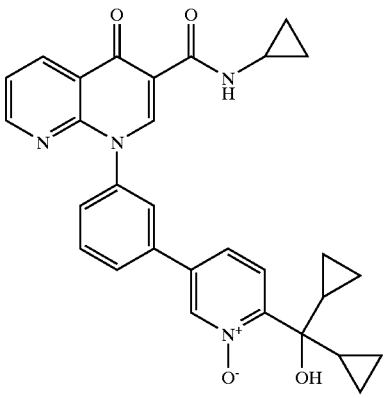

Step 1: 5-Bromo-2-dicyclopropyl(hydroxy)methylpyridine N-oxide

Following the procedure of Steps 1 and 2 of Example 30, but substituting dicyclopropyl ketone for acetone in Step 1, the 5-Bromo-2-dicyclopropyl(hydroxy)methylpyridine N-oxide compound was obtained as a solid.

Step 2: N-Cyclopropyl-1-{3-[6-dicyclopropyl(hydroxy)methyl-1-oxidopyridin-3-yl]phenyl}-1,4-dihydro[1,8]naphthyridin-4-one-3-carboxamide Following the procedure of Step 3 of Example 32, but substituting 5-bromo-2-dicyclopropyl(hydroxy)methylpyridine N-oxide from Step 1 for 3-bromo-5-methylsulfonylpyridine, the N-Cyclopropyl-1-{3-[6-dicyclopropyl(hydroxy)methyl-1-oxidopyridin-3-yl]phenyl}-1,4-dihydro[1,8]naphthyridin-4-one-3-carboxamide compound was obtained as a white solid.

$^1$H NMR (CDCl$_3$) δ 0.52 (m, 4H), 0.70 (m, 4H), 0.76 (m, 2H), 0.89 (m, 2H), 1.35 (m, 2H), 3.02 (m, 1H), 7.52 (m, 1H), 7.58 (m, 1H), 7.62 (dd, 1H), 7.68 (s, 1H), 7.73–7.80 (m, 3H), 8.15 (br, 1H, OH), 8.49 (s, 1H), 8.72 (m, 1H), 8.85 (dd, 1H), 9.09 (s, 1H), 9.78 (br, NH).

Example 44

N-Cyclopropyl-1-{3-[5-(1-hydroxy-1-methylethyl)-1-oxidopyridin-2-yl]pheny}-1,4-dihydro[1,8]naphthyridin-4-one-3-carboxamide

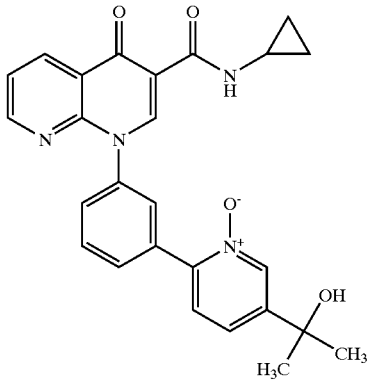

Step 1: 2-Bromo-5-(1-hydroxy-1-methylethyl)pyridine N-oxide

Following the procedure of Step 2 of Example 30, but substituting 2-bromo-5-(1-hydroxy-1-methylethyl)pyridine from Step 1 of Example 34 for 5-bromo-2-(1-hydroxy-1-methylethyl) pyridine, the 2-Bromo-5-(1-hydroxy-1-methylethyl)pyridine N-oxide compound was obtained as a white solid.

Step 2: N-Cyclopropyl-1-{3-[5-(1-hydroxy-1-methylethyl)-1-oxidopyridin-2-yl]phenyl}-1,4-dihydro[1,8]naphthyridin-4-one-3-carboxamide Following the procedure of Step 3 of Example 32, but substituting 2-bromo-5-(1-hydroxy-1-methylethyl)pyridine N-oxide from Step 1 for 3-bromo-5-methylsulfonylpyridine, the N-Cyclopropyl-1-{3-[5-(1-hydroxy-1-methylethyl)-1-oxidopyridin-2-yl]phenyl}-1,4-dihydro[1,8]naphthyridin-4-one-3-carboxamide compound was obtained as a solid.

$^1$H NMR (CDCl$_3$) δ 0.69 (m, 2H), 0.88 (m, 2H), 1.63 (s, 6H), 2.20 (s, 1H, OH), 2.98 (m, 1H), 7.38–7.49 (m, 3H), 7.52 (d, 1H), 7.70 (t, 1H), 7.98–8.04 (m, 2H), 8.50 (s, 1H), 8.69 (m, 1H), 8.80 (dd, 1H), 9.08 (s, 1H), 9.75 (br, NH).

Example 45

N-Cyclopropyl-1-{3-[6-(1-hydroxy-1-methylethyl)pyridin-3-yl]phenyl}-1,4-dihydro[1,8]naphthyridin-4-one-3-carboxamide

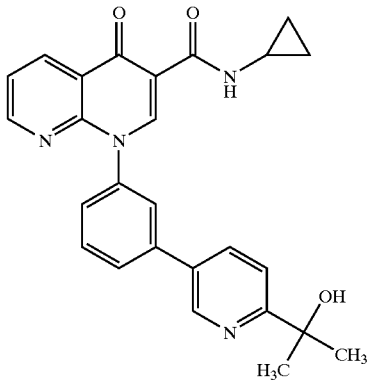

Following the procedure of Step 3 of Example 32, but substituting 5-bromo-2-(1-hydroxy-1-methylethyl) pyridine from Step 1 of Example 30 for 3-bromo-5-methylsulfonylpyridine, the title compound was obtained as a solid.

$^1$H NMR (CDCl$_3$) δ 0.72 (m, 2H), 090 (m, 2H), 1.62 (s, 6H), 3.02 (m, 1H), 4.85 (s, 1H, OH), 7.48–7.53 (m, 3H), 7.68 (s, 1H), 7.73 (t, 1H), 7.80 (d, 1H), 7.95 (dd, 1H), 8.72 (m, 1H), 8.81 (s, 1H), 8.86 (dd, 1H), 9.10 (s, 1H), 9.78 (br, NH).

Example 46

N-Isobutyl-1-{3-[6-(1-hydroxy-1-methylethyl)pyridin-3-yl]phenyl}-1,4-dihydro[1,8]naphthyridin-4-one-3-carboxamide

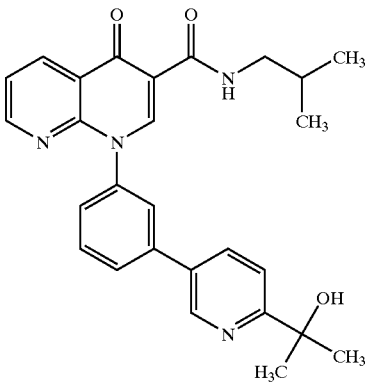

Step 1: 5-(3-Aminophenyl)-2-(1-hydroxy-1-methylethyl)pyridine

Following the procedure of Step 5 of Example 1, but substituting 3-aminophenylboronic acid for 3-acetyl phenylboronic acid and 5-bromo-2-(1-hydroxy-1-methylethyl) pyridine from Step 1 of Example 30 for N-isopropyl-1-(3-bromophenyl)-1,4-dihydro[1,8]naphthyridin-4-one-3-carboxamide, the 5-(3-Aminophenyl)-2-(1-hydroxy-1-methylethyl) pyridine compound was obtained as a solid.

Step 2: 1-{3-[6-(1-hydroxy-1-methylethyl)pyridin-3-yl]phenyl}-1,4-dihydro[1,8]naphthyridin-4-one-3-carboxylic Acid Following the procedures of Steps 1–3 of Example 1, but substituting 5-(3-aminophenyl)-2-(1-hydroxy-1-methylethyl)pyridine for 3-bromoaniline from Step 1 in the First Step, the 1-{3-[6-(1-hydroxy-1-methylethyl)pyridin-3-yl]phenyl}-1,4-dihydro[1,8]naphthyridin-4-one-3-carboxylic acid compound was obtained as a solid.

Step 3: N-Isobutyl-1-{3-[6-(1-hydroxy-1-methylethyl)pyridin-3-yl]phenyl}-1,4-dihydro[1,8]naphthyridin-4-one-3-carboxamide Following the procedure of Step 4 of Example 1, but substituting the acid from Step 2 for 1-(3-bromophenyl)-1,4-dihydro[1,8]naphthyridin-4-one-3-carboxylic acid, and isobutylamine for isopropylamine, the N-Isobutyl-1-{3-[6-(1-hydroxy-1-methylethyl)pyridin-3-yl]phenyl}-1,4-dihydro[1,8]naphthyridin-4-one-3-carboxamide compound was obtained as a cream-colored solid.

$^1$H NMR (Acetone-d$_6$) δ 0.98 (d, 6H), 1.53 (s, 6H), 1.88 (m, 1H), 3.26 (t, 2H), 4.66 (s, 1H, OH), 7.60 (m, 1H), 7.69 (d, 1H), 7.76–7.79 (m, 2H), 7.95 (d, 1H), 8.05 (s, 1H), 8.16 (dd, 1H), 8.73 (m, 1H), 8.79 (dd, 1H), 8.90 (s, 1H), 8.94 (s, 1H), 9.83 (br, NH).

Example 47

N-Cyclopropyl-1-{5-bromo-3-[6-(1-hydroxy-1-methylethyl)pyridin-3-yl]phenyl}-1,4-dihydro[1,8]naphthyridin-4-one-3-carboxamide

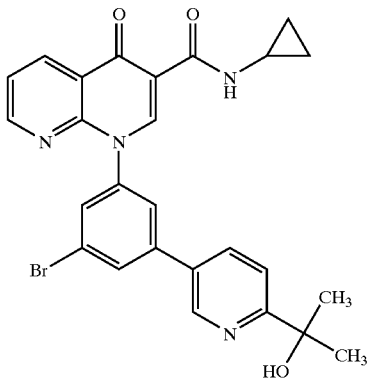

Step 1: 1-(3,5-Dibromophenyl)-1,4-dihydro[1,8]naphthyridin-4-one-3-carboxylic Acid Following the procedures of Steps 1–3 of Example 1, but substituting 3,5-dibromoaniline for 3-bromoaniline in Step 1, the 1-(3,5-Dibromophenyl)-1,4-dihydro[1,8]naphthyridin-4-one-3-carboxylic acid compound was obtained as a beige solid.

Step 2: N-Cyclopropyl-1-(3,5-dibromophenyl)-1,4-dihydro[1,8]naphthyridin-4-one-3-carboxamide Following the procedure of Step 4 of Example 1, but substituting the 1-(3,5-Dibromophenyl)-1,4-dihydro[1,8]naphthyridin-4-one-3-carboxylic acid from Step 1 for 1-(3-bromophenyl)-1,4-dihydro[1,8]naphthyridin-4-one-3-carboxylic acid, and cyclopropylamine for isopropylamine, the N-Cyclopropyl-1-(3,5-dibromophenyl)-1,4-dihydro[1,8]naphthyridin-4-one-3-carboxamide compound was obtained as a solid.

Step 3: 2-(1-hydroxy-1-methylethyl)-5-tributylstannylpyridine

To a suspension of 2,5-dibromopyridine in toluene (5 ml/mmol) at −78° C., was added n-butyllithium 2.5M in hexanes (1 eq) and the resulting mixture was stirred in the cold for 2.5 hours. Acetone (1 eq) was added, and the mixture was warmed to −50° C. and became a brown solution. After cooling down to −78° C., more n-butyllithium (1 eq) was added along with ether (2 ml/mmol). After stirring in the cold for a further hour, tributyltin chloride (1.1 eq) was added and the mixture was warmed to room temperature and stirred for 2 hours. The mixture was quenched with saturated aqueous ammonium chloride solution and partitioned between ethyl acetate and water. The crude product from the organic phase was chromatographed on silica gel eluting with a 1:9 mixture of ethyl acetate and hexane to afford the 2-(1-hydroxy-1-methylethyl)-5-tributylstannylpyridine compound as a colorless liquid.

Step 4: N-Cyclopropyl-1-{5-bromo-3-[6-(1-hydroxy-1-methylethyl)pyridin-3-yl]phenyl}-1,4-dihydro[1,8]naphthyridin-4-one-3-carboxamide A mixture of N-cyclopropyl-1-(3,5-dibromophenyl)-1,4-dihydro[1,8]naphthyridin-4-one-3-carboxamide from Step 2, 2-(1-hydroxy-1-methylethyl)-5-tributylstannylpyridine from Step 3 (1.4 eq), 1,1′-bis (diphenylphosphino)ferrocene] dichloropalladium(II) (0.05 eq), and cuprous iodide (0.05 eq) in N,N-dimethylformamide (15 ml/mmol) was stirred at 85° C. for 5 hours. After cooling the resulting mixture was partitioned between ethyl acetate and water. The crude product from the organic phase was chromatographed on silica gel eluting with a 1:6:3 mixture of ethanol, ethyl acetate and methylene chloride to afford the N-Cyclopropyl-1-{5-bromo-3-[6-(1-hydroxy-1-methylethyl)pyridin-3-yl]phenyl}-1,4-dihydro[1,8]naphthyridin-4-one-3-carboxamide compound as a solid.

$^1$H NMR (CDCl$_3$) δ 0.72 (m, 2H), 0.90 (m, 2H), 1.62 (s, 6H), 3.02 (m, 1H), 4.76 (s, 1H, OH), 7.50–7.56 (m, 2H), 7.62 (s, 1H), 7.69 (s, 1H), 7.90–7.96 (m, 2H), 8.74 (m, 1H), 8.79 (s, 1H), 8.86 (dd, 1H), 9.07 (s, 1H), 9.74 (br, NH).

Example 48

N-Cyclopropyl-1-{3-[6-(1-hydroxy-1-methylethyl)pyridin-2-yl]phenyl}-1,4-dihydro[1,8]naphthyridin-4-one-3-carboxamide

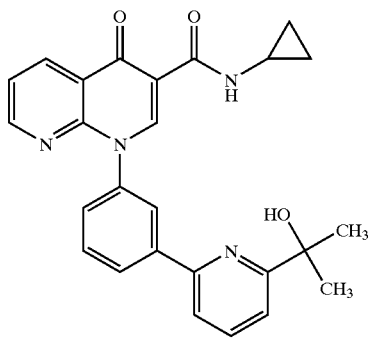

Step 1: 2-(1-hydroxy-1-methylethyl)-6-tributylstannylpyridine

Following the procedure of Step 3 of Example 47, but substituting 2,6-dibromopyridine for 2,5-dibromopyridine, the 2-(1-hydroxy-1-methylethyl)-6tributylstannylpyridine compound was obtained.

Step 2: N-Cyclopropyl-1-{3-[6-(1-hydroxy-1-methylethyl)pyridin-2-yl]phenyl}-1,4-dihydro[1,8]naphthyridin-4-one-3-carboxamide Following the procedure of Step 4 of Example 47, but substituting 2-(1-hydroxy-1-methylethyl)-6 tributylstannyl pyridine from Step 1 for 2-(1-hydroxy-1-methylethyl)-5-tributylstannylpyridine, the N-Cyclopropyl-1-{3-[6-(1-hydroxy-1-methylethyl)pyridin-2-yl]phenyl}-1,4-dihydro[1,8]naphthyridin-4-one-3-carboxamide compound was obtained as a solid.

$^1$H NMR (CDCl$_3$) δ 0.72 (m, 2H), 0.90 (m, 2H), 1.61 (s, 6H), 3.04 (m, 1H), 5.13 (s, 1H, OH), 7.40 (d, 1H), 7.46–7.53 (m, 2H), 7.70–7.76 (m, 2H), 7.85 (t, 1H), 8.13 (s, 1H), 8.22 (d, 1H), 8.73 (m, 1H), 8.87 (d, 1H), 9,12 (s, 1H), 9.83 (br, NH).

Example 49

N-Isopropyl-1-[3-(4-methylsulfonylphenyl)phenyl]-1,4-dihydro[1,8]naphthyridin-4-one-3-carboxamide

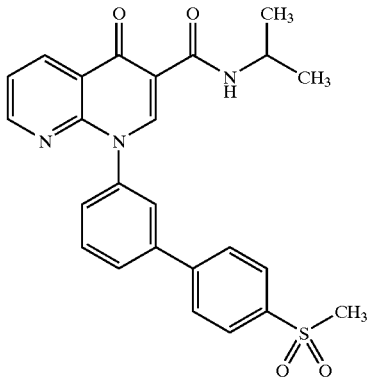

To a mixture of N-isopropyl-1-[3-(4-methylthiophenyl)phenyl]-1,4-dihydro[1,8]naphthyridin-4-one-3-carboxamide from Example 22 in tetrahydrofuran (24 ml/mmol), methanol (12 ml/mmol), and water (12 ml/mmol), was added oxone (2.24 eq) and the resulting mixture was stirred at room temperature for 2 hours. The mixture was quenched with saturated aqueous sodium bicarbonate and partitioned between ethyl acetate and water. The crude product from the organic phase was chromatographed on silica gel eluting with 30% ether in methylene chloride to afford the title compound as a white solid.

$^1$H NMR (Acetone-$d_6$) δ 1.25 (d, 6H), 3.16 (s, 3H), 4.18 (m, 1H), 7.60 (m, 1H), 7.74 (d, 1H), 7.79 (t, 1H), 7.99 (d, 1H), 8.05 (s, 4H), 8.09 (s, 1H), 8.72 (m, 1H), 8.78 (dd, 1H), 8.93 (s, 1H), 9.64 (br, NH).

Example 50

N-Cyclopropyl-1-[3-(6-methylsulfonylpyridin-3-yl)phenyl]-1,4-dihydro[1,8]naphthyridin-4-one-3-carboxamide

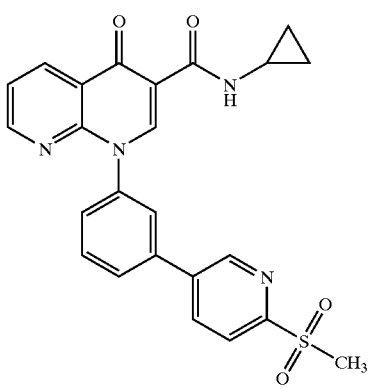

Step 1: 5-Bromo-2-methylthiopyridine

A mixture of 2,5-dibromopyridine and sodium thiomethoxide (1.3 eq) in N,N-dimethylformamide (2 ml/mmol) was stirred at room temperature for 20 minutes then cooled to 0° C. After diluting with cold water the precipitate was filtered to afford the 5-Bromo-2-methylthiopyridine compound as a solid.

Step 2: N-Cyclopropyl-1-[3-(6-methylthiopyridin-3-yl)phenyl]-1,4-dihydro[1,8]naphthyridin-4-one-3-carboxamide Following the procedure of Step 3 of Example 32, but substituting 5-bromo-2-methylthiopyridine from Step 1 for 3-bromo-5-methylsulfonylpyridine, the N-Cyclopropyl-1-[3-(6-methylthiopyridin-3-yl)phenyl]-1,4-dihydro[1,8]naphthyridin-4-one-3-carboxamide compound was obtained as a solid.

Step 3: N-Cyclopropyl-1-[3-(6-methylsulfonylpyridin-3-yl)phenyl]-1,4-dihydro[1,8]naphthyridin-4-one-3-carboxamide Following the procedure of Example 49, but substituting N-cyclopropyl-1-[3-(6-methylthiopyridin-3-yl)phenyl]-1,4-dihydro[1,8]naphthyridin-4-one-3-carboxamide from Step 2 for N-isopropyl-1-[3-(4-methylthiophenyl)phenyl]-1,4-dihydro[1,8]naphthyridin-4-one-3-carboxamide, the N-Cyclopropyl-1-[3-(6-methylsulfonylpyridin-3-yl)phenyl]-1,4-dihydro[1,8]naphthyridin-4-one-3-carboxamide compound was obtained as a solid.

$^1$H NMR (CDCl$_3$) δ 0.66 (m, 2H), 0.84 (m, 2H), 2.97 (m, 1H), 3.26 (s, 3H), 7.48 (m, 1H), 7.55 (d, 1H), 7.67 (s, 1H), 7.74–7.80 (m, 2H), 8.14–8.19 (m, 2H), 8.68 (m, 1H), 8.81 (dd, 1H), 8.96 (s, 1H), 9.05 (s, 1H), 9.73 (br, NH).

Example 51

N-Isopropyl-1-[3-(5-methylsulfonylpyridin-3-yl)phenyl]-1,4-dihydro[1,8]naphthyridin-4-one-3-carboxamide

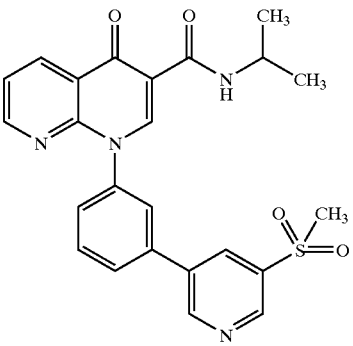

Following the procedure of Example 49, but substituting N-isopropyl-1-[3-(5-methylthiopyridin-3-yl)phenyl]-1,4-dihydro[1,8]naphthyridin-4-one-3-carboxamide from Example 15 for N-isopropyl-1-[3-(4-methylthiophenyl)phenyl]-1,4-dihydro[1,8]naphthyridin-4-one-3-carboxamide, the title compound was obtained as a solid.

$^1$H NMR (CDCl$_3$) δ 1.33 (d, 6H), 3.20 (s, 3H), 4.31 (m, 1H), 7.52 (m, 1H), 7.60 (d, 1H), 7.73 (s, 1H), 7.79 (t, 1H), 7.86 (d, 1H), 8.48 (m, 1H), 8.73 (m, 1H), 8.88 (d, 1H), 9.08 (s, 1H), 9.19 (d, 2H), 9.68 (br, NH).

Example 52

N-Cyclopropyl-1-[3-(4-ethylsulfonylphenyl)phenyl]-1,4-dihydro[1,8]naphthyridin-4-one-3-carboxamide

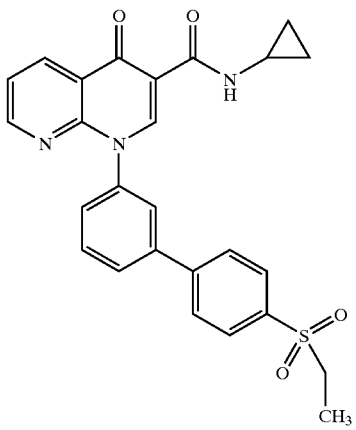

Following the procedure of Example 49, but substituting N-cyclopropyl-1-[3-(4-ethylthiophenyl)phenyl]-1,4-dihydro[1,8]naphthyridin-4-one-3-carboxamide from Example 18 for N-isopropyl-1-[3-(4-methylthiophenyl)phenyl]-1,4-dihydro[1,8]naphthyridin-4-one-3-carboxamide, the title compound was obtained as a solid.

$^1$H NMR (CDCl$_3$) δ 0.72 (m, 2H), 0.90 (m, 2H), 1.35 (t, 3H), 3.02 (m, 1H), 3.18 (q, 2H), 7.48–7.56 (m, 2H), 7.70 (s, 1H), 7.75 (t, 1H), 7.84 (m, 3H), 8.03 (d, 2H), 8.73 (m, 1H), 8.85 (dd, 1H), 9.10 (s, 1H), 9.80 (br, NH).

Example 53

N-Cyclopropyl-1-[3-(4-ethylsulfinylphenyl)phenyl]-1,4-dihydro[1,8]naphthyridin-4-one-3-carboxamide

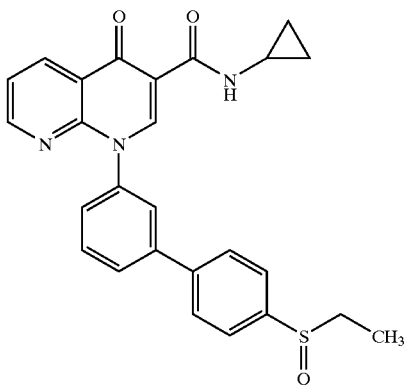

To a solution of N-cyclopropyl-1-[3-(4-ethylthiophenyl)phenyl]-1,4-dihydro[1,8]naphthyridin-4-one-3-carboxamide from Example 18, in a 1:1 mixture of methylene chloride and methanol (9 ml/mmol), was added at 0° C. magnesium monoperoxyphthalate hexahydrate (MMPP, 0.5 molareq) and the resulting mixture was stirred in the cold for 2 hours. The mixture was quenched with saturated aqueous sodium bicarbonate and partitioned between methylene chloride and water. The crude product from the organic phase was chromatographed on silica gel eluting with a 90:9:1 mixture of methylene chloride, ethanol and 28% aqueous ammonium hydroxide to afford the title compound as a solid.

$^1$H NMR (CDCl$_3$) δ 0.68 (m, 2H), 0.85 (m, 2H), 1.15 (m, 3H), 2.80 (m, 1H), 2.94 (m, 1H), 2.98 (m, 1H), 7.45–7.50 (m, 2H), 7.65–7.73 (m, 4H), 7.76–7.82 (m, 3H), 8.71 (m, 1H), 8.83 (dd, 1H), 9.06 (s, 1H), 9.78 (br, NH).

Example 54

N-Isopropyl-1-{3-[4-(1-oximidoethyl)phenyl]phenyl}-1,4-dihydro[1,8]naphthyridin-4-one-3-carboxamide

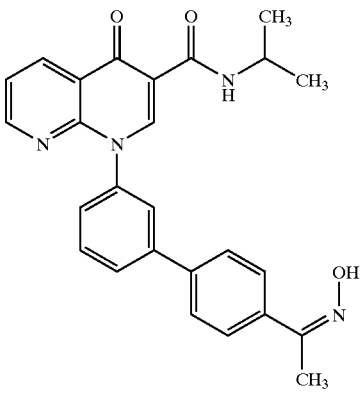

To a solution of N-isopropyl-1-[3-(4-acetylphenyl)phenyl]-1,4-dihydro[1,8]naphthyridin-4-one-3-carboxamide from Example 4 in pyridine (11 ml/mmol) at room temperature was added hydroxylamine hydrochloride (2.1 eq) and the resulting mixture was stirred for 16 hours. The mixture was filtered through celite and the filtrate evaporated. The residue was dissolved in ethyl acetate, washed with saturated aqueous sodium carbonate and then water, dried and evaporated. The residue was stirred in a small volume of acetone and filtered to afford the title compound as a solid.

$^1$H NMR (CDCl$_3$) δ 1.29 (d, 6H), 2.27 (s, 3H), 4.30 (m, 1H), 7.39 (d, 1H), 7.46 (m, 1H), 7.56 (d, 2H), 7.59–7.63 (m, 2H), 7.66 (d, 2H), 7.72 (d, 1H), 8.17 (s, 1H, OH), 8.69 (brs, 1H), 8.82 (d, 1H), 9.10 (s, 1H), 9.71 (br, NH).

Example 55

N-Isopropyl-1-{3-[4-(4-piperazin-1-yl)phenyl]phenyl}-1,4-dihydro[1,8]naphthyridin-4-one-3-carboxamide

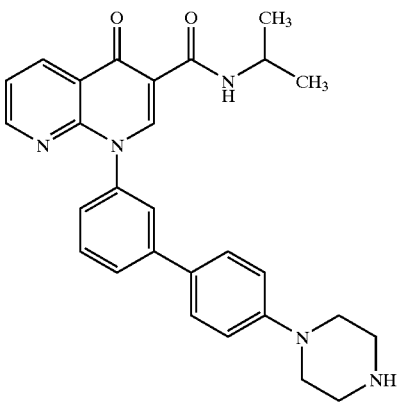

To a solution of N-isopropyl-1-{3-[4-(4-tertbutyloxycarbonylpiperazin-1-yl)phenyl]-phenyl}-1,4- dihydro[1,8]naphthyridin-4-one-3-carboxamide from Example 11 in methylene chloride (10 ml/mmol) was added trifluororacetic acid (6 ml/mmol) and the resulting mixture was stirred at room temperature for 2 hours, then warmed gently for 15 minutes. The mixture was evaporated and the crude product was chromatographed on silica gel eluting with a 9:0.9:0.1 mixture of methylene chloride, methanol and 28% aqueous ammonium hydroxide to afford the title compound as a solid.

$^1$H NMR (CDCl$_3$) δ 1.29 (d, 6H), 2.99 (m, 4H), 3.16 (m, 4H), 4.25 (m, 1H), 6.94 (d, 2H), 7.29 (d, 1H), 7.42 (m, 1H), 7.50 (d, 2H), 7.52–7.58 (m, 2H), 7.69 (d, 1H), 8.66 (m, 1H), 8.78 (dd, 1H), 9.04 (s, 1H), 9.69 (br, NH).

Example 56

N-Cyclopropyl-1-[3-(4-methylsulfonylmethylphenyl)phenyl]-1,4-dihydro[1,8]naphthyridin-4-one-3-carboxamide

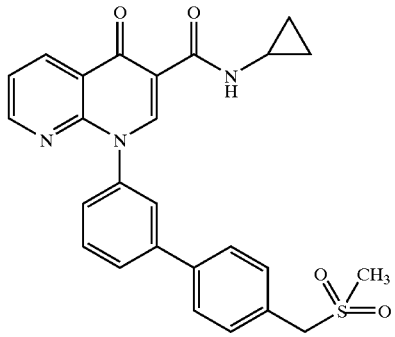

Step 1: N-Cyclopropyl-1-[3-(4-bromomethylphenyl)phenyl]-1,4-dihydro[1,8]naphthyridin-4-one-3-carboxamide A mixture of N-cyclopropyl-1-[3-(4-hydroxymethylphenyl)phenyl]-1,4-dihydro[1,8]naphthyridin-4-one-3-carboxamide from Example 16, carbon tetrabromide (2 eq), and diphos (0.6 molareq) in methylene chloride (15 ml/mmol) was stirred at room temperature for 3 hours. The mixture was concentrated at room temperature and chromatographed on silica gel eluting with a 1:1 mixture of ethyl acetate and methylene chloride to afford the N-Cyclopropyl-1-[3-(4-bromomethylphenyl)phenyl]-1,4-dihydro[1,8]naphthyridin-4-one-3-carboxamide compound.

Step 2: N-Cyclopropyl-1-[3-(4-methylsulfonylmethylphenyl)phenyl]-1,4-dihydro[1,8naphthyridin-4-one-3-carboxamide To a solution of N-Cyclopropyl-1-[3-(4-bromomethylphenyl)phenyl]-1,4-dihydro[1,8]naphthyridin-4-one-3-carboxamide from Step 1 in N,N-dimethylformamide (20 ml/mmol) was added methanesulfinic acid sodium salt (1.3 eq) and the resulting mixture was stirred at room temperature for 18 hours. To the mixture was added saturated aqueous ammonium chloride solution and ethyl acetate, and the insoluble solid was filtered and washed well with water, hexane, ether and ethyl acetate to afford the title compound as a solid.

$^1$H NMR (CDCl$_3$) δ 0.72 (m, 2H), 0.89 (m, 2H), 2.85 (s, 3H), 3.04 (m, 1H), 4.34 (s, 2H) 7.46–7.52 (m, 2H), 7.55 (d, 2H), 7.65–7.73 (m, 4H), 7.80 (d, 1H), 8.76 (d, 1H), 8.85 (d, 1H), 9.12 (s, 1H), 9.82 (br, NH).

Example 57

N-Cyclopropyl-1-[3-(1,6-dihydro-6-oxopyridin-3-yl)phenyl]-1,4-dihydro[1,8]naphthyridin-4-one-3-carboxamide

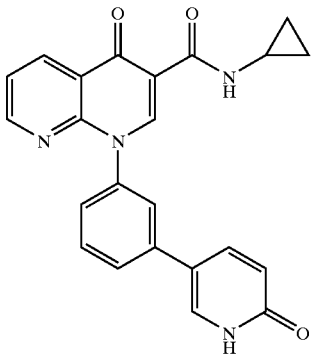

To a solution of N-cyclopropyl-1-[3-(6-benzyloxypyridin-3-yl)phenyl]-1,4-dihydro[1,8]naphthyridin-4-one-3-carboxamide from Example 42 in 1,2-dichloroethane (25 ml/mmol) was added trifluoroacetic acid (1.5 ml/mmol) and the resulting mixture was stirred at 60° C. for 18 hours. More trifluoroacetic acid was added (0.75 ml/mmol) and heating was continued for a further 24 hours. The cooled mixture was diluted with methylene chloride and saturated aqueous sodium bicarbonate was added, resulting in precipitation of a solid which was filtered. From the filtrate the organic phase was collected and evaporated to a solid which was combined with the previous filtered solid. This mixture was chromatographed on silica gel eluting with 10% methanol in methylene chloride to afford the title compound as a white fluffy solid.

$^1$H NMR (DMSO-d$_6$) δ 0.57 (m, 2H), 0.78 (m, 2H), 2.90 (m, 1H), 6.45 (d, 1H), 7.52 (m, 1H), 7.61–7.65 (m, 2H), 7.78 (d, 1H), 7.85 (s, 1H), 7.89–7.93 (m, 2H), 8.74 (d, 1H), 8.78–8.81 (m, 2H), 9.73 (br, NH), other NH>11 ppm.

Example 58

N-Cyclopropyl-1-[[3-{5-[6-(1-hydroxy-1-methylethyl)pyridin-3-yl]pyridin-3-yl}phenyl]]-1,4-dihydro[1,8]naphthyridin-4-one-3-carboxamide

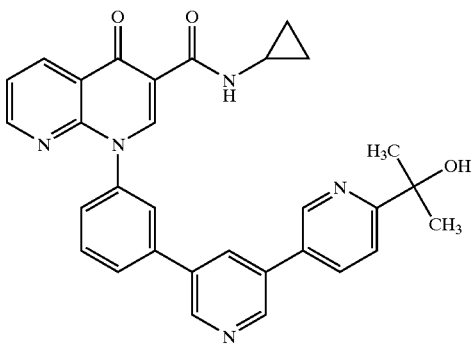

Following the procedure of Step 4 of Example 47, but substituting N-cyclopropyl-1-[3-(5-bromopyridin-3-yl)phenyl]-1,4-dihydro[1,8]naphthyridin-4-one-3-carboxamide from Example 41 for N-cyclopropyl-1-(3,5-dibromophenyl)-1,4-dihydro[1,8]naphthyridin-4-one-3-carboxamide, the title compound was obtained as a white solid.

¹H NMR (DMSO-d₆) δ 0.58 (m, 2H), 0.79 (m, 2H), 2.91 (m, 1H), 5.30 (s, 1H, OH), 7.65 (m, 1H), 7.71–7.79 (m, 3H), 8.12 (d, 1H), 8.23–8.26 (m, 2H), 8.49 (s, 1H), 8.75 (dd, 1H), 8.80 (m, 1H), 8.87 (s, 1H), 8.97 (m, 2H), 9.04 (s, 1H), 9.74 (br, NH).

Example 59

N-Isopropyl-1-[3-(1-oxidopyridin-3-yl)phenyl]-1,4-dihydro[1,8]naphthyridin-4-one-3-carboxamide

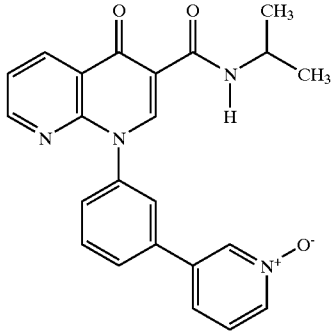

Following the procedure of Step 2 of Example 30, but substituting N-isopropyl-1-[3-(pyridin-3-yl)phenyl]-1,4-dihydro[1,8]naphthyridin-4-one-3-carboxamide from Example 7 for 5-bromo-2-(1-hydroxy-1-methylethyl) pyridine, the title compound was obtained as a white solid.

¹H NMR (DMSO-d₆) δ 1.21 (d, 6H), 4.10 (m, 1H), 7.51 (t, 1H), 7.64 (m, 1H), 7.71–7.75 (m, 3H), 7.97 (m, 1H), 8.09 (s, 1H), 8.23 (d, 1H), 8.69–8.77 (m, 3H), 8.84 (s, 1H), 9.66 (br, NH).

Example 60

N-(2,6-Dichloropyridin-4-yl)-1-[3-(1-oxidopyridin-3-yl)phenyl]-1,4-dihydro[1,8]naphthyridin-4-one-3-carboxamide

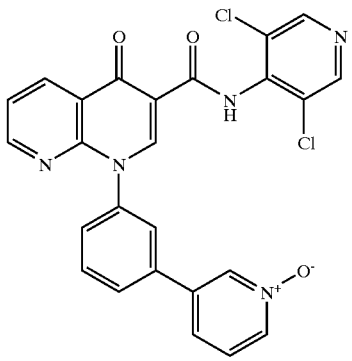

Following the procedure of Step 2 of Example 30, but substituting N-(2,6-dichloropyridin-4-yl)-1-[3-(pyridin-3-yl)phenyl]-1,4-dihydro[1,8]naphthyridin-4-one-3-carboxamide from Example 10 for 5-bromo-2-(1-hydroxy-1-methylethyl) pyridine, the title compound was obtained as a white solid.

¹H NMR (DMSO-d₆) δ 7.51 (m, 1H), 7.69–7.78 (m, 4H), 7.99 (dd, 1H), 8.14 (s, 1H), 8.24 (dd, 1H), 8.70 (s, 1H), 8.73 (s, 2H), 8.84 (m, 2H), 8.99 (s, 1H), 12.05 (br, NH).

Example 61

N-Isopropyl-1-[3-(5-carboethoxy-1-oxidopyridin-3-yl)phenyl]-1,4-dihydro[1,8]naphthyridin-4-one-3-carboxamide

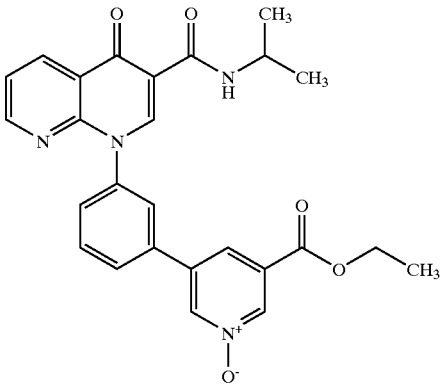

Following the procedure of Step 2 of Example 30, but substituting N-isopropyl-1-[3-(5-carboethoxypyridin-3-yl)phenyl]-1,4-dihydro[1,8]naphthyridin-4-one-3-carboxamide from Example 24 for 5-bromo-2-(1-hydroxy-1-methylethyl)pyridine, the title compound was obtained as a white solid.

¹H NMR (CDCl₃) δ 1.28 (d, 6H), 1.40 (t, 3H), 4.28 (m, 1H), 4.43 (q, 2H), 7.49 (dd, 1H), 7.56 (m, 1H), 7.68 (s, 1H), 7.73 (d, 2H), 8.04 (s, 1H), 8.60 (s, 1H), 8.68 (dd, 1H), 8.77 (s, 1H), 8.82 (d, 1H), 9.01 (s, 1H), 9.61 (br, NH).

Example 62

N-Isopropyl-1-{3-[5-(1-hydroxy-1-methylethyl)-1-oxidopyridin-3-yl]phenyl}-1,4-dihydro[1,8]naphthyridin-4-one-3-carboxamide

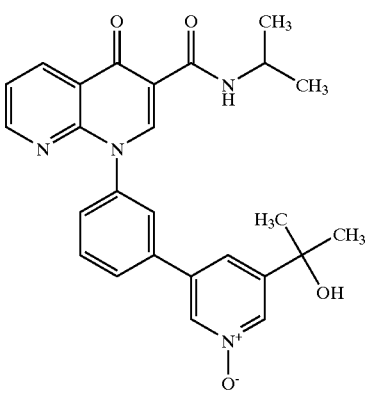

Following the procedure of Step 2 of Example 30, but substituting N-isopropyl-1-{3-[5-(1-hydroxy-1-methylethyl)pyridin-3-yl]phenyl}-1,4-dihydro[1,8]naphthyridin-4-one-3-carboxamide from Example 25 for 5-bromo-2-(1-hydroxy-1-methylethyl) pyridine, the title compound was obtained as a white solid.

¹H NMR (CDCl₃) δ 1.29 (d, 6H), 1.60 (s, 6H), 4.11 (brs, 1H), 4.23 (m, 1H), 7.42–7.51 (m, 2H), 7.58 (s, 2H) 7.65 (m, 2H), 8.28 (s, 1H), 8.33 (s, 1H), 8.64 (m, 1H), 8.80 (d, 1H), 8.98 (s, 1H), 9.61 (br, NH).

Example 63

N-Isopropyl-1-{3-[6-(2-methylpropyl)-1-oxidopyridin-3-yl]phenyl}-1,4-dihydro[1,8]naphthyridin-4-one-3-carboxamide

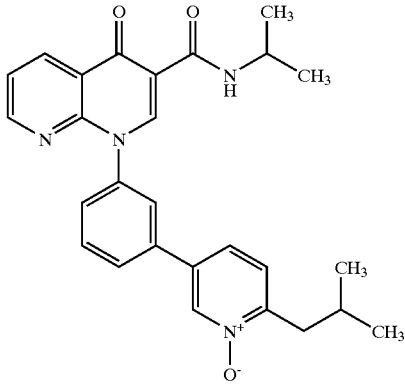

Following the procedure of Step 2 of Example 30, but substituting N-isopropyl-1-{3-[6-(2-methylpropyl)pyridin-3-yl]phenyl}-1,4-dihydro[1,8]naphthyridin-4-one-3-carboxamide from Example 26 for 5-bromo-2-(1-hydroxy-1-methylethyl) pyridine, the title compound was obtained as an off- white solid.

$^1$H NMR (CDCl$_3$) δ 0.98 (d, 6H), 1.29 (d, 6H), 2.29 (m, 1H), 2.32 (d, 2H), 4.26 (m, 1H), 7.28 (d, 1H), 7.38 (d, 1H), 7.47–7.52 (m, 2H), 7.60 (s, 1H), 7.69 (m, 2H), 8.53 (s, 1H), 8.69 (m, 1H), 8.82 (dd, 1H), 9.03 (s, 1H), 9.62 (br, NH).

Example 64

N-Isopropyl-1-[3-(6-methyl-1-oxidopyridin-3-yl)phenyl]-1,4-dihydro[1,8]naphthyridin-4-one-3-Carboxamide

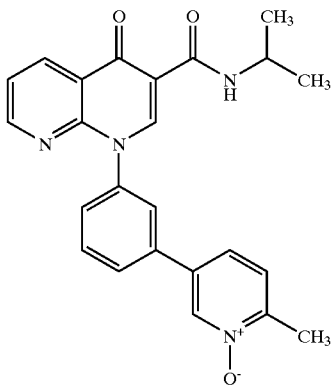

Following the procedure of Step 2 of Example 30, but substituting N-isopropyl-1-[3-(6-methylpyridin-3-yl)phenyl]-1,4-dihydro[1,8]naphthyridin-4-one-3-carboxamide from Example 28 for 5-bromo-2-(1-hydroxy-1-methylethyl) pyridine, the title compound was obtained as an off-white solid.

$^1$H NMR (CDCl$_3$) δ 1.32 (d, 6H), 2.60 (s, 3H), 4.30 (m, 1H), 7.35–7.45 (m, 2H), 7.50 (m, 2H), 7.62 (s, 1H), 7.72 (d, 2H), 8.58 (s, 1H), 8.72 (m, 1H), 8.85 (dd, 1H), 9.06 (s, 1H), 9.66 (br, NH).

Example 65

N-Cyclopropyl-1-[3-(1-oxidopyridin-3-yl)phenyl]-1,4-dihydro[1,8]naphthyridin-4-one-3-carboxamide

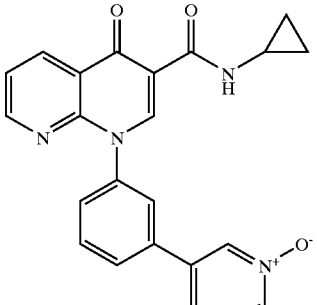

Following the procedure of Step 2 of Example 30, but substituting N-cyclopropyl-1-[3-(pyridin-3-yl)phenyl]-1,4-dihydro[1,8]naphthyridin-4-one-3-carboxamide from Example 14 for 5-bromo-2-(1-hydroxy-1-methylethyl) pyridine, the title compound was obtained as a white solid.

$^1$H NMR (DMSO-d$_6$) δ 0.57 (m, 2H), 0.78 (m, 2H), 2.90 (m, 1H), 7.52 (t, 1H), 7.65 (m, 1H), 7.72–7.76 (m, 3H), 7.98 (m, 1H), 8.10 (s, 1H), 8.25 (d, 1H), 8.70–8.79 (m, 3H), 8.85 (s, 1H), 9.72 (br, NH).

Example 66

N-Cyclopropyl-1-{3-[6-(1-hydroxy-1-methylethyl)-1-oxidopyridin-3-yl]phenyl}-1,4-dihydro[1,8]naphthyridin-4-one-3-carboxamide

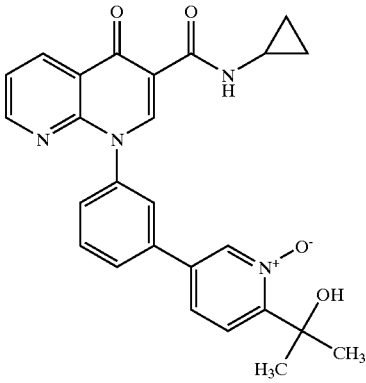

Following the procedure of Step 2 of Example 29 but substituting 5-bromo-2-(1-hydroxy-1-methylethyl) pyridine N-oxide from Step 2 of Example 30 for 5-bromo-1-oxidopyrimidine, the title compound was obtained as a white solid.

$^1$H NMR (CDCl$_3$) δ 0.66 (m, 2H), 0.85 (m, 2H), 1.70 (s, 6H), 2.97 (m, 1H), 7.43–7.49 (m, 2H), 7.52–7.56 (m, 2H), 7.61 (s, 2H) 7.71–7.74 (m, 2H), 8.49 (s, 1H), 8.68 (m, 1H), 8.80 (d, 1H), 9.02 (s, 1H), 9.74 (br, NH).

Example 67

N-Cyclopropyl-1-[3-(1-oxidopyridin-4-yl)phenyl]-1,4-dihydro[1,8]naphthyridin-4-one-3-carboxamide

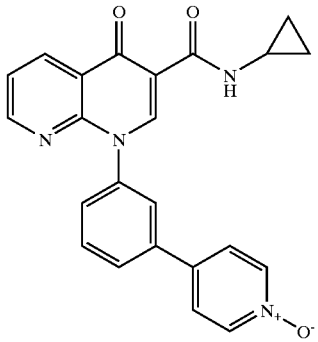

Following the procedure of Step 2 of Example 30, but substituting N-cyclopropyl-1-[3-(pyridin-4-yl)phenyl]-1,4-dihydro[1,8]naphthyridin-4-one-3-carboxamide from Example 17 for 5-bromo-2-(1-hydroxy-1-methylethyl) pyridine, the title compound was obtained as a white solid.

$^1$H NMR (DMSO-d$_6$) δ 0.57 (m, 2H), 0.79 (m, 2H), 2.92 (m, 1H), 7.62–7.70 (m, 2H), 7.75 (t, 1H), 7.88 (d, 2H), 8.03 (d, 1H), 8.15 (s, 1H), 8.30 (d, 2H), 8.75 (d, 1H), 8.80 (m, 1H), 8.86 (s, 1H), 9.73 (br, NH).

Example 68

N-Cyclopropyl-1-[3-(5-bromo-1-oxidopyridin-3-yl)phenyl]-1,4-dihydro[1,8]naphthyridin-4-one-3-carboxamide

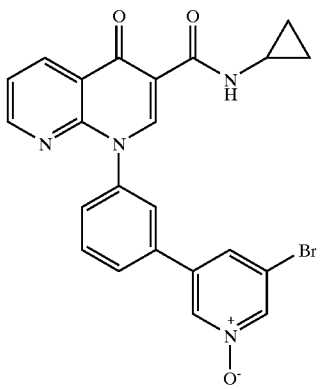

Following the procedure of Step 2 of Example 30, but substituting N-cyclopropyl-1-[3-(5-bromopyridin-3-yl)phenyl]-1,4-dihydro[1,8]naphthyridin-4-one-3-carboxamide from Example 41 for 5-bromo-2-(1-hydroxy-1-methylethyl) pyridine, the title compound was obtained as a light yellow solid.

$^1$H NMR (DMSO-d$_6$) δ 0.56 (m, 2H), 0.78 (m, 2H), 2.91 (m, 1H), 7.65 (m, 1H), 7.71–7.74 (m, 2H), 8.02–8.06 (m, 2H), 8.15 (s, 1H), 8.60 (s, 1H), 8.73–8.79 (m, 3H), 8.86 (s, 1H), 9.73 (br, NH).

Example 69

N-Cyclopropyl-1-[[3-{5-[6-(1-hydroxy-1-methylethyl)-1-oxidopyridin-3-yl]pyridin-3-yl}phenyl]]-1,4-dihydro[1,8]naphthyridin-4-one-3-carboxamide

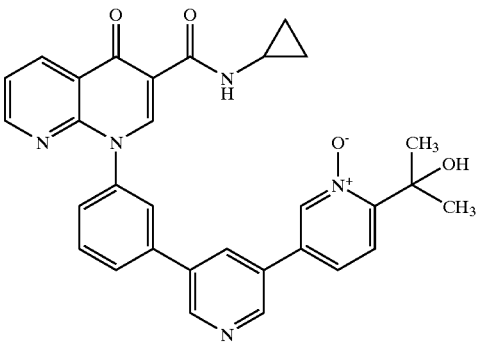

Following the procedure of Step 2 of Example 30, but substituting N-cyclopropyl-1-[[3-{5-[6-(1-hydroxy-1-methylethyl)pyridin-3-yl]pyridin-3-yl}phenyl]]-1,4-dihydro[1,8]naphthyridin-4-one-3-carboxamide from Example 58 for 5-bromo-2-(1-hydroxy-1-methylethyl) pyridine, and using 1.6 eq. of m-chloroperoxybenzoic acid, the title compound was obtained as a white solid.

$^1$H NMR (DMSO-d$_6$) δ 0.57 (m, 2H), 0.78 (m, 2H), 2.91 (m, 1H), 6.94 (s, 1H, OH), 7.65 (m, 1H), 7.71–7.79 (m, 3H), 7.97 (dd, 1H), 8.13 (d, 1H), 8.25 (s, 1H), 8.55 (s, 1H), 8.74 (dd, 1H), 8.80 (m, 1H), 8.87 (s, 1H), 8.91 (s, 1H), 9.00 (s, 1H), 9.09 (s, 1H), 9.73 (br, NH).

Example 70

N-Cyclopropyl-1-[[3-{5-[6-(1-hydroxy-1-methylethyl)pyridin-3-yl]-1-oxidopyridin-3-yl}phenyl]]-1,4-dihydro[1,8]naphthyridin-4-one-3-carboxamide

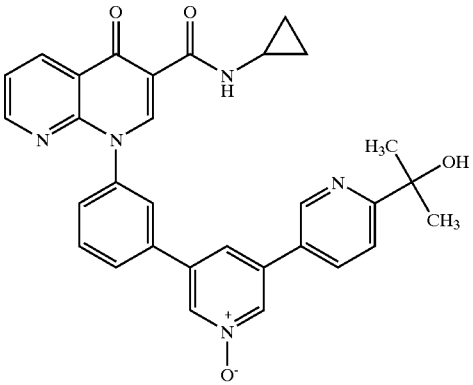

From the procedure of Example 69, the title compound was also obtained as a white solid.

$^1$H NMR (DMSO-d$_6$) δ 0.57 (m, 2H), 0.79 (m, 2H), 2.92 (m, 1H), 5.32 (s, 1H, OH), 7.65 (m, 1H), 7.72–7.80 (m, 3H), 8.08–8.17 (m, 2H), 8.27 (m, 2H), 8.70–8.82 (m, 4H), 8.88 (s, 1H), 8.98 (s, 1H), 9.73 (br, NH).

Example 71

N-Cyclopropyl-1-[[3-{5-[6-(1-hydroxy-1-methylethyl)-1-oxidopyridin-3-yl]-1-oxidopyridin-3-yl}phenyl]]-1,4-dihydro[1,8]naphthyridin-4-one-3-carboxamide

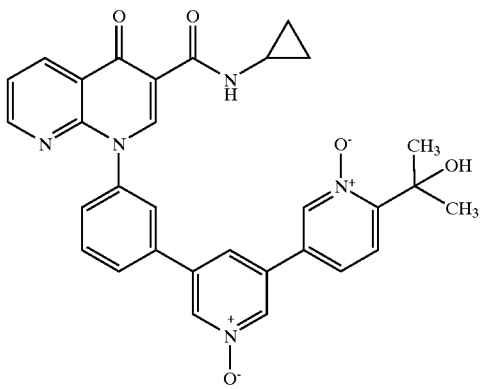

From the procedure of Example 69 the title compound was also obtained as a white solid.

$^1$H NMR (DMSO-$d_6$) δ 0.58 (m, 2H), 0.80 (m, 2H), 2.92 (m, 1H), 6.85 (brs, 1H, OH), 7.65 (m, 1H), 7.70–7.80 (m, 3H), 7.96 (d, 1H), 8.13 (m, 2H), 8.29 (s, 1H), 8.71–8.84 (m, 4H), 8.89 (s, 1H), 8.92 (s, 1H), 9.73 (br, NH).

Example 72

N-Isopropyl-1-[3-(1-oxidoquinolin-3-yl)phenyl]-1,4-dihydro[1,8]naphthyridin-4-one-carboxamide

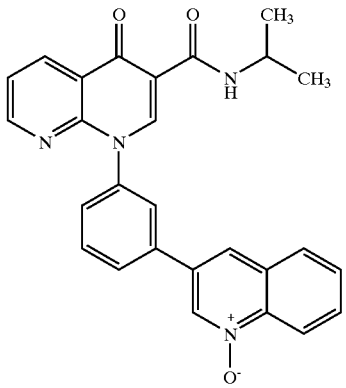

Following the procedure of Step 2 of Example 30, but substituting N-isopropyl-1-[3-(quinolin-3yl)phenyl]-1,4-dihydro[1,8]naphthyridin-4-one-carboxamide from Example 12 for 5-bromo-2-(1-hydroxy-1-methylethyl)pyridine, the title compound was obtained as a solid.

$^1$H NMR (CDCl$_3$) δ 1.30 (d, 6H), 4.28 (m, 1H), 7.49 (dd, 1H), 7.54 (d, 1H), 7.66–7.85 (m, 5H), 7.92 (m, 2H), 8.69–8.75 (m, 2H), 8.84 (d, 1H), 8.86 (s, 1H), 9.08 (s, 1H), 9.64 (br, NH).

Example 73

N-Isobutyl-1-{3-[6-(1-hydroxy-1-methylethyl)-1-oxidopyridin-3-yl]phenyl}-1,4-dihydro[1,8]naphthyridin-4-one-3-carboxamide

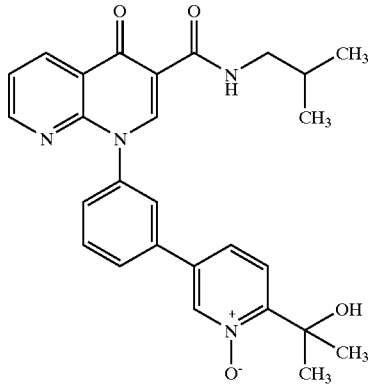

To a mixture of N-isobutyl-1-{3-[6-(1-hydroxy-1-methylethyl)pyridin-3-yl]phenyl}-1,4-dihydro[1,8]naphthyridin-4-one-3-carboxamide from Example 46 in 13:1 methylene chloride/methanol (33 ml/mmol) at room temperature was added magnesium monoperoxyphthalate hexahydrate (MMPP, 1.1 molareq) and the resulting mixture was stirred at room temperature for 24 hours. The mixture was filtered through a bed of celite and the filtrate was washed with aqueous sodium carbonate, then water and dried. The crude product was chromatographed on silica gel eluting with 8% ethanol in ethyl acetate and the solid obtained was stirred at room temperature in ether for several hours and filtered to afford the title compound as a light pink solid.

$^1$H NMR (Acetone-$d_6$) δ 0.98 (d, 6H), 1.61 (s, 6H), 1.88 (m, 1H), 3.26 (t, 2H), 7.52 (s, 1H, OH), 7.61 (m, 1H), 7.66 (d, 1H), 7.77–7.82 (m, 2H), 7.88 (d, 1H), 7.99 (d, 1H), 8.12 (s, 1H), 8.68 (s, 1H), 8.73 (m, 1H), 8.80 (dd, 1H), 8.93 (s, 1H), 9.81 (br, NH).

Example 74

N-Cyclopropyl-1-[3-(6-methyl-1-oxidopyridin-3-yl)]phenyl]-1,4-dihydro[1,8]naphthyridin-4-one-3-carboxamide

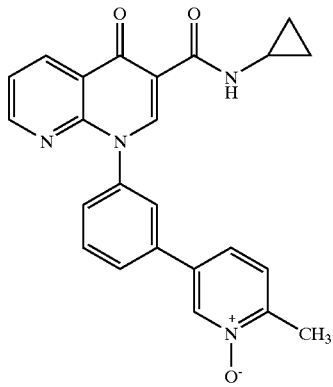

Following the procedure of Example 73, but substituting N-cyclopropyl-1-[3-(6-methylpyridin-3-yl)]phenyl]-1,4- dihydro [1,8]naphthyridin-4-one-3-carboxamide from Example 39 for N-isobutyl-1{[3-[6-(1-hydroxy-1-methylethyl)pyridin-3-yl]phenyl}-1,4-dihydro[1,8]naphthyridin-4-one-3-carboxamide, the title compound was obtained as a solid.

$^1$H NMR (CDCl$_3$) δ 0.72 (m, 2H), 0.91 (m, 2H), 2.61 (s, 3H), 3.02 (m, 1H), 7.38 (d, 1H), 7.45 (dd, 1H), 7.49–7.58 (m, 2H), 7.66 (s, 1H), 7.75 (m, 2H), 8.61 (s, 1H), 8.72 (m, 1H), 8.87 (dd, 1H), 9.08 (s, 1H), 9.78 (br, NH).

Example 75

N-Cyclopropyl-1-[3-(6-methylsulfonyl-1 oxidopyridin-3-yl)phenyl]-1,4-dihydro[1,8]naphthyridin-4-one-3-carboxamide

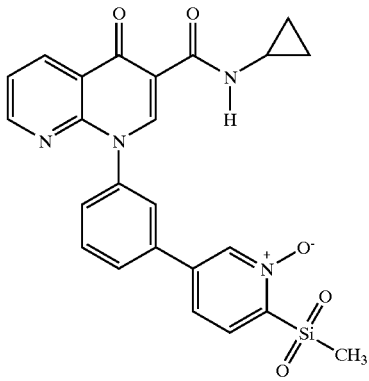

To a suspension of N-cyclopropyl-1-[3-(6-methylsulfonylpyridin-3-yl)phenyl]-1,4-dihydro[1,8]naphthyridin-4-one-3-carboxamide from Example 51 in methylene chloride (30 ml/mmol) was added urea-hydrogen peroxide (8 eq) and the resulting mixture was cooled to 0° C. Trifluoroacetic acid (4.7 eq) was added and the mixture was warmed to room temperature as a solution was obtained. After 18 hours, more urea-hydrogen peroxide (2.6 eq) and trifluoroacetic acid (2 eq) were added and stirring was continued for 2 hours. The mixture was quenched with saturated aqueous sodium metabisulfite, diluted with methylene chloride and the organic phase was washed with 1N aqueous HCl, then brine and water, dried and evaporated. The crude product was chromatographed on silica gel eluting with 40% toluene in acetone to afford the title compound as a solid.

$^1$H NMR (CDCl$_3$) δ 0.66 (m, 2H), 0.85 (m, 2H), 2.97 (m, 1H), 3.52 (s, 3H), 7.48 (m, 1H), 7.58–7.65 (m, 3H), 7.72–7–78 (m, 2H), 8.15 (d, 1H), 8.54 (s, 1H), 8.68 (brs, 1H), 8.81 (d, 1H), 9.01 (s, 1H), 9.71 (br, NH).

Example 76

N-Cyclopropyl-1-{5-bromo-3-[6-(1-hydroxy-1-methylethyl)-1-oxidopyridin-3-yl]phenyl}-1,4-dihydro[1,8]naphthyridin-4-one-3-carboxamide

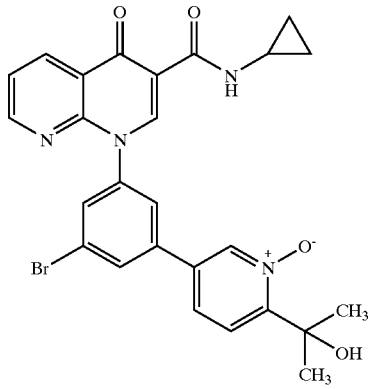

Following the procedure of Step 2 of Example 30, but substituting N-cyclopropyl-1-{5-bromo-3-[6-(1-hydroxy-1-methylethyl)pyridin-3-yl]phenyl}-1,4-dihydro[1,8]naphthyridin-4-one-3-carboxamide from Example 47 for 5-bromo-2-(1-hydroxy-1-methylethyl) pyridine, the title compound was obtained as a solid.

$^1$H NMR (CDCl$_3$) δ 0.71 (m, 2H), 0.90 (m, 2H), 1.75 (s, 6H), 3.02 (m, 1H), 7.48–7.60 (m, 5H), 7.73 (s, 1H), 7.88 (s, 1H), 8.52 (s, 1H), 8.72 (m, 1H), 8.84 (dd, 1H), 9.04 (s, 1H), 9.71 (br, NH).

Example 77

N-Cyclopropyl-1-{3-[6-(1,2-dihydroxy-1-methylethyl)-1-oxidopyridin-3-yl]phenyl}-1,4-dihydro[1,8]naphthyridin-4-one-3-carboxamide

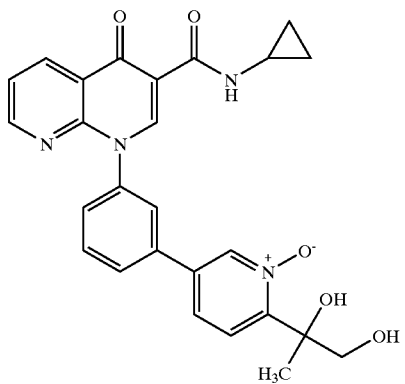

Step 1: 5-Bromo-2-(1-methylvinyl)pyridine N-oxide

A mixture of 5-bromo-2-(1-hydroxy-1-methylethyl) pyridine N-oxide from step 2 of example 30 (1.29 g) and 25% aqueous sulfuric acid was heated at 130° C. for 2 days. After cooling, the mixture was made slightly basic using 10N aqueous sodium hydroxide and partitioned between ethyl acetate and water. The crude product from evaporation of the organic phase was used as such in step 2.

Step 2: 5-Bromo-2-(1,2-dihydroxy-1-methylethyl)pyridine N-oxide

The crude product from step 1 was dissolved in a 3:1 mixture of acetone and water (16 mL) and 4-methylmorpholine N-oxide (1 g) and potassium osmate dihydrate (90 mg) were added. The resulting mixture was stirred at room temperature for 3 days then excess solid sodium bisulfite was added and the mixture was evaporated. The residue was diluted with methylene chloride and filtered. The filtrate was evaporated and the residue chromatographed on silica gel eluting with ethyl acetate to afford the title compound as a white solid.

Step 3: N-Cyclopropyl-1-{3-[6-(2-dihydroxy-1-methylethyl)-1-oxidopyridin-3-yl]phenyl}-1,4-dihydro[1,8]naphthyridin-4-one-3-carboxamide.

Following the procedure of step 2 of example 32 but substituting 5-bromo-2-(1,2-dihydroxy-1-methylethyl) pyridine N-oxide from step 2 for 3-bromo-5-methylsulfonylpyridine the title compound was obtained as a white solid.

$^1$H NMR (CDCl$_3$) δ 0.66 (m, 2H), 0.85 (m, 2H), 1.61 (s, 3H), 2.78 (m, 1H, OH), 2.97 (m, 1H), 3.90 (m, 1H), 3.97 (m, 1H), 7.48 (m, 1H), 7.53 (m, 2H), 7.60 (m, 2H), 7.69–7.72 (m, 2H), 7.92 (s, 1H, OH), 8.49 (s, 1H), 8.68 (m, 1H), 8.80 (dd, 1H), 9.02 (s, 1H), 9.73 (br, NH).

Other variations or modifications, which will be obvious to those skilled in the art, are within the scope and teachings of this invention. This invention is not to be limited except as set forth in the following claims.

What is claimed is:

1. A compound represented by Formula (I):

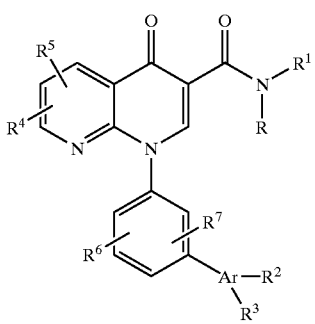

(I)

or a pharmaceutically acceptable salt thereof, wherein

Ar is pyridyl or pyridonyl or oxides thereof;

R is H or —C$_{1-6}$alkyl;

R$^1$ is H, or —C$_{1-6}$alkyl, —C$_{3-6}$cycloalkyl, —C$_{1-6}$alkoxy, —C$_{2-6}$alkenyl or —C$_{3-6}$alkynyl, optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-6}$alkyl, —O—N=C$_{1-6}$alkyl, or halogen substituents;

R$^2$ is H, halogen, —C$_{1-6}$alkyl, —C$_{3-6}$cycloalkyl, —C$_{1-6}$alkyl(C$_{3-6}$cycloalkyl)(C$_{3-6}$cycloalkyl), —C$_{1-6}$alkoxy, phenyl, amino, —C(O)—C$_{1-6}$alkyl, —C(O)—O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, SO$_n$NH(C$_{0-6}$alkyl), or —(C$_{0-6}$alkyl)—SO$_n$—(C$_{1-6}$alkyl), wherein the phenyl is optionally substituted with halogen, —C$_{1-6}$alkyl, —C$_{1-6}$alkoxy, hydroxy, amino, or —C(O)—O—C$_{1-6}$alkyl, and any alkyl is optionally substituted with 1–6 independent halogen or —OH substituents;

n is 0, 1, or 2;

R$^3$ is H, OH, amine, halogen or C$_{1-6}$alkyl, wherein the alkyl is optionally substituted with 1–6 independent halogen or OH; and R$^4$, R$^5$, R$^6$, and R$^7$ each independently is H, halogen, —C$_{1-6}$alkyl, —C$_{1-6}$alkoxy, or amine, and any alkyl is optionally substituted with 1–6 independent halogen or —OH substituents.

2. The compound according to claim 1, or a pharmaceutically acceptable salt, wherein Ar is pyridyl or oxide thereof.

3. The compound according to claim 2, or a pharmaceutically acceptable salt thereof, wherein R is H; and R$^1$ is H.

4. The compound according to claim 2, or a pharmaceutically acceptable salt, wherein R$^1$ is —C$_{1-6}$alkyl optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-6}$alkyl, —O—N=C$_{1-6}$alkyl, or halogen substituents.

5. The compound according to claim 2, or a pharmaceutically acceptable salt thereof, wherein R$^1$ is —C$_{3-6}$cycloalkyl optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-6}$alkyl, —O—N=C$_{1-6}$alkyl, or halogen substituents.

6. The compound according to claim 2, or a pharmaceutically acceptable salt, wherein R$^1$ is pyridyl optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-6}$alkyl, —O—N=C$_{1-6}$alkyl, or halogen substituents.

7. The compound according to claim 1, or a pharmaceutically acceptable salt thereof, wherein Ar is pyridonyl.

8. The compound according to claim 7, or a pharmaceutically acceptable salt thereof, wherein R$^1$ is —C$_{3-6}$cycloalkyl optionally substituted with 1–3 independent —C$_{1-6}$alkyl, —C$_{1-6}$alkoxy, OH, amino, —(C$_{0-6}$alkyl)—SO$_n$—(C$_{1-6}$alkyl), nitro, CN, =N—O—C$_{1-6}$alkyl, —O—N=C$_{1-6}$alkyl, or halogen substituents.

9. The compound according to claim 1, selected from the group consisting of

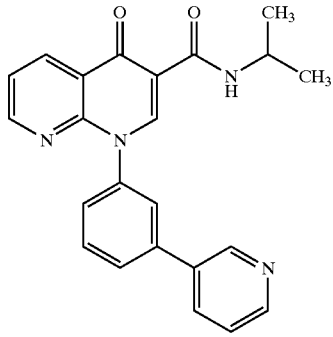

-continued
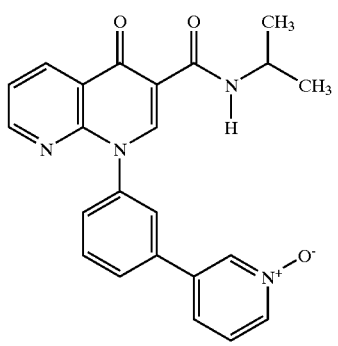
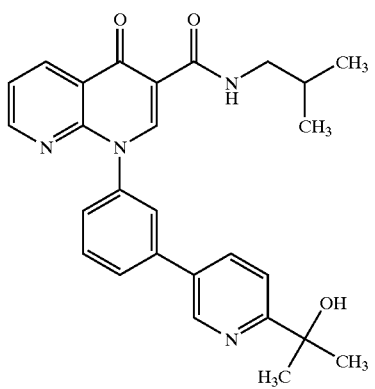
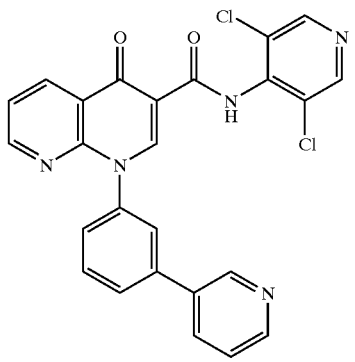
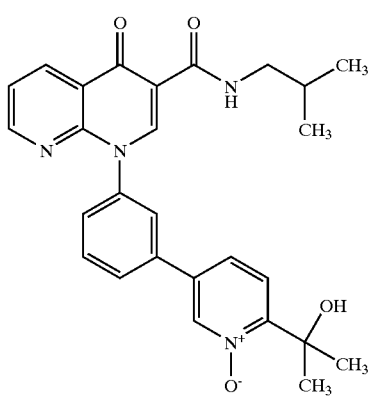
-continued
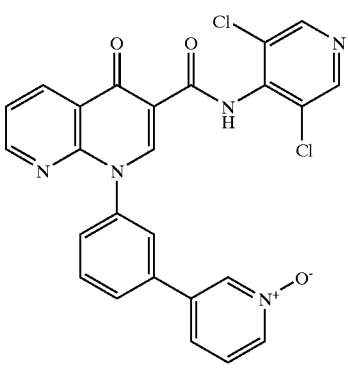
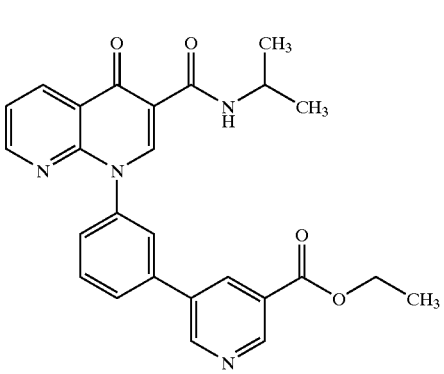
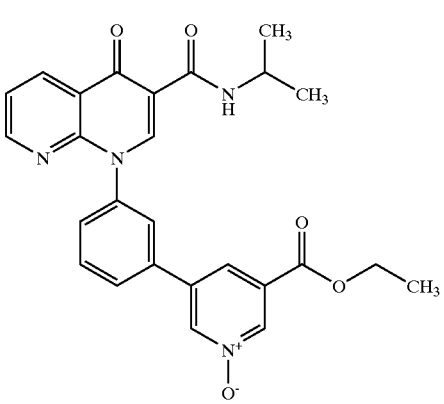
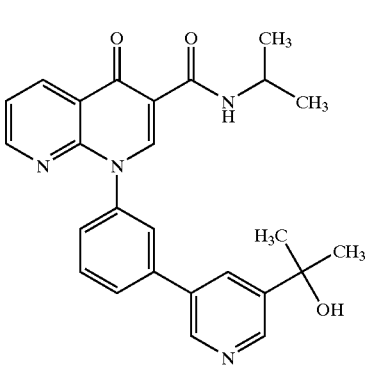

-continued
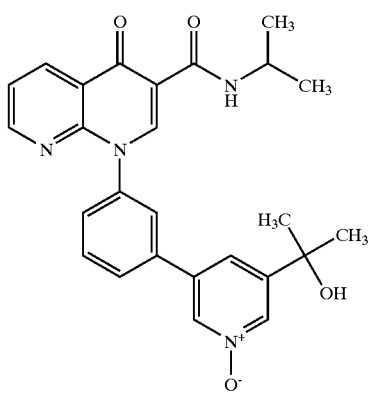
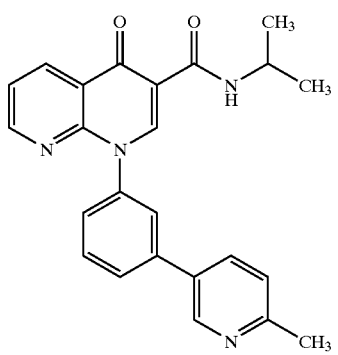
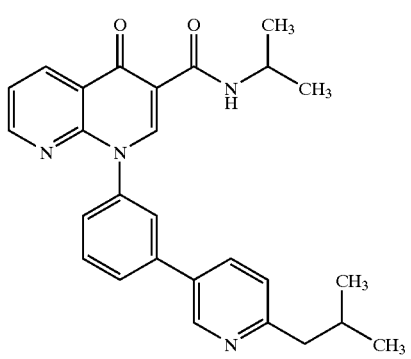
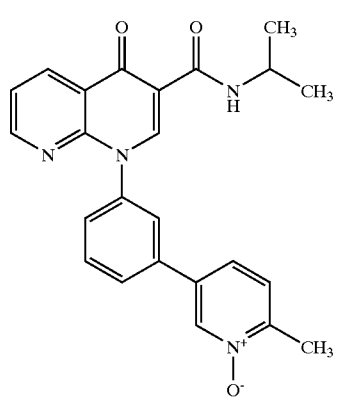
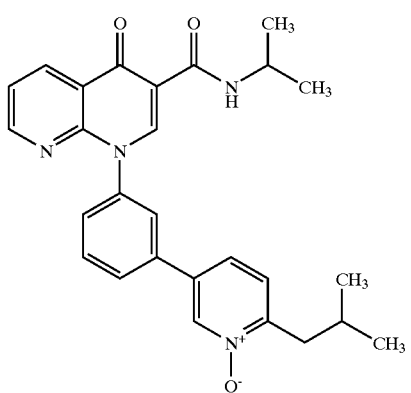
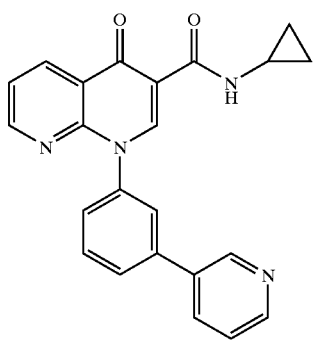
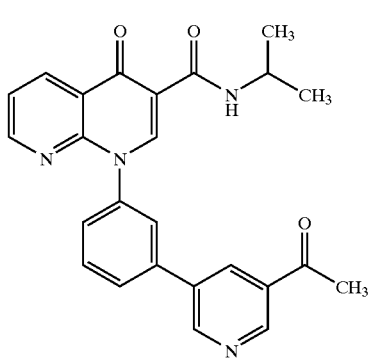
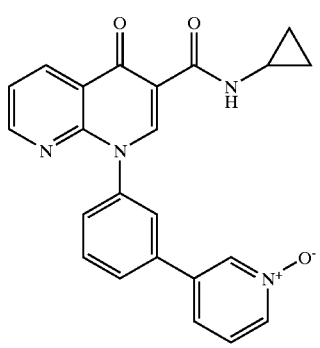

-continued
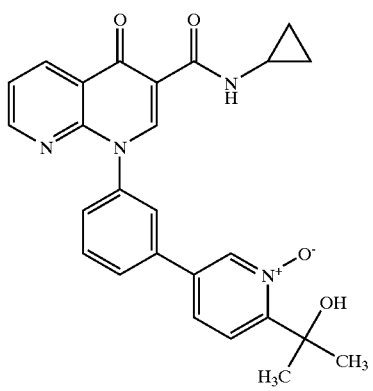
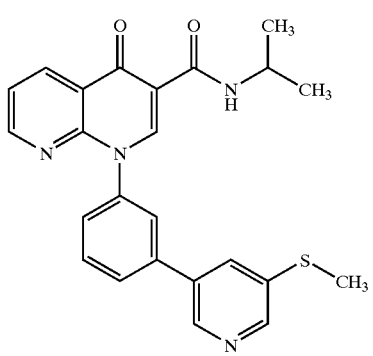
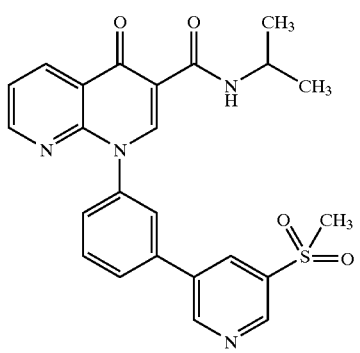
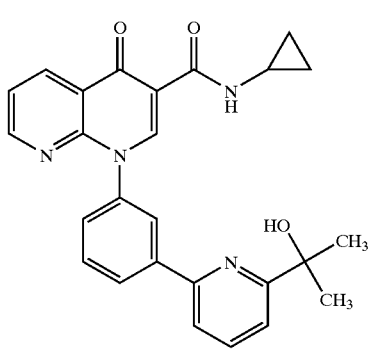
-continued
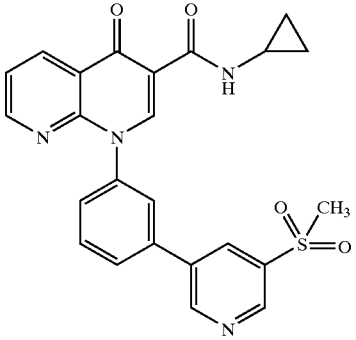
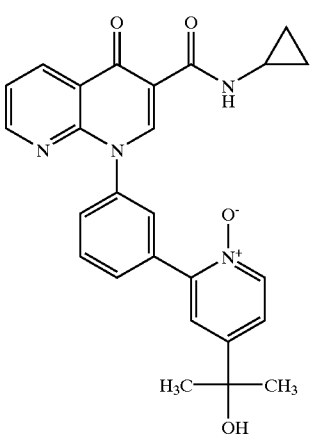
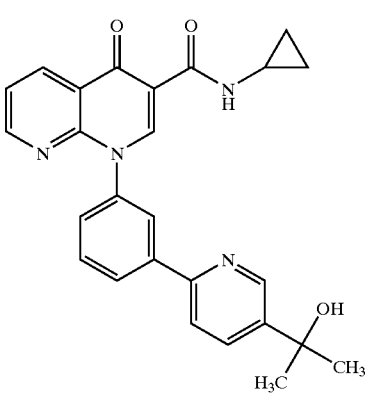
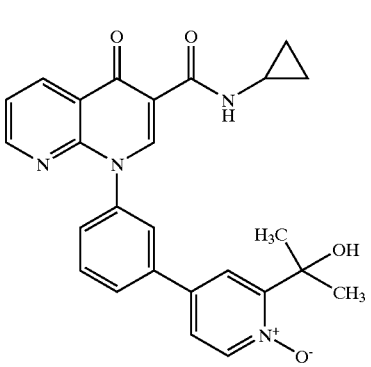

-continued
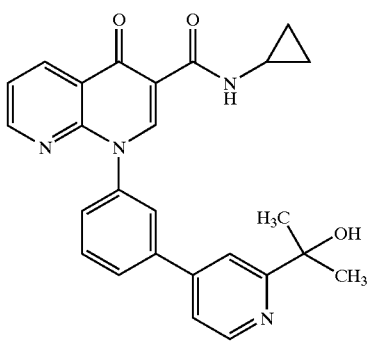
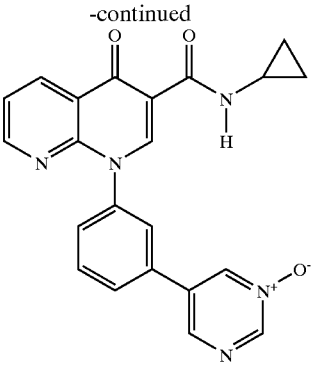
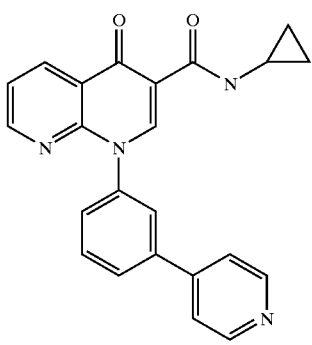
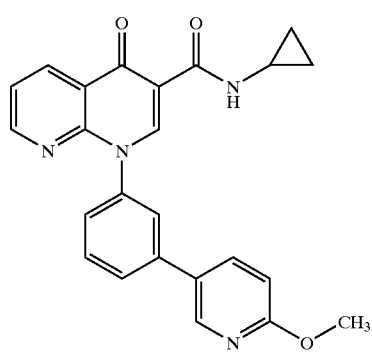
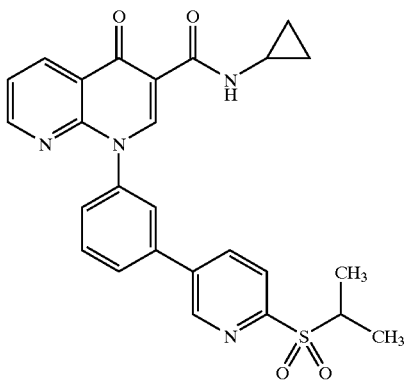
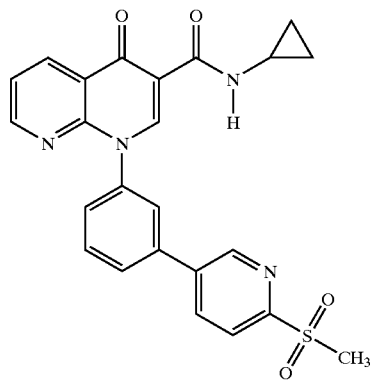
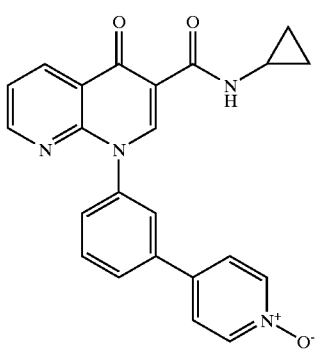
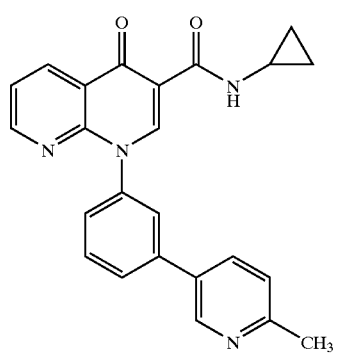

-continued
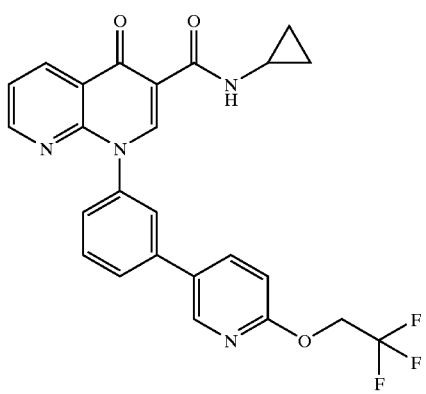
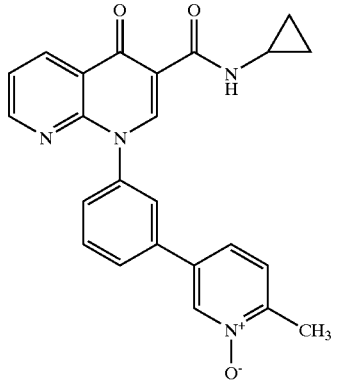
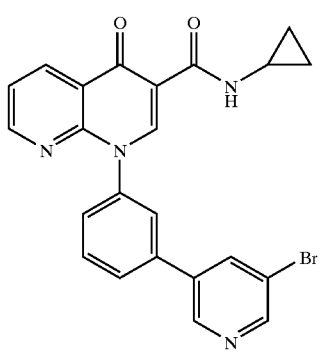
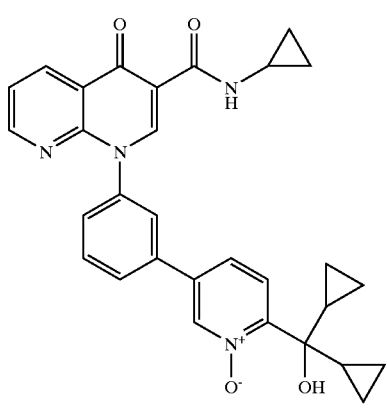
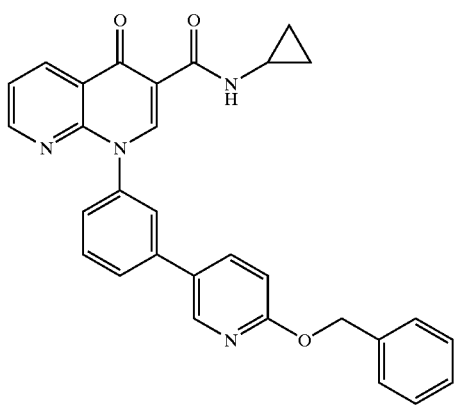
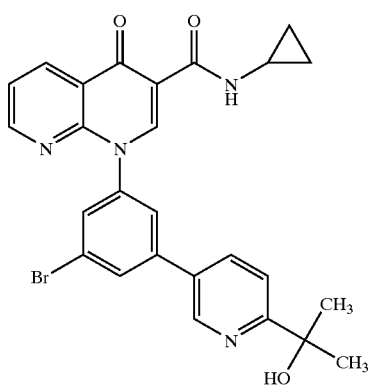
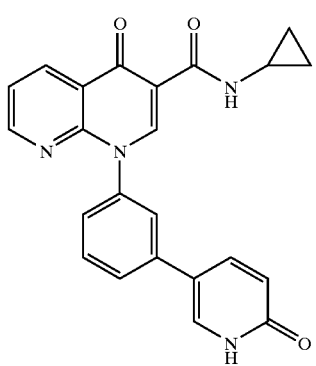
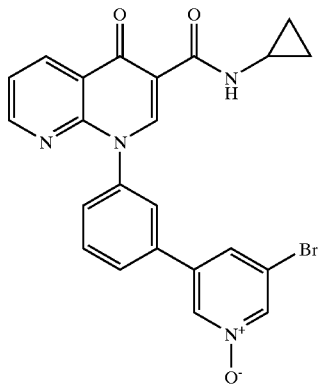

-continued
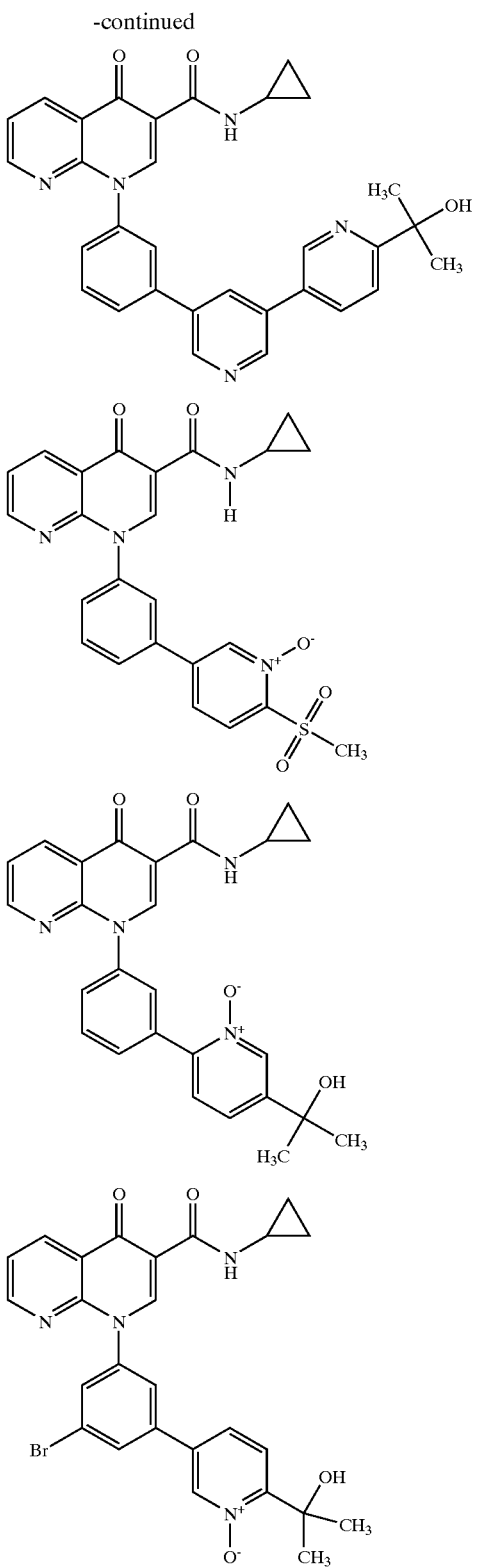
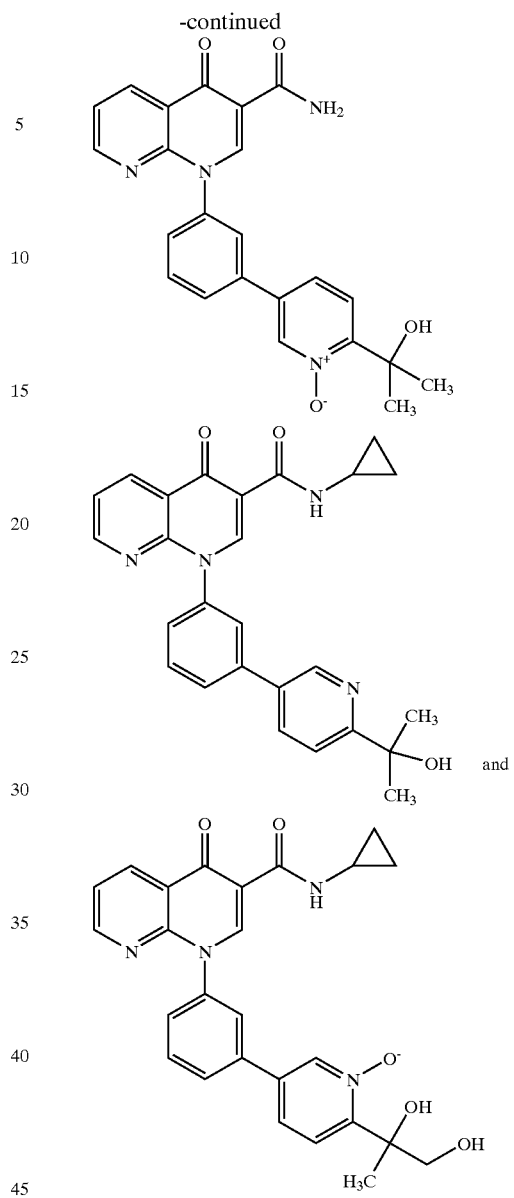
or a pharmaceutically acceptable salt thereof.
10. A pharmaceutical composition comprising
a therapeutically effective amount of the compound according to claim 1 or a pharmaceutically acceptable salt thereof; and
a pharmaceutically acceptable carrier.
* * * * *